United States Patent [19]
Woodruff

[11] Patent Number: 5,217,957
[45] Date of Patent: Jun. 8, 1993

[54] CHOLECYSTOKININ ANTAGONISTS USEFUL FOR TREATING DEPRESSION

[75] Inventor: Geoffrey N. Woodruff, Braughing, United Kingdom

[73] Assignee: Warner-Lambert Company, Morris Plains, N.J.

[21] Appl. No.: 747,813

[22] Filed: Aug. 20, 1991

[51] Int. Cl.⁵ .................. A61K 31/405; C07D 209/20; C07D 403/12
[52] U.S. Cl. ...................................... 514/18; 514/19; 514/530; 530/330; 530/331
[58] Field of Search ............................ 514/530, 18, 19; 530/330, 331

[56] References Cited

U.S. PATENT DOCUMENTS

| 4,791,215 | 12/1988 | Rovati et al. | 558/415 |
| 4,820,834 | 4/1989 | Evans et al. | 540/504 |
| 5,084,479 | 1/1992 | Woodruff | 514/530 |

FOREIGN PATENT DOCUMENTS 405537 1/1991 European Pat. Off. .

OTHER PUBLICATIONS

Berkow, editor "The Merck Manual of Diagnosis and Therapy", Fourteenth Edition, Published by Merck Sharp & Dohme Research Laboratories division of Merck & Co., Inc. Rahway, N.J., 1982, pp. 1448–1463.
Yu et al., "Quinazolinone Cholecystokinin-B-Receptor Ligands," J. Med. Chem. 1991, 34, pp. 1505–1508.
Bradwejn et al., "Cholecystokinin-Tetrapeptide Induces Panic Attacks in Patients with Panic Disorder," Can. J. Psychiatry vol. 35, Feb. 1990, pp. 83–85.
de Montigny, "Cholecystokinin Tetrapeptide Induces Panic-like Attacks in Healthy Volunteers," ARCH, GEN PSYCHIATRY, vol. 46, Jun. 1989, pp. 511–517.
Annu. Rev. Pharmacol. Toxicol., 1991, 31:469-501 "Cholecystokinin Antagonists", G. N. Woodruff et al.
Proc. Natl. Acad. Sci. USA, vol. 87, pp. 6728–6732 Sep. 1990, "Development of a Class . . . Cholecystokinin . . . ", J. Hughes et al.
Proc. Natl. Acad. Sci. USA, vol. 88, pp. 1130–1133, Feb. 1991, "Evidence for . . . Cholecystokinin B . . . " L. Singh et al.
Nature vol. 266, 21 Apr. 1977, pp. 730–732, "Depression: A New Animal Model . . . ", R. D. Porsolt, et al.

Primary Examiner—Ronald W. Griffin
Attorney, Agent, or Firm—Elizabeth M. Anderson

[57] ABSTRACT

The invention concerns cholecystokinin (CCK) antagonists useful in the treatment major and minor forms of depression. CCK-B, -A, and mixed -A and -B antagonists are useful. Especially useful are $CCK_B$ antagonists such as CI-988.

16 Claims, No Drawings

CHOLECYSTOKININ ANTAGONISTS USEFUL FOR TREATING DEPRESSION

BACKGROUND OF THE INVENTION

Cholecystokinin (CCK) is a neuropeptide with a widespread distribution in brain. CCK receptors are classified into two types; $CCK_A$ and $CCK_B$, both of which are present in brain (Woodruff, G. N. and Hughes, J., 1991, *Ann. Rev. Pharmacol.* 31, 469-501).

CI-988, the chemical name is: [R-(R*,R*)]-4-[[2-[[3-(1H-indol-3-yl)-2-methyl-1-oxo-2-[[(tricyclo[3.3.1.1$^{3,7}$]-dec-2-yloxy)carbonyl]amino]propyl]amino]-1-phenylethyl]amino]-4-oxobutanoic acid, and the structure is:

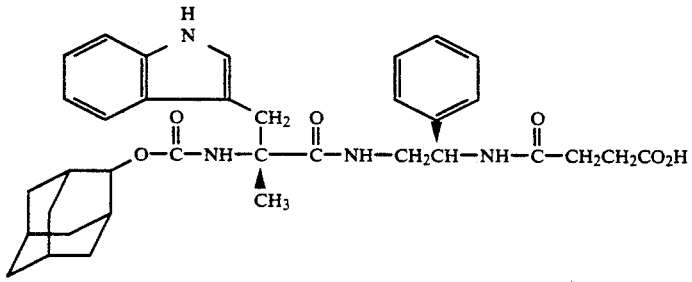

It is a potent $CCK_B$ antagonist with high selectivity for $CCK_B$ receptors (Hughes, J., et al, 1990, *Proc. Natl. Acad. Sci., USA*, 87 6728-6732). $CCK_B$ antagonists have been shown to have anxiolytic-like activity in animal models of anxiety (Hughes, J., et al, *Proc. Natl. Acad. Sci.*, USA, 87, 6728-6732; Singl, L., Lewis, A. S., Field, M. J., Hughes, J., and Woodruff, G. N., 1991, *Proc. Natl. Acad. Sci.*, USA, 88, 1130-1133), suggesting a physiological role for CCK in anxiety. It has also been suggested that CCK may be involved in the control of food intake and in analgesic responses (Woodruff, G. N. and Hughes, J., 1991, *Ann. Rev. Pharmacol.* 31, 469-501).

$CCK_A$ antagonists include but are not limited to (1R-trans)-N-[α-methyl-N-[[(2-methylcyclohexyl)oxy]carbonyl]-L-tryptophyl]-D-3-(phenylmethyl)((1R,2R)-N-[[(2-methylcyclohexyl)oxy]carbonyl])(α/-Me)LTrp-(D-3-Bzl)bAla-β-alanine ((−)-isomer) and N-[α-methyl-N-[(tricyclo[3.3.1.1$^{3,7}$]dec-2-yloxy)carbonyl]-L-tryptophyl]-D-3-(phenylmethyl)-β-alanine.

Mixed $CCK_A$ and $CCK_B$ antagonists include but are not limited to (1S-trans)-N-[α-methyl-N-[[(2-methylcyclohexyl)oxy]carbonyl]-D-tryptophyl]-L-3-(phenylmethyl)-β-alanine.

The above CCK antagonists have been described in EPA 0405537. These antagonists are also described in U.S. application Ser. No. 07/629,809, filed Dec. 19, 1990, the disclosure of which is hereby incorporated by reference.

Other CCK an have been described in pending U.S. application Ser. Nos. 07/726,656, 07/726,655, 07/726,654, 07/726,653, 07/726,652, and 07/726,651 are filed on Jul. 12, 1991, the disclosures of which are also hereby incorporated by reference.

The above patents and applications cover the compounds of the instant invention, methods for preparing them, and several uses thereof.

The above references do not disclose the use of $CCK_B$ antagonists for treating depression.

Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the diagnostic and Statistical Manual of Mental Disorders (Third Edition Revised) referred to as the DSM-III-R manual published by the American Psychiatric Association, 1987.

The compounds of the instant invention are indicated as having an antidepressant action in patients with major and minor forms of depression.

SUMMARY OF THE INVENTION AND DETAILED DESCRIPTION

The present invention relates to a novel therapeutic use of known compounds, $CCK_B$, $CCK_A$, and mixed CCK A and B antagonists, their derivatives, and pharmaceutically acceptable salts. The present invention concerns a method for treating depression in a mammal in need of such treatment.

The treatment comprises administering in unit dosage form an amount effective to treat depression of a $CCK_B$ antagonist or a pharmaceutically acceptable salt thereof to a mammal in need of such treatment.

Preferred compounds include but are not limited to:
1. [1-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]-propyl]amino]-1-phenylethyl]amino]-4-oxo-2-butenoic acid,
2. [1S-[1α, 2β[S*(S*)],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]methylamino]-1-phenylethyl]amino]-4-oxobutanoic acid,
3. [1S-[1α,2β[S*(S*)],4α]]-4-[[2-[[3-(1H-indol-3-yl-2-methyl-1-oxo-2-[[[(1,7,7-trimethylbicyclo[2.2.1]hept-2-yl)amino]carbonyl]amino]propyl]amino]-1-phenylethyl]amino]-4-oxobutanoic acid,
4. [R-(R*,R*)]-4-[[2-[[3-(1H-indol-3-yl)-2-methyl-1-oxo-2-[(tricyclo[3.3.1.1$^{3,7}$]dec-2-ylsulfonyl)amino]propyl]amino]-1-phenylethyl]amino]-4-oxobutanoic acid,
5. [R-(R*,S*)]-4-[[2-[[3-(1H-indol-3-yl)-2-methyl-1-oxo-2-[(tricyclo[3.3.1.1$^{3,7}$- dec-2-ylsulfonyl)amino]propyl]amino]-3-phenylpropyl]amino]-4-oxobutanoic acid, 6. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid, 7. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]methylamino]-3-phenylpropyl]amino]-4-oxobutanoic acid, 8. [1R-[1α[R*(S*)],2β]] and [1S-[1α[S*(R*)],2β]-4-[[2-[[3-(1H-indol-3-yl)-2-methyl-1-oxo-2-[[[[2-(trifluoromethyl)cyclohexyl]oxy]carbonyl]amino]-propyl]amino]-3-phenylpropyl]amino]-4-oxobutanoic acid, 9. [1R-[1α[R*(S*)],2β]] and [1S-[1α[S*(R*)],2β]-4-[[2-[[3-(1H-indol-3-yl)-2-methyl-1-oxo-2-[[[[2-(trifluoromethyl)cyclohexyl] oxy]carbonyl]amino]-propyl]methylamino]-3-phenylpropyl]amino]-4-oxobutanoic acid, 10. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]methylamino]-3-phenylpropyl]amino]-4-oxobutanoic acid, 11. [1S-[1α,2β[S*(R*)],4α]]-1-(1H-indol-3-ylmethyl)1-methyl-2-oxo-2-[[2-[[1-oxo-3-(1H-tetrazol-5-yl)propyl]amino]-1-(phenylmethyl)ethyl]amino]ethyl]carbamic acid, 1,7,7-trimethylbicyclo[2.2.1]hept-2-yl ester, 12. [1S-[1α,2β[S*,R*)]-[1-(1H-indol-3-ylmethyl-1-methyl-2-oxo-2-[[2-[[1-oxo-3-(1H-tetrazol-5-yl)propyl]amino]-2-phenylethyl]amino]ethyl]carbamic acid, 1,7,7-trimethylbicyclo[2.2.1]hept-2-yl ester, 13. N-[2-methyl-N-[(tricyclo[3.3.1.1$^{3,7}$]dec-2-yloxy)carbonyl]-D-tryptophyl]-L-phenylalanylglycine, 14. N-[2-methyl-N-[(tricyclo[3.3.1.1$^{3,7}$]dec-2-yloxy)carbonyl]-D-tryptophyl]-L-phenylalanyl-β-alanine, and 15. (R)-tricyclo[3.3.1.1$^{3,7}$]dec-2-yl [1-(1H-indol-3-ylmethyl)-1-methyl-2-[methyl(2-phenylethyl)amino]-2-oxo-ethylcarbamate.

In addition preferred compounds of the instant invention are:

16. (±)-trans-2-chlorocyclohexyl [1-(1H-indol-3-ylmethyl)-1-methyl-2-oxo-[(2-phenylethyl)amino]ethyl]-carbamate, 17. 2-chorocyclohexyl [2-[[1-(hydroxymethyl)-2-phenylethyl]amino]-1-(1H-indol-3-ylmethyl)-1-methyl-2-oxoethyl]carbamate, 18. 2-[[2-[[[(2-chlorocyclohexyl)oxy]carbonyl]amino]-3-(1H-indol-3-yl)-2-methyl-1-oxopropyl]amino]-3-phenylpropyl butanedioate, 19. 2-[[2-[[[(2-methylcyclohexyl)oxy]carbonyl]amino]-3-(1H-indol-3-yl)-2-methyl-1-oxopropyl]amino]-3-phenylpropyl butanedioate, 20. (±)-tricyclo[3.3.1.1$^{3,7}$]dec-2-yl[1-(1H-indol-3-ylmethyl)-1-methyl-2-oxo-2-[(2-phenylethyl)amino]ethyl]carbamate, 21. tricyclo[3.3.1.1$^{3,7}$]dec-2-yl[2-[[1-(hydroxymethyl)-2-phenylethyl]amino]-1-(1H-indol-3-ylmethyl)methyl-2-oxoethyl]carbamate, 22. 2-[[3-(1H-indol-3-yl)-2-methyl-1-oxo-2-[(tricyclo[3.3.1.1$^{3,7}$]dec-2-yloxy)carbonyl]amino]propyl]amino]-3-phenylpropyl butanedioate, 23. 2-[[3-(1H-indol-3-yl)-2-methyl-1-oxo-2[[(tricyclo[3.3.1.1$^{3,7}$]dec-2-yloxy)carbonyl]amino]propyl]amino]-1-phenylethyl butanedioate, 24. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid, 25. [1S-[1α,2β[S*(S*)],4α]]-4-[[2-[[3-(1H-indol-3-yl)-2-methyl-1-oxo-2-[[[(1,7,7-trimethylbicyclo-2.2.1]hept-2-yl)oxy]carbonyl]amino]propyl]amino]-1-phenylethyl]amino]-4-oxobutanoic acid, 26. [R-[R*,S*-(E)]]-4-[[2-[[3-(1H-indol-3-yl)-2-methyl-1-oxo-2-[[tricyclo[3.3.1.1$^{3,7}$]dec-2-yloxy)carbonyl]amino]propyl]amino]-3-phenylpropyl]amino]-4-oxo-2-butenoic acid, 27. [R-(R*,S*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid, 28. (R)-tricyclo[3.3.1.1$^{3,7}$]dec-2-yl [1-(1H-indol-3-ylmethyl)-1-methyl-2-[methyl(2-phenylethyl)amino]-2-oxoethylcarbamate, 29. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, ethyl ester, 30. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid, ethyl ester, 31. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfinyl]acetic acid, 32. [R-[R*,R*-(E)]]-4-[[2-[[3-(1H-indol-3-yl)-2-methyl-1-oxo-2-[[(tricyclo[3.3.1.1$^{3,7}$]dec-2-yloxy)]carbonyl]amino]propyl]amino]-1-phenylethyl]amino]-4-oxo-2-butenoic acid, 33. [R-(R*,S*)]-[[2-[2-3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]thio]acetic acid, 34. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, methyl ester, (Bicyclo system is 1S-endo), 35. [1S-[1α,2β[S*[S*(E)]],4α]]-4-[[2-[[3-(1H-indol-3-yl)-2-methyl-1-oxo-2-[[[(1,7,7-trimethylbicyclo-[2.2.1]hept-2-yl)oxy]carbonyl]amino]propyl]amino]-1-phenylethyl]amino]-4-oxo-2-butenoic acid, (Bicyclo system is 1S-endo), 36. [R-(R*,R*)]-3-[[2-[[3-(1H-indol-3-yl)-2-methyl-1-oxo-3-[[(tricyclo[3.3.1.1$^{3,7}$]dec-2-yloxy)]carbonyl]amino]propyl]amino]-1-phenylethyl]amino]-3-oxopropanoic acid, 37. [R-(R*,S*)]-3-(1H-indol-3-ylmethyl)-3-methyl-4,10-dioxo-6-(phenylmethyl)-11-oxo-8-thia-2,5-diazatridecanoic acid, tricyclo[3.3.1.1$^{3,7}$]dec-2-yl or ester, 38. [R-(R*,S*)]-β-[[3-(1H-indol-3-yl)-2-methyl-1-oxo-2-[[(tricyclo[3.3.1.1$^{3,7}$]dec-2-yloxy)]carbonyl]amino]propyl]amino]benzenebutanoic acid, 39. [R-(R*,S*)[-N-[3[[3-(1H-indol-3-yl)-2-methyl-1-oxo-2-[[(tricyclo[3.3.1.1$^{3,7}$]dec-2-yl)]carbonyl]amino]propyl]amino]-4-phenylbutyl]glycine, 40. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-4-oxo-2-butenoic acid, 41. mono [R-(R*,R*)]-2-[[3-(1H-indol-3-yl)-2-methyl-1-oxo-2-[[(tricyclo[3.3.1.1$^{3,7}$]dec-2-yloxy)carbonyl]amino]-1-phenylethyl butanedioate, 42. 3-[[3-[[3-(1H-indol-3-yl)-2-methyl-1-oxo-2-[[(tricyclo[3.3.1.1$^{3,7}$]dec-2-yloxy)]carbonyl]amino]propyl]amino]-1-oxo-2-phenylprophl]amino]propanoic acid (TRP is R, other center is RS), p0 43. [1R-[1α-[R*(S*)],2β]]-4-[[2-[[3-(1H-indol-3-yl)-2-methyl-2-

44. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxobutanoic acid, (−)-Isomer, 45. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic acid, (−)-Isomer, 46. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxobutanoic aid, (−)-Isomer, 47. 2-methylcyclohexyl-[1R-[1α[R*(S*)]],2β]-2-[[1-(hydroxymethyl)-2-phenylethyl]amino]-1(1H-indol-3-ylmethyl)-1-methyl-2-oxoethyl]carbamate, 48. [R-[R*,S*-(E,E)]]-6-[[3-(1H-indol-3-yl)-2-methyl-1-oxo-2-[[(tricyclo[3.3.1.1³,⁷]dec-2-yloxy)carbonyl]amino]propyl]amino]-7-phenyl-2,4-heptadienoic acid, 49. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 50. tricyclo[3.3.1.1³,⁷]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate, 51. [R-(R*,S*)]-3-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-3-oxopropanoic acid, 52. ethyl [R-(R*,S*)]-[[2-[[2-[3-(1H-indol-3-yl)-2-methyl-1-oxo-2-[[(tricyclo[3.3.1.1³,⁷]dec-2-yloxy)-carbonyl]amino]propyl]amino]-3-phenylpropyl]thio]acetate, 53. [R-(R*,S*)]-β-[[3-(1H-indol-3-yl)-2-methyl-1-oxo-2-[[(tricyclo[3.3.1.1³,⁷]dec-2-yloxy)carbonyl]amino]propyl]amino]-4-iodo-benzenebutanoic acid, 54. [R-(R*,R*)]-2-[[3-[[3-(1H-indol-3-yl)-2-methyl-1-oxo-2-[[(1(tricyclo[[(3.3.1.1³,⁷]dec-2-yloxy)carbonyl]amino]propyl]amino]-1-phenylethoxy]acetic acid, 55. [[3-[[3-(1H-indol-3-yl)-2-methyl-1-oxo-3-[[tricyclo(3.3.1.1³,⁷]dec-2-yloxy)carbonyl]amino]propyl]amino]-1-oxo-2-phenylpropyl]amino]acetic acid (TRP center is R, other center is RS), 56. (R)-[[[2-[[3-(1H-indol-3-yl)-1-oxo-2-methyl-2-[[(tricyclo[3.3.1.1³,⁷]dec-2-yloxy)carbonyl]amino]propyl]amino]-1-phenylethylidene]amino]oxy]acetic acid, 57. [R-(R*,S*)]-β-[[3-(1H-indol-3-yl)-2-methyl-1-oxo-2-[[(tricyclo[3.3.1.1³,⁷]dec-2-yloxy)carbonyl]amino]propyl]amino]benzenebutanoic acid, 58. [R-(R*,S*)]-N-[3-[[3-(1H-indol-3-yl)-2-methyl-1-oxo-2-[[(tricyclo[3.3.1.1³,⁷]dec-2-yloxy)carbonyl]amino]propyl]amino]-4-phenylbutyl]glycine, 59. 2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropanecarboxylic acid (cyclopropane ring is trans-(±), other centers are R), 60. carbamic acid, [1-(1H-indol-3-ylmethyl)-1-methyl-2-oxo-2[[-2-[[1-oxo-3-(1H-tetrazol-5-yl)propyl]amino]-2-phenylethyl]amino]ethyl]-, tricyclo[3.3.1.1³,⁷]dec-2-yl ester, [R,(R*,S*)]-, 61. benzeneheptanoic acid, α-[[3-(1H-indol-3-yl)-2-methyl-1-oxo-2[[(tricyclo[3.3.1.1³,⁷]dec-2-yloxy)-carbonyl]amino]propyl]amino]-, [R-(R*,S*)]-, 62. methyl-(±)-β-[[(2-phenylethyl)amino]carbonyl]-1β-[[(tricyclo[3.3.1.1³,⁷]dec-2-yloxy)carbonyl]amino]-1H-indole-3-butanoate, 63. [R-(R*,S*)]-4-[[2-(1H-indol-3-yl)-2-methyl-1-oxo-2-[[tricyclo[3.3.1.1³,⁷]dec-2-yloxycarbonyl]amino]propyl]amino]-3-phenylpropyl]amino]-4-oxo-2-butenoic acid, 64. bicyclo[2.2.1]heptane-2-acetic acid, 3-[[[[2-[[1-(hydroxymethyl)-2-phenylethyl]amino]-1-(1H-indol-3-ylmethyl)-1-methyl-2-oxoethyl]amino]carbonyl]oxy]-4,7,7-trimethyl-, [1R-[1α,2β,3α[R*(S*)],4α]]-, 65. butanoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-[1R-1α[R*(R*)]2β]]-((−)-isomer, 66. 2-butenoic acid, 4-[[2-[[3-(1H-indol-3yl)-2-methyl-2-[[[(2-methyl-1-cyclohexyl)oxy]carbonyl]amino]-1-oxopropyl]amino]-1-phenylethyl]amino]-4-oxo-[1R-[1α[R*(R*)],2β]]-((−)-isomer, 67. butanoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R-[1α[R*(S*)],2β]]-((−)-isomer), and 68. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R[1α[R*(S*)],2β]]-((−)-isomer).

Additionally preferred are the compounds:

69. [[3-[[3-(1H-indol-3-yl)-2-methyl-1-oxo-2-[[tricyclo]3.3.1.1³,⁷]dec-2-yloxy)carbonyl]amino]propyl]amino]-1-oxo-2-phenylpropyl]amino]acetic acid, 70. [R-(R*,R*)]-2-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]acetic acid, 71. [1R-[1α,2β[R*(R*)]]]-2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropane carboxylic acid, 72. [1S-[1α,2β[S*(S*)]]]-2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropane carboxylic acid, 73. pR-R*,R*)]-3-[2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]propanoic acid, 74. [R-(R*,R*)]-mono 2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl butanedioic acid, 75. 3-[[3-[[3(1H-indol-3-yl)-2-methyl-1-oxo-2-[[(tricyclo[3.3.1.1³,⁷]dec-2-yloxy)carbonyl]amino] propyl]amino]-1-oxo-2-phenylpropyl]amino]propanoic acid, 76. [R-(R*,S*)]-β-[[3-(1H-indol-3-yl)-2-methyl-1-oxo-2-[[(tricyclo[3.3.1.1³,⁷]dec-2-yloxy)carbonyl]amino]propyl]amino]-4-iodobenzenebutanoic acid, 77. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-2-butenoic acid, 78. [1R-[1α[R*(S*)],2β]]-4-[[2-[[3-(1H-indol-3yl)-2-methyl-2-[[[(2-methyl-1-cyclohexyl)oxy]carbonyl]amino]-1-oxopropyl]amino]-3-phenylpropyl]amino]-4-oxobutanoic acid, ((−)-isomer, 79. [1R-[1α[R*(R*)],2β]]-4-[[2-[[3-(1H-indol-3-yl)-2-methyl-2-[[[(2-methyl-1-cyclohexyl)oxy]carbonyl- ]amino]-1-oxopropyl]amino]-1-phenylethyl]amino]-4-oxo-2-butenoic acid, 80. 1R-[1β[R*(R*)],2β]]-4-[[2-[[3-(1H-indol-3-yl)-2-methyl-2-[[[(2-methyl-1-cyclohexyl)oxy]carbonyl]amino-9 -1-oxopropyl]amino]-1-phenylethyl]amino]-4-oxobutanoic acid, ((−)-isomer, 81. [R-(R*,S*)]-1g/-[[3-(1H-indol-3-yl)-2-methyl-1-oxo-2-[[(tricyclo[3.3.1.1$^{3,7}$]dec-2-yloxy)carbonyl]amino]propyl]amino]benzeneheptanoic acid, 82. 2-[[[2-[[3-(1H-indol-3-yl)-2-methyl-1-oxo-2-[[(tricyclo[3.3.1.1$^{3,7}$]dec-2-yloxy)carbonyl ]amino]propyl]amino]-1-phenylethyl]amino]carbonyl]cyclopropanecarboxylic acid (cyclopropyl ring is trans-(±), other centers are R), 83. 2-methylcyclohexyl [1R-[1α[R*(S*)]],2β]-[[1-(hydroxymethyl)-2-phenylethyl]amino]-1-(1H-indol-3-ylmethyl)-1-methyl-2-oxoethyl]carbamate, 84. [R-[R*,S*-(E<E)][-6-[[3-(1H-indol-3-yl)-2-methyl-1-oxo-2[[(tricyclo[3.3.1.1$^{3,7}$]dec-2-yloxy)carbonyl]amino]propyl]amino]-7-phenyl-2,4-heptadienoic acid, 85. tricyclo[3.3.1.1$^{3,7}$]dec-2-yl [2-[[1-(hydroxymethyl)-2-hydroxy-2-phenylethyl]amino]-1-(1H-indol-3-ylmethyl)-1-methylethyl]carbamate, 86. tricyclo[3.3.1.1$^{3,7}$]dec-2-yl [R-(R*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamate, 87. [R-(R*,S*)]-2-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetic acid, 88. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid 89. ethyl [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetate, 90. 2-chlorocyclohexyl [2-[[1-(hydroxymethyl)-2-phenylethyl]amino]-1-(1H-indol-3-ylmethyl)-1-methyl-2-oxoethyl]carbamate.

Isomer II

Ring Centers are trans, trp center is D, other center is S, ((−) or (+) form)

91. [R-[R*,R*(E)]]-4-[[2-[[3-(1H-indol-3-yl)-2-methyl-1-oxo-2-[[(tricyclo[3.3.1.1$^{3,7}$]dec-2-ylamino)-carbonyl]amino]propyl]amino]-1-phenylethyl]amino]-4-oxo-2-butenoic acid, 92. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid, 93. [R-(R*,S*)]-mono[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]butanedioate, 94. tricyclo[3.3.1.1$^{3,7}$]dec-2-yl [R-(R*,S*)]-[2-[[1-(hydroxymethyl)-2-phenylethyl]amino]-1-(1H-indol-3-ylmethyl)-1-methyl-2-oxoethyl]carbamate, 95. [1S-[1α,2β[S*[S(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, 96. [1S-[1α,2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, (bicyclo system is 1S-endo), 97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)-carbonyl]amino]propyl]amino]-3-phenylpropyl]amino]-4-oxo-2-butenoic acid, 98. N-[2-methyl-N-[(tricyclo[3.3.1.1$^{3,7}$]dec-2-yloxy)carbonyl]-D-tryptophyl]-L-phenylalanylglycine, 99. [R-(R*,S*)[-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid, 100. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 101. [R-(R*,R*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-3-oxopropanoic acid, 102. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl] amino]propyl]amino]-3-phenylpropyl]amino]-3-oxopropanoic acid, 103. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-3-phenylpropyl]amino]-4-oxo-2-butenoic acid, 104. [R-(R*,S*)]-5-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-5-oxopentanoic acid, 105. ethyl [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]sulfinyl]acetate, 106. [R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl ]amino]propyl]amino]-1-phenylethyl]amino]-4-oxo-2-butenoic acid, 107. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-4-phenylbutyl]-β-alanine, 108. N-[N-[α-methyl-N-[(tricyclo[3.3.1.1$^{3,7}$]dec-2-yloxy)carbonyl]-D-tryotophyl]-L-phenylalanyl]-L-alanine, 109. [R-R*,S*)]-3-[[2-[[3(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]propanoic acid, 110. [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amion]-3-phenylpropyl]thio]acetic acid, 111. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid, 112. tricyclo[3.3.1.1$^{3,7}$]dec-2-yl [R-(R*,S*)]-3-(1H-indol-3-ylmethyl)-3-methyl-4,10-dioxo-6-(phenylmethyl)-11-oxa-8-thia-2,5-diazatridecanoic acid, 113. [2-[[2-hydroxy-1-(hydroxymethyl)-2-phenylethyl]amino]-1-(hydroxymethyl)-1-(1H-indol-3-ylmethyl)-2-oxoethyl]-, tricyclo[3.3.1.1$^{3,7}$]dec-2-yl ester, 114. N-[α-methyl-N-[(tricyclo[3.3.1.1$^{3,7}$]dec-2-yloxy)carbonyl]-L-tryptophyl]-D-3-(phenylmethyl)-β-alanine, 115. (1R-trans)-N-[α-methyl-N-[[(2-methylcyclohexyl)oxy]carbonyl]-L-tryptophyl]-D-3-(phenylmethyl)((1R,2R)-N-[[(2-methylcyclohexyl)oxy]carbonyl])(α/-Me)LTrp-(D-3-Bzl)bAla-β-alanine ((−)-isomer), and
116. (1S-trans)-N-[α-methyl-N-[[(2-methylcyclohexyl)oxy]carbonyl]-D-tryptophyl]-L-3-(phenylmethyl)-β-alanine.

The more preferred compound is CI-988.

The most preferred compound is the N-methylglucamine salt of CI-988.

Pharmaceutical compositions of a compound of the present invention or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma, propylene glycol, glycerin; sorbitol; polyethylene glycol; water; agar; alginic acid; isotonic saline, and phosphate buffer solutions; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primary liquid composition. The more satisfactory compositions are those in which a much higher proportion of the active ingredient is present.

Routes of administration of a subject compound or its salts are oral or parenteral. For example, a useful intravenous dose is between 100 and 800 mg and a useful oral dosage is between 200 and 800 mg.

A unit dosage form of the instant invention may also comprise other compounds useful in the therapy of depression.

A typical dose is, for example, from 600 to 2400 mg per day given in three individual doses.

A skilled physician will be able to determine the appropriate situation in which subjects are susceptible to or at risk of minor or major depression for administration by methods of the present invention.

The advantages of using the compounds of the invention are the compounds are well tolerated, are easily administered IV, are not metabolized in the body, do not cause sedation, and do not cause a withdrawal reaction. Unlike with tricyclic antidepressants, there are no cardiovascular side effects. The compounds do not potentiate the action of alcohol or of barbiturates.

Compounds useful in the method of treating depression of the instant invention are those of formula $$R^1-A-N(H)-C(R^2)(CH_2\text{-indole})-C(=O)-N(R^9)-C(R^3)(R^{12})-C(R^4)(R^{13})-Ar \quad I$$

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and $-(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is $-(CH_2)_nCO-$, $-SO_2-$, $'S(=O)-$, $-NHCO-$, $$-(CH_2)_n-OC(=O)-,$$

$-SCO-$, $-O-(CH_2)_nCO-$ or $-HC=CHCO-$ wherein n is an integer from zero to six;

$R^2$ is a straight or branched alkyl of from one to about six carbon atoms, $-HC=CH_2$, $-C\equiv CH$, $-CH_2-CH=CH_2$, $-CH_2C\equiv CH$, $-(CH_2)_nAr$, $-(CH_2)_nOR^*$, $(CH_2)_nOAr$, $-(CH_2)_nCO_2R^*$, or $-(CH_2)_nRN^5R^6$ wherein n, R*, $R^5$ and $R^6$ are as defined above and Ar is as defined below;

$R^3$ and $R^4$ are each independently selected from hydrogen, $R^2$ and $-(CH_2)_{n'}-B-D$ wherein:

n' is an integer of from zero to three;

B is a bond,
$-OCO(CH_2)_n-$,
$-O(CH_2)_n-$,
$-SO_2NH(CH_2)_n-$,
$-NHSO_2(CH_2)_n-$,
$-NHCO(CH_2)_2-$,
$-CONH(CH_2)_n-$,
$-NHCOCH=CH-$,
$-COO(CH_2)_n-$,
$-CO(CH_2)_n-$,
$-S-(CH_2)_n-$,
$-S(=O)-(CH_2)_n$,
$-SO_2-(CH_2)_n$, $-CONH-C(R^7)=C(R^8)-$, $-NHCO-C(H)(R^7)-C(H)(R^8)-$, $-NHCO-C(R^7)=C(R^8)-$, $-CONH-C(H)(R^7)-C(H)(R^8)-$, $-C(R^7)=C(R^8)-$ or $-C(H)(R^7)-C(H)(R^8)-$ wherein $R^7$ and $R^8$ are independently selected from hydrogen and $R^2$ or together form a ring $(CH_2)_m$ wherein m is an integer of from 1 to 5 and n is as defined above;

D is
—COOR*,
—CH₂OR*,
—CHR²OR*,
—CH₂SR*,
—CHR²SR*,
—CONR⁵R⁶,
—CN,
—NR⁵R⁶,
—OH,
—H and acid replacements tetrazole, and

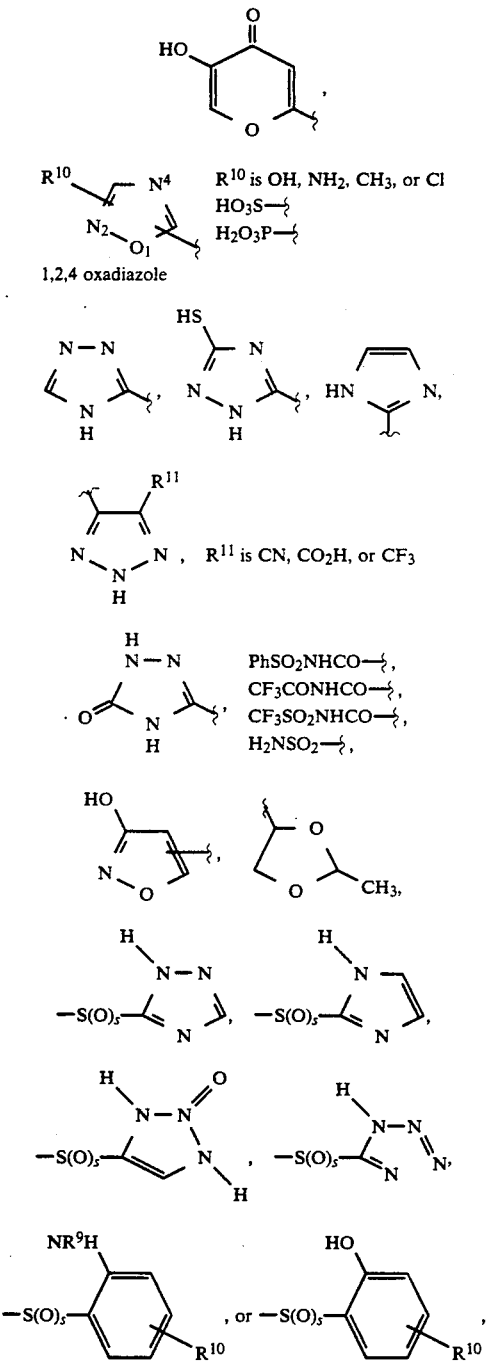

wherein R*, R², R⁵, and R⁶ are as defined above;
R⁹ is hydrogen or a straight or branched alkyl of from one to about six carbon atoms, —(CH₂)ₙCO₂R*, —(CH₂)ₙOAr', —(CH₂)ₙAr' or (CH₂)ₙNR⁵R⁶, wherein n, R*, R⁵, and R⁶ are as defined above or taken from R³ and Ar' is taken from Ar as defined below;

R¹² and R¹³ are each independently hydrogen or are each independently taken with R³ and R⁴ respectively to form a moiety double bonded to the carbon atom; and Ar is a mono- or polycyclic unsubstituted or substituted carbo- or heterocyclic aromatic or hydroaromatic moiety.

Especially useful are compounds selected from:

1. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, 2. [1S-[1α,2β[S*(S*)],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]methylamino]-1-phenylethyl]amino]-4-oxobutanoic acid, 3. [1S-[1α,2β[S*(S*)],4α]]-4-[[2-[[3-(1H-indol-3-yl-2-methyl-1-oxo-2-[[[1,7,7-trimethylbicyclo[2.2.1]hept-2-yl)amino]carbonyl]amino]propyl]amino]-1-phenylethyl]amino]-4-oxobutanoic acid, 4. [R*,R*)]-4-[[2-[[3-(1H-indol-3-yl)-2-methyl-1-oxo-2-[(tricyclo[3.3.1.1³,⁷]dec-2-ylsuflonyl)amino]propyl]amino]-1-phenylethyl]amino]-4-oxobutanoic acid, 5. [R-(R*,S*)]-4-[[2-[[3-(1H-indol-3-yl)-2-methyl-1-oxo-2-[(tricyclo[3.3.1.1³,⁷]dec-2-ylsulfonyl)amino]propyl]amino]-3-phenylpropyl]amino]-4-oxobutanoic acid, 6. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]amino]-3-phenylpropyl]amino]-4-oxobutanoic acid, 7. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]methylamino]-3-phenylpropyl]amino]-4-oxobutanoic acid, 8. [1R-[1α[R*(S*)],2β]] and [1S-[1α[S*(R*)],2β]-4-[[2-[-[3-(1H-indol-3-yl)-2-methyl-1-oxo-2-[[[[2-(trifluoromethyl)cyclohexyl]oxy]oxy]carbonyl]amino]-propyl]amino]-3-phenylpropyl]amino]-4-oxobutanoic acid, 9. [1R-[1α[R*(S*)],2β]] and [1S-[1α[S*(R*)],2β]-4-[[2-[3(1H-indol-3-yl)-2-methyl-1-oxo-2-[[[2-(trifluoromethyl)cyclohexyl]oxy]carbonyl]amino]propyl]methylamino]-3-phenylpropyl]amino]-4-oxobutanoic acid, 10. [R-(R*,S*)]-4-[[2-[[3-(1H-indol-3-yl)-2-methyl-1-oxo-2-[[(tricyclo[3.3.1.1³,⁷]dec-2-yloxy)carbonyl]amino]propyl]methylamino]-3-phenylpropyl]amino]-4-oxobutanoic acid, 11. [1S-[1α,2β[S*(R*)],4α]]-[1-(1H-indol-3-ylmethyl)-1-methyl-2-oxo-2-[[2-[[1-oxo-3-(1H-tetrazol-5-yl)-propyl] amino]-1-(phenylmethyl)ethyl]amino]ethyl]carbamic acid, 1,7,7-trimethylbicyclo[2.2.1]hept-2-yl ester, 12. [1S-[1α,2β[S*,R*)]-[1-(1H-indol-3-ylmethyl)-1-methyl-2-oxo-2-[[2-[[1-oxo-3-(1H-tetrazol-5-yl)-propyl]amino]-2-phenylethyl]amino]ethyl]carbamic acid, 1,7,7-trimethylbicyclo[2.2.1]hept-2-yl ester, 13. N-[2-methyl-N-[(tricyclo[3.3.1.1³,⁷]dec-2-yloxy)-carbonyl]-D-tryptophyl]-L-phenylalanylglycine, 14. N-[2-methyl-N-[(tricyclo[3.3.1.1³,⁷]dec-2-yloxy)-carbonyl]-D-tryptophyl]-L-phenylalanyl-β-alanine, and 15. (R)-tricyclo[3.3.1.1³,⁷]dec-2-yl [1-(1H-indol-3-ylmethyl)-1-methyl-2-[methyl(2-phenylethyl)amino]-2-oxo-ethylcarbamate.

In addition preferred compounds of the instant invention are:

16. (±)-trans-2-chlorocyclohexyl [1-(1H-indol-3-ylmethyl)-1-methyl-2-oxo-2-[2-phenylethyl)amino]ethyl]-carbamate,
17. 2-chlorocyclohexyl [2-[[1-(hydroxymethyl)-2-phenylethyl]amino]-1-(1H-indol-3-ylmethyl)-1-methyl-2-oxoethyl]carbamate,
18. 2-[[2-[[[(2-chlorocyclohexyl)oxy]carbonyl]amino]-3-(1H-indol-3-yl)-2-methyl-1-oxopropyl]amino]-3-phenylpropyl butanedioate,
19. 2-[[2-[[[(2-methylcyclohexyl)oxy]carbonyl]amino]-3-(1H-indol-3-yl)-2-methyl-1-oxopropyl]amino]-3-phenylpropyl butanedioate,
20. (±)-tricyclo[3.3.1.1³,⁷]dec-2-yl[1(1H-indol-3-ylmethyl)-1-methyl-2-oxo-2-[2-phenylethyl)amino]ethyl]carbamate,
21. tricyclo[3.3.1.1³,⁷]dec-2-yl[2-[[1-(hydroxymethyl)-2-phenylethyl]amino-9 -1-(1H-indol-3-ylmethyl)-1-methyl-2-oxoethyl]carbamate,
22. 2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl butanedioate,
23. 2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl butanedioate,
24. [R-(R*,R*)]-4-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]-4-oxobutanoic acid,
25. [1S-[1α,2β[S*,(S*)],4α]]-4-[[2-[[3-(1H-indol-3-yl)-2-methyl-1-oxo-2-[[[(1,7,7-trimethylbicyclo-2.2.1]hept-2-yl)oxy]carbonyl]amino]propyl]amino]-1-phenylethyl]amino]-4-oxobutanoic acid,
26. [R-[R*,S*-(E)]]-4-[[2-[[3-(1H-indol-3-yl)-2-methyl-1-oxo-2-[[(tricyclo[3.3.1.1³,⁷]dec-2-yloxy)-carbonyl]amino]propyl]amino]-3-phenylpropyl]amino]-4-oxo-2-butenoic acid,
27. [R-(R*,S*)]-4-[[2-[[3-(1H-indol-3-yl)-2-methyl-1-oxo-2-[[(tricyclo[3.3.1.1³,⁷]dec-2-yloxy)carbonyl]amino propyl]amino]-3-phenylpropyl]amino]-4-oxobutanoic acid,
28. (R)-tricyclo[3.3.1.1³,⁷]dec-2-yl [1-(1H-indol-3-ylmethyl)-1-methyl-2-[methyl(2-phenylethyl)amino]-2-oxoethylcarbamate,
29. [R-(R*,S*)]-[[2-[[3-(1H-indol-3-yl)-2-methyl-1-oxo-2-[[(tricyclo[3.3.1.1³,⁷]dec-2-yloxy)]carbonyl]amino]propyl]amino]-3-phenylpropyl]sulfinyl]acetic acid, ethyl ester,
30. [R-(R*,S*)]-[[2-[[3-(1H-indol-3-yl)-2-methyl-1-oxo-2-[[(tricyclo[3.3.1.1³,⁷]dec-2-yloxy)]carbonyl ]amino]propyl]amino]-3-phenylpropyl]sulfonyl]acetic acid, ethyl ester,
31. [R-(R*,S*)]-[[2-[[3-(1H-indol-3-yl)-2-methyl-1-oxo-2-[[(tricyclo[3.3.1.1³,⁷]dec-2-yloxy)]carbonyl ] amino]propyl]amino]-3-phenylpropyl]sulfinyl]acetic acid,
32. [R-[R*,R*-(E)]]-4-[[2-[[3-(1H-indol-3-yl)-2-methyl-1-oxo-2-[[(tricyclo[3.3.1.1³,⁷]dec-2-yloxy)]carbonyl]amino]propyl]amino]-1-phenylethyl]amino]-4-oxo-2-butenoic acid,
33. [R-(R*,S*)]-[[2-[[2-[[2-[3-(1H-indol-3-yl)-2-methyl-1-oxo-2-[[(tricyclo[3.3.1.1³,⁷]dec-2-yloxy)]carbonyl]amino]propyl]amino]-3-phenylpropyl]thio]acetic acid,
34. [1S-[1α,2β[S*[S*(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, methyl ester, (Bicyclo system is 1S-endo),
35. [1S-[2α,2β[S*[S*(E)]],4α[[-4-[[2-[[3(1H-indol-3-yl)-2methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, (Bicyclo system is 1S-endo),
36. [R-(R*,R*)]-3-[[2-[[3-(1H-indol-3-yl)-2-methyl-1-oxo-3-[[(tricyclo[3.3.1.1³,⁷]dec-2-yloxy)]carbonyl]amino]propyl]amino]-1-phenylethyl]amino]-3-oxopropanoic acid,
37. [R-(R*,S*)]-3-(1H-indol-3-ylmethyl)-3-methyl-4,10-dioxo-6-(phenylmethyl)-11-oxo-8-thia-2,5-diaza-tridecanoic acid, tricyclo[3.3.1.1³,⁷]dec-2-yl or ester,
38. [R-(R*,S*)]-β-[[3-(1H-indol-3-yl)-2-methyl-1-oxo-2-[[(tricyclo[3.3.1.1³,⁷]dec-2-yloxy)]carbonyl]amino]-propyl]amino]benzenebutanoic acid,
39. [R-(R*,S*)]-N-[3-[[3-(1H-indol-3-yl)-2-methyl-1-oxo-2-[[(tricyclo[3.3.1.1³,⁷]dec-2-yloxy)]carbonyl]amino]propyl]amino]-4-phenylbutyl]glycine,
40. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-4-oxo-2-butenoic acid,
41. mono [R-(R*,R*)]-2-[[3-(1H-indol-3-yl)-2-methyl-1-oxo-2-[[(tricyclo[3.3.1.1³,⁷]dec-2-yloxy)carbonyl]amino]-1-phenylethyl butanedioate,
42. 3-[[3-[[3-(1H-indol-3-yl)-2-methyl-1-oxo-2-[[(tricyclo[3.3.1.1³,⁷]dec-2-yloxy)]carbonyl]amino]propyl]amino]-1-oxo-2-phenylprophl]amino]propanoic acid (TRP is R, other center is RS),
43. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-2-butenoic acid, (—)-Isomer,
44. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxobutanoic acid, (—)-Isomer,
45. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic acid, (—)-Isomer,
46. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxobutanoic acid, (—)-Isomer,
47. 2-methylcyclohexyl-[1R-[1α[R*(S*)]],2β]-2-[[1-(hydroxymethyl)-2-phenylethyl]amino]-1-(1H-indol-3-ylmethyl)-1-methyl-2-oxoethyl]carbamate,
48. [R-[R*,S*-(E,E)]]-6-[[3-(1H-indol-3-yl)-2-methyl-1-oxo-2-[[(tricyclo[3.3.1.1³,⁷]dec-2-yloxy)carbonyl]amino]propyl]amino]-7-phenyl-2,4-heptadienoic acid,
49. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid,
50. tricyclo[3.3.1.1³,⁷]dec-2-yl-[S-[R*,S*-(E)]]-12-(1H-indol-3-ylmethyl)-12-methyl-3,11-dioxo-9-(phenylmethyl)-2-oxa-7,10,13-triazatetradec-4-en-14-oate,
51. [R-(R*,S*)]-3-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-3-oxopropanoic acid, 52. ethyl [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]acetate, 53. [R-(R*,S*)]-β-[[3-(1H-indol-3-yl)-2-methyl-1-oxo-2-[[tricyclo[3.3.1.1$^{3,7}$]dec-2-yloxy)carbonyl]amino]propyl]amino]-4-iodo-benzenebutanoic acid, 54. [R-(R*,R*)]-[2-[[3-(1H-indol-3-yl)-2-methyl-1-oxo-2-[[(1(tricyclo[[(3.3.1.1$^{3,7}$]dec-2-yloxy)carbonyl]amino]propyl]amino]-1-phenylethoxy]acetic acid, 55. [[3-[[3-(1H-indol-3-yl)-2-methyl-1-oxo-3-[[tricyclo(3.3.1.1$^{3,7}$]dec-2-yloxy)carbonyl]amino]propyl]amino]-1-oxo-2-phenylpropyl]amino]acetic acid (TRP center is R, other center is RS), 56. (R)-[[[2-[[3-(1H-indol-3-yl)-1-oxo-2-methyl-2-[[(tricyclo[3.3.1.1$^{3,7}$]dec-2-yloxy)carbonyl]amino]propyl]amino]-1-phenylethylidene]amino]oxy]acetic acid, 57. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid, 58. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]amino]propyl]amino]-4-phenylbutyl]glycine, 59. 2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropanecarboxylic acid (cyclopropane ring is trans-(±), other centers are R), 60. carbamic acid, [1-(1H-indol-3-ylmethyl)-1-methyl-2-oxo-2-[[2-[[1-oxo-3-(1H-tetrazol-5-yl)propyl]amino]-2-phenylethyl]amino]ethyl]-, tricyclo[3.3.1.1$^{3,7}$]dec-2-yl ester, [R,(R*,S*)]-, 61. benzeneheptanoic acid, α-[[3-(1H-indol-3-yl)-2-methyl-1-oxo-2-[[(tricyclo[3.3.1.1$^{3,7}$]dec-2-yloxy)carbonyl]amino]propyl]amino]-,[R-(R*,S*)]-, 62. methyl-(±)-β-[[(2-phenylethyl)amino]carbonyl]-1β-[[(tricyclo[3.3.1.1$^{3,7}$]dec-2-yloxy)carbonyl]amino]-1H-indole-3-butanoate, 63. [R-(R*,S*)]-4-[[2-(1H-indol-3-yl)-2-methyl-1-oxo-2-[[tricyclo[3.3.1.1$^{3,7}$]dec-2-yloxycarbonyl]amino]propyl]amino]-3-phenylpropyl]amino]-4-oxo-2-butenoic acid, 64. bicyclo[2.2.1]heptane-2-acetic acid, 3-[[[[2-[[1-(hydroxymethyl)-2-phenylethyl]amino]-1-(1H-indol-3-ylmethyl)-1-methyl-2-oxoethyl]amino]carbonyl]oxy]-4,7,7-trimethyl-, [1R-[1α,2β,3α[R*(S*)],4α]]-, 65. butanoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-[1R-1α[R*(R*)]2β]]-((−)-isomer), 66. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-, 1R-[1α[R*(R*)],2β]]-((−)-isomer), 67. butanoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-[1R-[1α[R*(S*)],2β]]-((−)-isomer), and 68. 2-butenoic acid, 4-[[2-[[3-(1H-indol-3-yl)-2-methyl-2-[[[(2-methyl-1-cyclohexyl)oxy]carbonyl] amino]-1-oxopropyl]amino]-3-phenylpropyl]amino]-4-oxo-[1R[1α[R*(S*)],2β]]-((−)-isomer).

Additionally preferred are the compounds:
69. [[3-[[3-(1H-indol-1-3-yl)-2-methyl-1-oxo-2-[[tricyclo[3.3.1.1$^{3,7}$]dec-2-yloxy)carbonyl]amino]propyl]amino]-I-oxo-2-phenylpropyl]amino]acetic acid, 70. [R-(R*,R*)]-2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethoxy]acetic acid, 71. [1R-[1α,2α[R*(R*)]]]-2-[[[2-[[3-(1H-indol-3-yl)2-methyl-1-oxo-2-[[(tricyclo[3.3.1.1$^{3,7}$]dec-2-yloxy)carbonyl]amino]propyl]amino]-1-phenylethyl]amino]carbonyl]cyclopropane carboxylic acid, 72. [1S-[1α,262 [S*(S*)]]]-2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropane carboxylic acid, 73. pR-R*,R*)]-3-[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethoxy]propanoic acid, 74. [R-(R*,R*)]-mono 2-[[3-(1H-indol-3-yl)-2-methyl-1-oxo-2-[[(tricyclo[3.3.1.1$^{3,7}$]dec-2-yloxy)carbonyl]amino]-1-phenylethyl butanedioic acid, 75. 3-[[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-2-phenylpropyl]amino]propanoic acid, 76. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]-4-iodobenzenebutanoic acid, 77. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxo-2-butenoic acid, 78. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxobutanoic acid, ((−)-isomer), 79. [1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic acid, 80. 1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxobutanoic acid, ((−)-isomer), 81. [R-(R*,S*)]-1g/-[[3-(1H-indol-3-yl)-2-methyl-1oxo-2-[[(tricyclo[3.3.1.1$^{3,7}$]dec-2-yloxy)carbonyl]amino]propyl]amino]benzeneheptanoic acid, 82. 2-[[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]carbonyl]cyclopropanecarboxylic acid (cyclopropyl ring is trans-(±), other centers are R), 83. 2-methylcyclohexyl [1R-[1α[R*(S*)]],2β]]-[[1-(hydroxymethyl)-2-phenylethyl]amino]-1-(1H-indol-3-ylmethyl)-1-methyl-2-oxoethyl]carbamate, 84. [R-[R*,S*-(E<E)][[-6-[[3-(1H-indol-3-yl)-2-methyl-1-oxo-2-[[(tricyclo[3.3.1.1$^{3,7}$]dec-2-yloxy)carbonyl]amino]propyl]amino]-7-phenyl-2,4-heptadienoic acid, 85. tricyclo[3.3.1.1$^{3,7}$]dec-2-yl [2-[[1-(hydroxymethyl)-2-hydroxy-2-phenylethyl]amino]-1-(1H-indol-3-ylmethyl)-1-methylethyl]carbamate, 86. tricyclo[3.3.1.1$^{3,7}$]dec-2-yl [R-(R*,R*)]-[1-(1H-indol-3-ylmethyl)-1-methyl-2-oxo-2-[[2-[[1-oxo-3-(1H-tetrazol-5-yl)propyl]amino]-2-phenylethyl]amino]ethyl]carbamate, 87. [R-(R*,S*)]-2-[[2-[[3-(1H-indol-3-yl)-2-methyl-1-oxo-2-[[(tricyclo[3.3.1.1$^{3,7}$]dec-2-yloxy)carbonyl] amino]propyl]amino]-3-phenylpropyl]sulfinyl]acetic acid, 88. [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetic acid, 89. ethyl [R-(R*,S*)]-[[2-[[3-(1H-indol-3-yl)-2-methyl-1-oxo-2-[[(tricyclo[3.3.1.1$^{3,7}$]dec-2-yloxy)]carbonyl]amino]propyl]amino]-3-phenylpropyl]sulfonyl]acetate, 90. 2-chlorocyclohexyl [2-[[1-(hydroxymethyl)-2-phenylethyl]amino]-1-(1H-indol-3-ylmethyl)-1-methyl-2-oxoethyl]carbamate.

91. [R-[R*,R*(E)]]-4-[[2-[[3-(1H-indol-3-yl)-2-methyl-1-oxo-2-[[(tricyclo[3.3.1.1$^{3,7}$]dec-2-ylamino)carbonyl]amino]propyl]amino]-1-phenylethyl]amino]-4-oxo-2-butenoic acid, 92. [R-(R*,R*)]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxobutanoic acid, 93. [R-(R*,S*)]-mono[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]butanedioate, 94. tricyclo[3.3.1.1$^{3,7}$]dec-2-yl [R-(R*,S*)-[2-[[1-(hydroxymethyl)-2-phenylethyl]amino]-1-(1H-indol-3-ylmethyl)-1-methyl-2-oxoethyl]carbamate, 95. [1S-[1α,2β[S*[S(E)]],4α]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, 96. [1S-[1α,2β[S*(S*)],4α]]-4-[[2-[[3-(1H-indol-3-yl)-2-methyl-1-oxo-[[[(1,7,7-trimethylbicyclo[2.2.1]hept-2-yl)oxy]carbonyl]amino]propyl]amino]-1-phenylethyl] amino]-4-oxo-2-butenoic acid, (bicyclo system is 1S-endo), 97. [R-[R*,S*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxo-2-butenoic acid, 98. N-[2-methyl-N-[(tricyclo[3.3.1.1$^{3,7}$]dec-2-yloxy)carbonyl]-D-tryptophyl]-L-phenylalanylglycine, 99. [R-(R*,S*)[-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-4-oxobutanoic acid, 100. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 101. [R-(R*,R*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-3-oxopropanoic acid, 102. [R-(R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-3-oxopropanoic acid, 103. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-3-phenylpropyl]amino]-4-oxo-2-butenoic acid, 104. [R-(R*,S*)]-5-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]amino]-5-oxopentanoic acid, 105. ethyl [R-(R*,S*)]-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]-sulfinyl]acetate, 106. [R-[R*,R*-(E)]]-4-[[2-[[3-(1H-indol-3-yl)-2-methyl-1-oxo-2-[[(tricyclo[3.3.1.1$^{3,7}$]dec-2-yloxy)carbonyl]amino]propyl]amino]-1-phenylethyl]amino]-4-oxo-2-butenoic acid, 107. [R-(R*,S*)]-N-[3-[[3-(1H-indol-3-yl)-2-methyl-1-oxo-2-[[(tricyclo[3.3.1.1$^{3,7}$]dec-2-yloxy)carbonyl]amino]propyl]amino]-1-oxo-4-phenylbutyl]-β-alanine, 108. N-[N-[α-methyl-N-[(tricyclo[3.3.1.1$^{3,7}$]dec-2-yloxy)carbonyl]-D-tryotophyl]-L-phenylalanyl]-L-alanine, 109. [R-R*,S*)]-3-[[2-[[3-(1H-indol-3-yl)-2-methyl-1-oxo-2-[[(tricyclo[3.3.1.1$^{3,7}$]dec-2-yloxy)carbonyl]amino]propyl]amino]-3-phenylpropyl]thio]-propanoic acid, 110. [R-(R*,S*)]-[[2-[[2-[3-(1H-indol-3-yl)-2-methyl-1-oxo-2-[[(tricyclo[3.3.1.1$^{3,7}$]dec-2-yloxy)carbonyl]amino]propyl]amion]-3-phenylpropyl]thio]acetic acid, 111. [R-(R*,S*)]-β-[[3-(1H-indol-3-yl)-2-methyl-1-oxo-2-[[(tricyclo[3.3.1.1$^{3,7}$]dec-2-yloxy)carbonyl]amino]propyl]amino]benzenebutanoic acid, 112. tricyclo[3.3.1.1$^{3,7}$]dec-2-yl [R-(R*,S*)]-3-(1H-indol-3-ylmethyl)-3-methyl-4,10-dioxo-6-(phenylmethyl)-11-oxa-8-thia-2,5-diazatridecanoic acid, 113. [2-[[2-hydroxy-1-(hydroxymethyl)-2-phenylethyl]amino]-1-(hydroxymethyl)-1-(1H-indol-3-ylmethyl)-2-oxoethyl]-, tricyclo[3.3.1.1$^{3,7}$]dec-2-yl ester, 214. N-[α-methyl-N-[(tricyclo[3.3.1.1$^{3,7}$]dec-2-yloxy)carbonyl]-L-tryptophyl]-D-3-(phenylmethyl)-β-alanine, 115. (1R-trans)-N-[α-methyl-N-[[(2-methylcyclohexyl)oxy]carbonyl]-L-tryptophyl]-D-3-(phenylmethyl)((1R,2R)-N-[[(2-methylcyclohexyl)oxy]carbonyl])(α-Me)LTrp-(D-3-Bzl)bAla-β-alanine ((−)-isomer), and 116. (1S-trans)-N-[ -methyl-N-[[(2-methylcyclohexyl)oxy]carbonyl]-D-tryptophyl]-L-3-(phenylmethyl)-β-alanine.

Other compounds useful in the method of treating depression of the instant invention are those of formula

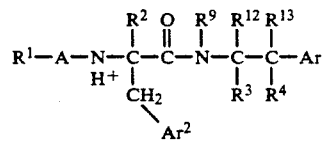

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and —$(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from-zero to six;

A is —$(CH_2)_nCO$—, —$SO_2$—, —$S(=O)$—, —NHCO—,

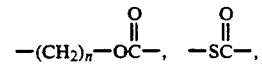

—O—(CH$_2$)$_n$CO—, or —HC=CHCO— wherein n is an integer from zero to six;

R$^2$ is a straight or branched alkyl of from one to about six carbon atoms, —HC=CH$_2$, —C≡CH, —(CH$_2$)$_n$—CH=CH$_2$, —(CH$_2$)$_n$C≡CH, —(CH$_2$)$_n$Ar, —(CH$_2$)$_n$OR*, —(CH$_2$)$_n$OAr, —(CH$_2$)$_n$CO$_2$R*, or —(CH$_2$)$_n$NR$^5$R$^6$ wherein n, R*, R$^5$, and R$^6$ are as defined above and Ar is as defined below;

R$^3$ and R$^4$ are each independently selected from hydrogen, R$^2$ and —(CH$_2$)$_{n'}$—B—D wherein:

n' is an integer of from zero to three;

B is a bond,
—OCO(CH$_2$)$_n$—,
—O(CH$_2$)$_n$—,
—NHCO(CH$_2$)$_n$—,
—CONH(CH$_2$)$_n$—,
—NHCOCH=CH—,
—COO(CH$_2$)$_n$—,
—CO(CH$_2$)$_n$—,
—S—(CH$_2$)$_n$—,
—S(=O)—(CH$_2$)$_n$—,
—SO$_2$—(CH$_2$)$_n$—,
—NHSO$_2$-(CH$_2$)$_n$—,
SO$_2$NH(CH$_2$)$_n$—,

NHCO—C=C—,
           |    |
           R$^7$ R$^8$

CONH—C=C—,
           |    |
           R$^7$ R$^8$

H  H
       |    |
NHCO—C—C—,
       |    |
       R$^7$ R$^8$

H  H
       |    |
CONH—C—C—
       |    |
       R$^7$ R$^8$ wherein R$^7$ or R$^8$ are independently selected from hydrogen and R$^2$ or together form a ring (CH$_2$)m wherein m is an integer of from 1 to 5 and n is as defined D is
—COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H and acid replacements such as tetrazole

[tetrazole structure]

[1,2,4 oxadiazole structure]

R$^{10}$ is OH, NH$_2$, CH$_3$ or Cl
HO$_3$S—⅃
⅂—PO$_3$H$_2$

[various heterocyclic structures]

R$^{11}$ is CN, CO$_2$H, or CF$_3$,

PhSO$_2$NHCO—⅃, CF$_3$CONHCO—⅃,

CF$_3$SO$_2$NHCO—⅃, H$_2$NSO$_2$—⅃,

[additional heterocyclic structures with —S(O)$_m$— substituents]

[substituted phenyl structures with NR$^5$H and HO groups]

wherein m is an integer of from 0 to 2, wherein R*, R$^2$, R$^5$, and R$^6$ are as defined above;

R$^9$ is hydrogen or a straight or branched alkyl of from one to about six carbon atoms, —(CH$_2$)$_n$CO$_2$R*, —(CH$_2$)$_n$OAr', —(CH$_2$)$_n$NR$^5$R$^6$, wherein n, R*, R$^5$, and R$^6$ are as defined above or taken from R$^3$ and Ar' is taken from Ar as defined below;

R$^{12}$ and R$^{13}$ are each independently hydrogen or are each independently taken with R$^3$ and R$^4$, respectively, to form a moiety doubly bonded to the carbon atom;

Ar is a mono- or polycyclic unsubstituted or substituted carbo- or heteroaromatic or carbo- or heterohydroaromatic moiety; and Ar$^2$ can be selected from Ar as defined above or the CH$_2$Ar$^2$ moiety of formula I is the sidechain of a biologically significant amino acid, with the proviso that Ar$^2$ cannot be

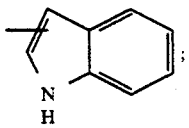

Ar² is also —(CH₂)₂NHC(=NH)NHNO₂, —(CH₂)₂NMe₂, or —CH₂CO₂CH₃.

Especially useful are compounds selected from

Tricyclo[3.3.1.1³,⁷]dec-2-yl[2-[[1-(hydroxymethyl)-2-phenylethyl]amino]-1-methyl-2-oxo-1-(9H-pyrido[3,4-b]indol-3-ylmethyl)ethyl]-carbamate (alanine center is RS, other center is S), Tricyclo[3.3.1.1³,⁷]dec-2-yl[1-methyl-1-[[9-(methylsulfonyl)-9H-pyrido[3,4-b]indol-3-yl]methyl]-2-oxo-2-[(2-phenylethyl)amino]ethyl]-carbamate, Tricyclo[3.3.1.1³,⁷]dec-2-yl[2-[[1-(hydroxymethyl)-2-phenylethyl]amino]-1-methyl-1-[[9-(methylsulfonyl)-9H-pyrido[3,4-b]indol-3-yl]methyl]-2-oxoethyl]carbamate (phenylmethyl center S, other center RS), Tricyclo[3.3.1.1³,⁷]dec-2-yl[2-[[1-(hydroxymethyl)-2-phenylethyl]amino]-1-methyl-1-(1-naphthalenylmethyl)-2-oxoethyl]carbamate (naphthalenylmethyl center is RS, other center is S), Tricyclo[3.3.1.1³,⁷]dec-2-yl[2-[[1-hydroxymethyl)-2-phenylethyl]amino]-1-methyl-1-(2-naphthalenylmethyl)-2-oxoethyl]carbamate (naphthalene center is RS, hydroxymethyl center is S), Tricyclo[3.3.1.1³,⁷]dec-2-yl(±)-[1-methyl-1-(1-naphthalenylmethyl)-2-oxo-2-[(2-phenylethyl)amino]ethyl]carbamate, Tricyclo[3.3.1.1³,⁷]dec-2-yl(±)-[1-methyl-1-(2-naphthalenylmethyl)-2-oxo-2-[(2-phenylethyl)amino]ethyl]carbamate, Tricyclo[3.3.1.1³,⁷]dec-2-yl[2-[[1-(hydroxymethyl)-2-phenylethyl]amino]-1-methyl-1-(2-naphthalenylmethyl)-2-oxoethyl]carbamate (hydroxy center is S, other center is R or S) (Isomer I), Tricyclo[3.3.1.1³,⁷]dec-2-yl(±)[1-(3-benzofuranylmethyl)-1-methyl-2-oxo-2-[(2-phenylethyl)amino]ethyl]-carbamate, Tricyclo[3.3.1.1³,⁷]dec-2-yl[1-(3-benzofuranylmethyl)-2-[[1-(hydroxymethyl)-2-phenylethyl]amino]-1-methyl-2-oxoethyl[carbamate (benzofuranylmethyl center is RS, other center is S), Tricyclo[3.3.1.1³,⁷]dec-2-yl[1-[(2-bromo-3-benzofuranyl)methyl]-2-[[1-(hydroxymethyl)-2-phenylethyl]amino]-1-methyl-2-oxoethyl]carbamate (benzofuran center is RS, hydroxymethyl center is S), Tricyclo[3.3.1.1³,⁷]dec-2-yl(±)-[1-[(2-bromo-3-benzofuranyl)methyl]-1-methyl-2-oxo-2-[(2-phenylethyl)amino]ethyl]carbamate, 2-Methylpropyl 2-[[2-methyl-1-oxo-3-(3-pyridinyl)-2-[[(tricyclo[3.3.1.1³,⁷]dec-2-yloxy)carbonyl]amino]-propyl]amino]-3-phenylpropyl carbonate (pyridine center is RS, other center is S), Tricyclo[3.3.1.1³,⁷]dec-2-yl[2-[[1-hydroxymethyl)-2-phenylethyl]amino]-1-methyl-2-oxo-1-(3-pyridinylmethyl)ethyl]carbamate (hydroxymethyl center is S, other is (±)) (Diastereomer I), Tricyclo[3.3.1.1³,⁷]dec-2-yl(±)-[1-methyl-2-oxo-2-[(2-phenylethyl)amino]-1-(4-pyridinylmethyl)ethyl]carbamate, Tricyclo[3.3.1.1³,⁷]dec-2-yl [2-[[1-(hydroxymethyl)-2-phenylethyl]amino]-1-methyl-2-oxo-1-(2-pyridinylmethyl)ethyl]carbamate (hydroxymethyl center is S, other center is R or S) (Diastereomer I), Tricyclo[3.3.1.1³,⁷]dec-2-yl(±)-[1-methyl-2-oxo-2-[(2-phenylethyl)amino]-1-(2-pyridinyl)methyl)ethyl]carbamate, Tricyclo[3.3.1.1³,⁷]dec-2-yl(±)-[1-[(2-aminophenyl)methyl]-1-methyl-2-oxo-2-[(2-phenylethyl)amino]ethyl]-carbamate, Tricyclo[3.3.1.1³,⁷]dec-2-yl(±)-[1-[(2-hydroxyphenyl)-methyl]-1-methyl-2-oxo-2-[(2-phenylethyl)amino]ethyl]carbamate, Tricyclo[3.3.1.1³,⁷]dec-2-yl(±)-[1-methyl-2-oxo-2-[(2-phenylethyl)amino]-1-[(2-quinolinyl)methyl]ethyl]-carbamate, Tricyclo[3.3.1.1³,⁷]dec-2-yl[2-[[1-(hydroxymethyl)-2-phenylethyl]amino]-1-methyl-2-oxo-1-(4-quinolinylmethyl)ethyl]carbamate (hydroxymethyl center is S, other center is RS), Tricyclo[3.3.1.1³,⁷]dec-2-yl)(±)-[1-methyl-2-oxo-2-[(2-phenylethyl)-amino]-1-(4-quinolinylmethyl)ethyl]-carbamic acid, Tricyclo[3.3.1.1³,⁷]dec-2-yl(±)-[1-methyl-2-oxo-2-(2-phenylmethyl)amino]-1-(3-quinolinyl-methyl)ethyl]-carbamate, Tricyclo[3.3.1.1³,⁷]dec-2-yl[2-[[1-(hydroxymethyl)-2-phenylethyl]amino]-1-methyl-2-oxo-1-(2-quinolinylmethyl)ethyl[carbamate (alanine center is RS, other center is S), Tricyclo[3.3.1.1³,⁷]dec-2-yl [2-[(2-amino-2-phenylethyl)amino]-1-(1H-indazol-3-ylmethyl)-1-methyl-2-oxoethyl]carbamate, 4-[[2-[[2-methyl-1-oxo-3-(1,2,3,4-tetrahydro-2-quinolinyl)-2-[[(tricyclo[3.3.1.1³,⁷]dec-2-yloxy)carbonyl]amino]propyl]amino]-1-phenylethyl]-amino]-4-oxobutanoic acid compd. with 1-deoxy-1-(methylamino)-D-glucitol, 4-[[2-[[3-(1,2-dihydro-2-quinolinyl)-2-methyl-1-oxo-2-[[(tricyclo[3.3.1.1³,⁷]dec-2-yloxy)carbonyl]amino]-propyl]amino]-1-phenylethyl]amino]-4-oxobutanoic acid compd. with 1-deoxy-1-(methylamino)-D-glucitol, 4-[[2-[[2-methyl-1-oxo-3-(4-quinolinyl)-2-[[(tricyclo[3.3.1.1³,⁷]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1³,⁷]dec-2-yl(±)-[1-(1H-indazol-3-ylmethyl)-1-methyl-2-oxo-2-[(2-phenylethyl)amino]ethyl]-carbamate, Tricyclo[3.3.1.1³,⁷]dec-2-yl[2-[[1-(hydroxymethyl)-2-phenylethyl]amino]-1-(1H-indazol-3-ylmethyl)-1-methyl-2-oxoethyl]carbamate (hydroxymethyl center is S, other center is RS), 4-[[2-[3-(1H-indazol-3-yl)-2-methyl-1-oxo-2-[[(tricyclo[3.3.1.1³,⁷]dec-2-yloxy)carbonyl]amino]propyl]amino]-1-phenylethyl]amino]-4-oxobutanoic acid (mixture of isomers), Tricyclo[3.3.1.1³,⁷]dec-2-yl(±)-1-[1-(1H-benzimidazol-2-ylmethyl)-1-methyl-2-oxo-2-[(2-phenylethyl)amino]ethyl]carbamate, Tricyclo[3.3.1.1³,⁷]dec-2-yl[1-(1H-benzimidazol-2-ylmethyl)-2-[[1-(hydroxymethyl)-2-phenylethyl]amino]-1-methyl-2-oxoethyl]carbamate (hydroxy center is S, other center is RS), Tricyclo[3.3.1.1³,⁷]dec-2-yl[1-(benzo[b]thien-3-ylmethyl)-2-[[1-(hydroxymethyl)-2-phenylethyl]amino]-1-methyl-2-oxoethyl]-carbamate (benzothiophene center is RS, hydroxymethyl center is S), Tricyclo[3.3.1.1³,⁷]dec-2-yl(±)-[1-(benzo[b]thien-3-ylmethyl)-1-methyl-2-oxo-2-[(2-phenylethyl)amino]ethyl]carbamate, Tricyclo[3.3.1.1³,⁷]dec-2-yl-(R or S,R)-[2-[[2-(2,5-dioxo-1-pyrrolidinyl)-2-phenylethyl]amino]-1-(1H-indazol-3-ylmethyl)-1-methyl-2-oxoethyl]carbamate, Tricyclo[3.3.1.1³,⁷]dec-2-yl-(S or R,R)-[2-[[2-(2,5-dioxo-1-pyrrolidinyl)-2-phenylethyl]amino]-1-(1H-indazol-3-ylmethyl)-1-methyl-2-oxoethyl]carbamate, Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate, Tricyclo[3.3.1.1³,⁷]dec-2-yl [2-[[2-hydroxy-1-(hydroxymethyl)-2-phenylethyl]amino]-1-[(4-hydroxyphenyl)methyl]-1-methyl-2-oxoethyl]carbamate (Mixture of [1S-[1R*(R*),2R*]] and [1S-[1R*(S*),2R*]] isomers), Tricyclo[3.3.1.1³,⁷]dec-2-yl [2-[[2-hydroxy-1-(hydroxymethyl)-2-phenylethyl]amino]-1-[(4-methoxyphenyl)methyl]-1-methyl-2-oxoethyl]carbamate (Mixture of [1S-[1R*(R*),2R*]] and [1S-[1R*(S*),2R*]] isomers), Tricyclo[3.3.1.1³,⁷]dec-1-yl [2-[[2-hydroxy-1-(hydroxymethyl)-2-phenylethyl]amino]-1-methyl-2-oxo-1-[[4-(phenylmethoxy)phenyl]methyl]ethyl]carbamate (Mixture of [1S-[1R*(R*),2R*]] and [1S-[1R*(S*),2R*]] isomers), Tricyclo[3.3.1.1³,⁷]dec-2-yl (±)-[1-[(3,5-dimethyl-4-isoxazolyl)methyl]-1-methyl-2-oxo-2-[(2-phenylethyl)amino]ethyl]carbamate, Tricyclo[3.3.1.1³,⁷]dec-2-yl (±)-[1-[[2-(acetylamino)-4-thiazolyl]methyl]-1-methyl-2-oxo-2-[(2-phenylethyl)amino]ethyl]carbamate, Tricyclo[3.3.1.1³,⁷]dec-2-yl (±)-[1-(1H-benzotriazol-1-ylmethyl)-1-methyl-2-oxo-2-[(2-phenylethyl)amino]ethyl]carbamate, Tricyclo[3.3.1.1³,⁷]dec-2-yl (RS,S) [2-[[1-(hydroxymethyl)-2-phenylethyl]amino]-1-methyl-2-oxo-1-[[4-(1,2,3-thiadiazol-4-yl)phenyl]methyl]ethyl]carbamate, Tricyclo[3.3.1.1³,⁷]dec-2-yl (S or R, S)-[2-[[2-hydroxy-1-(hydroxymethyl)-2-phenylethyl]amino]-1-methyl-2-oxo-1-[[4-(1,2,3-thiadiazol-4-yl)phenyl]methyl]ethyl]carbamate, Tricyclo[3.3.1.1³,⁷]dec-2-yl-(S or R,R)-[2-[[2-(2,5-dioxo-1-pyrrolidinyl)-2-phenylethyl]amino]-1-(1H-indazol-3-ylmethyl)-1-methyl-2-oxoethyl]carbamate, 4-[[2-[[2-Methyl-1-oxo-3-(4-pyridinyl)-2-[[(tricyclo[3.3.1.1³,⁷]dec-2-yloxy)carbonyl]amino]propyl]amino]-1-phenylethyl]amino]-4-oxobutanoic acid, 4-[[2-[[3-(2,3-dihydro-1-methyl-5-phenyl-1H-benzodiazepin-2-yl)-2-methyl-1-oxo-2-[[(tricyclo-[3.3.1.1³,⁷]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1³,⁷]dec-2-yl [2-[[1-(hydroxymethyl)-2-phenylethyl]amino]-1-methyl-2-oxo-1-(2-pyridinylmethyl)ethyl]carbamate, N-oxide, Tricyclo[3.3.1.1³,⁷]dec-2-yl [1-[(2,3-dihydro-1-methyl-5-phenyl-1H-1,4-benzodiazepin-2-yl)methyl]-1-methyl-2-[(2-phenylethyl)amino]-2-oxoethyl]carbamate, Tricyclo[3.3.1.1³,⁷]dec-2-yl [2-[[1-hydroxymethyl)-2-phenylethyl]amino]-1-methyl-2-oxo-1-(4-pyridinylmethyl)ethyl]carbamate, Tricyclo[3.3.1.1³,⁷]dec-2-yl (±)-[1-methyl-2-oxo-2-[(2-phenylethyl)amino]-1-[(5,6,7,8-tetrahydro-5,5,8,8-tetramethyl-2-naphthalenyl)methyl]ethyl]carbamate, Tricyclo[3.3.1.1³,⁷]dec-2-yl [1S-[1R*(R or S),2R*]]-[2-[[2-hydroxy-1-(hydroxymethyl)-2-phenylethyl]amino]-1-methyl-2-oxo-1-(1H-pyrrolo[2,3-b]pyridin-3-ylmethyl)ethyl]carbamate, Tricyclo[3.3.1.1³,⁷][1S-[1R*(S or R),2R*]]-[2-[[2-hydroxy-1-(hydroxymethyl)-2-phenylethyl]amino]-1-methyl-2-oxo-1-(1H-pyrrolo[2,3-b]pyridin-3-ylmethyl)ethyl]carbamate, Tricyclo[3.3.1.1³,⁷]dec-2-yl [1S-[1R*(R or S),2R*]]-[2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate, Tricyclo[3.3.1.13,7] [1S-[1R*(S or R),2R*]]-[2-methyl-2-oxo-1-(1H-pyrrolo[3,2-c]pyridin-3-ylmethyl)ethyl]carbamate, Carbamic acid, [-[(2,3-dimethyl)-1H-pyrrol-4-ylmethyl]-1-methyl-2-oxo-2[(2-phenylethyl)amino]amino]ethyl-, tricyclo[3.3.1.1³,⁷]dec-2-yl ester, Carbamic acid, [1-[(2,3-dimethyl)-1H-pyrrol-4-ylmethyl]-2-[[1-(hydroxymethyl)-2-hydroxy-2-phenylethyl] amino]-1-methylethyl]-, tricyclo[3.3.1.1³,⁷]dec-2-yl ester (mixture of isomers), Carbamic acid, [1-(imidazo[1,5-a]pyridin-3-ylmethyl)-2-oxo-2-[(2-phenylethyl)amino]ethyl]-, tricyclo[3.3.1.1³,⁷]dec-2-yl ester, and Carbamic acid, [2-[[1-(hydroxymethyl)-2-hydroxy-2-phenylethyl]amino]-1-(imidazo[1,5-a]pyridin-3-ylmethyl)-1-methylethyl]-, tricyclo[3.3.1.1³,⁷]dec-2-yl ester (mixture of isomers).

Other compounds useful in the method of treating depression of the instant invention are those of formula

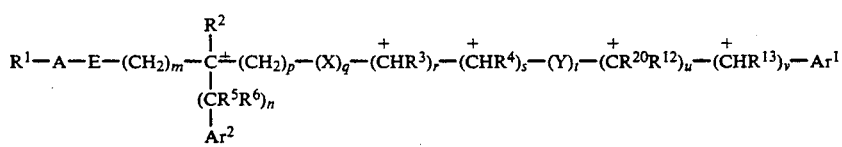

III or a pharmaceutically acceptable salt thereof wherein:
R¹ is a cyclo or polycycloalkyl hydrocarbon or mono- or polyheterocyclic moiety wherein the hetero atom(s) can be N, O, and/or S, of from 3 to 12 carbon atoms with from 0 to 4 substituents each independently selected from a straight or branched alkyl of from 1 to 6 carbon atoms, halogen, CN, OR*, SR*, CO₂R*, CF₃, NR⁵R⁶, or (CH₂)ₙOR⁵ wherein R*, R⁵, and R⁶ are each independently hydrogen or a straight or branched alkyl of from 1 to about 6 carbon atoms; m, n, p, q, r, s, t, u, and v are each independently an integer of from 0 to 6 with the proviso that q, r, and s are not all 1 when m, p, t, u, and v are all 0 except when X is not CONR⁹ or A—E is not (CH₂)ₙCONH—, —SO₂NH—, —S(O)NH—, —NHCONH, —(CH₂)ₙ—OCO—NH—, —SCONH—, —O(CH₂)ₙCO— or —HC=CHCONH— wherein n is as above, A is a bond,
O,
S,
NR*,
—(CH$_2$)$_n$CO—Z,
—SO$_2$—Z,
—SO—Z,
—S—Z,
—NHCO—Z,

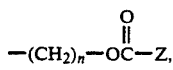

—SCO—Z,
—O—(CH$_2$)$_n$CO—Z,
—HC=CHCO—Z,
 wherein Z is a bond, oxygen, sulphur, or —NR*— wherein R* is as defined above;
E is a bond, an amino acid residue,
—(CHR$^3$)$_r$—, —(CHR$^3$)$_3$—(CHR$^4$)$_s$—,
—CONH—,
—NHCO—,
—OCO—,
—COO—,
—CH$_2$N(R$^3$)—,
—CH$_2$O—,
—CH$_2$S—,
—C≡C—,

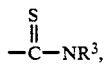

—SO$_2$NR$^3$—,
—NR$^3$SO$_2$—,
—NHCONH—

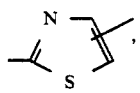

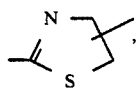

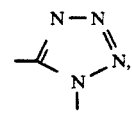

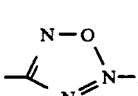

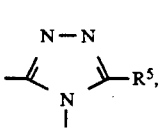

wherein r and s are independently as defined above and R$^3$ and R$^4$ are as defined above; R$^2$ and R$^{20}$ are each independently hydrogen, a straight or branched alkyl of from 1 to 6 carbon atoms, —HC=CH$_2$, —C≡CH, —(CH$_2$)$_n$CH=CH$_2$, —(CH$_2$)$_n$C≡CH, —(CH$_2$)$_n$Ar$^1$, —(CH$_2$)$_n$Ar$^2$, —(CH$_2$)$_n$OR*, —(CH$_2$)$_n$OAr, —(CH$_2$)$_n$CO$_2$R*, —(CH$_2$)$_n$NR$^5$R$^6$ wherein n, R*, R$^5$, and R$^6$ are as defined above, and Ar$^1$ and Ar2 are as defined below; X and Y are each independently:
—CONH—,
—CONR$^9$,
—NHCO—,
—OCO—,
—COO—,
—CH$_2$N(R$^3$)—,
—CH$_2$O—,
—CH$_2$S—,
—OCH$_2$—,
—SCH$_2$—,

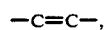

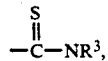

—SO$_2$NR$^3$—,

—NR$^3$SO$_2$—,

—NHCONH—,

—CH(OR*)CH$_2$—,

—COCH$_2$—,

—CH$_2$CO—,

—NR$^3$CH$_2$—,

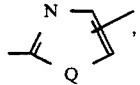

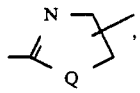

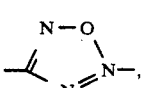

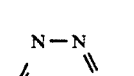

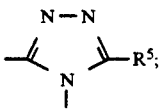

wherein Q is O, S, or NR$^9$;
R$^3$ and R$^4$ are each independently the same as R$^2$ or —(CH$_2$)$_{n'}$—B—D wherein n' is an integer of from 0 to 3;
B is a bond, —OCO(CH$_2$)$_n$—, —O(CH$_2$)$_n$—, -continued —NHCO(CH$_2$)$_n$—, —CONH(CH$_2$)$_n$—,

—NHCOCH=CH—,

—COO(CH$_2$)$_n$—,

—CO(CH$_2$)$_n$—,

—SO(CH$_2$)$_n$—,

—S(CH$_2$)$_n$—,

—SO$_2$(CH$_2$)$_n$—,

NHCO—C=C—,
  |    |
  R$^7$  R$^8$

H  H
          |  |
NHCO—C—C—,
          |  |
          R$^7$  R$^8$

CONH—C=C—, or
  |    |
  R$^7$  R$^8$

H  H
          |  |
CONH—C—C—,
          |  |
          R$^7$  R$^8$ wherein R$^7$ and R$^8$ are each independently selected from hydrogen and R$^2$ or together form a ring (CH$_2$)$_m$ wherein m is an integer of from 1 to 5, D is
—COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H, and acid replacements such as

[structure: HO-substituted pyranone]

[structure: 1,2,4 oxadiazole with R$^{10}$], R$^{10}$ is OH, NH$_2$, CH$_3$, or Cl
HO$_3$S—{
—PO$_3$H$_2$

[structures: triazole, thiol-triazole with HS, pyrrole with HN]

-continued

[structure with R$^{11}$ on triazole], R$^{11}$ is CN, CO$_2$H, or CF$_3$

[structure: diacyl hydrazide]
PhSO$_2$NHCO—{,
CF$_3$CONHCO—{,
CF$_3$SO$_2$NHCO—{,
H$_2$NSO$_2$—{,

[structure: HO-isoxazole], [structure: dioxolane with CH$_3$],

—S(O)$_b$—[triazole], —S(O)$_b$—[imidazole],

—S(O)$_b$—[imidazolone], —S(O)$_b$—[tetrazole],

—S(O)$_b$—[phenyl with NR$^5$RH and R$^{10}$], —S(O)$_b$—[phenyl with HO and R$^{10}$], wherein b is an integer of from 0 to 2, wherein R*, R$^2$, R$^5$, and R$^6$ are as defined above; R$^9$ is H, or a straight or branched alkyl of from one to six carbon atoms, —(CH$_2$)$_n$CO$_2$R*, (CH$_2$)$_n$ORr', (CH$_2$)$_n$Ar', (CH$_2$)$_n$NR$^5$R$^6$, wherein n, R*, R$^5$, and R$^6$ are as defined above or taken from R$^3$ and Ar is taken from Ar$^1$ as defined below;

R$^{12}$ and R$^{13}$ are each independently hydrogen or taken together form a double bond, or are —(CH$_2$)$_n$—B—D as defined above; and Ar$^1$ and Ar$^2$ are each independently a mono- or polycyclic unsubstituted or substituted carbo- or heterocyclic aromatic or carbo- or heteroaromatic moiety.

Especially useful are compounds selected from:

Carbamic acid, [2-[[1-(hydroxymethyl)-2-phenylethyl]amino]-1-(1H-indol-3-ylmethyl)ethyl]-, tricyclo[3.3.1.1$^{3,7}$]dec-2-yl ester, [S-(R*,S*)]-, Carbamic acid, [2-[[1-(hydroxymethyl)-1-phenylethyl]amino]-1-(1H-indol-3-ylmethyl)ethyl-, tricyclo[3.3.1.1$^{3,7}$]dec-2-yl ester, [S-(R*,R*)]-, Tricyclo[3.3.1.1$^{3,7}$]dec-2-yl[1-[[[1-hydroxymethyl)-2-phenylethyl]carbonyl]amino]-2-(1H-indol-3-yl)ethyl]carbamate, Carbamic acid, [2-[(2-hydroxy-2-phenylethyl)amino]-1-(1H-indol-3-ylmethyl)-1-methylethyl ]-, tricyclo[3.3.1.1$^{3,7}$]dec-2-yl ester (hydroxy center is RS, other center is R), Carbamic acid, [2-[[1-(hydroxymethyl)-2-phenylethyl]amino]-1-(1H-indol-3-ylmethyl)-1-methylethyl]-, tricyclo[3.3.1.1$^{3,7}$]dec-2-yl ester, [R-(R*,S*)]-, 4-methylbenzenesulfonate (1:1) (salt), Benzenepropanol,β-[[2-(1H-indol-3-yl)-2-[[(tricyclo[3.3.1.1³,⁷]dec-2-yloxy)carbonyl ]amino]propyl]amino]-, acetate (ester), [R-(R*,S*)]-, 4-methylbenzenesulfonate (1:1) (salt), Carbamic acid, [[2-[acetyl[1-(hydroxymethyl)-2-phenylethyl]amino]-1-(1H-indol-3-ylmethyl) -1-methyl]ethyl]-, tricyclo[3.3.1.1³,⁷]dec-2-yl ester, [R-(R*,S*)]-, 5,13-Dioxa-2,8-diazatetradec-10-enoic acid, 3-(1H-indol-3-ylmethyl)-3-methyl-4,9,12-trioxo -7-phenyl-, tricyclo[3.3.1.1³,⁷]dec-2-yl ester, S-(R*,S*)]-, 5,13-Dioxa-2,8-diazatetradecanoic acid, 3-(1H-indol-3-ylmethyl)-3-methyl-4,9,12-trioxo-7-phenyl-, tricyclo[3.3.1.1³,⁷]dec-2-yl ester, [R*,R*)]-, Carbamic acid, [1-(1H-indol-3-ylmethyl)-1-methyl-2-[(1-oxo-4-phenylbutyl)amino]ethyl]-, tricyclo[3.3.1.1³,⁷]dec-2-yl ester (R)-, Carbamic acid, [2-(benzoylamino)-1-(1H-indol-3-ylmethyl)-1-methylethyl]-, tricyclo[3.3.1.1³,⁷]-dec-2-yl ester, (R)-, Carbamic acid, [1-(1H-indol-3-ylmethyl)-1-methyl-2-[(1-oxo-3-phenylpropyl)amino]ethyl ]-, tricyclo[3.3.1.1³,⁷]dec-2-yl ester, (R)-, Carbamic acid, [1-(1H-indol-3-ylmethyl)-1-methyl-2-[(2-phenylacetyl)amino]ethyl]-, tricyclo3.3.1.1³,⁷]dec-2-yl ester, (R)-, Carbamic acid, [2-[[3-[[1-(hydroxymethyl)-2-phenylethyl]amino]-3-oxopropyl]amino]-1-( 1H-indol-3-ylmethyl)-1-methyl-2-oxoethyl]-, [R,(R*,S*)]-, Carbamic acid, [1-(1H-indol-3-ylmethyl)-2-[[3-[[1-(hydroxymethyl)-2-phenylethyl]amino ]-3-oxopropyl]amino]-1-methyl-2-oxoethyl]-, tricyclo[3.3.1.1³,⁷]dec-2-yl ester, [S-(R*,R*)]-, D-Phenylalaninamide, α-methyl-N-[(tricyclo[3.3.1.1³,⁷]dec-2-yloxy)carbonyl]-D-tryptophyl-β-alanyl-, L-Phenylalaninamide, α-methyl-N-[(tricyclo[3.3.1.1³,⁷]dec-2-yloxy)carbonyl]-D-tryptophyl-β-alanyl-, L-Phenylalaninamide, α-methyl-N-[(tricyclo[3.3.1.1³,⁷]dec-2-yloxy)carbonyl]-L-tryptophyl-β-alanyl-, D-Phenylalaninamide, α-methyl-N-[tricyclo[3.3.1.1³,⁷]dec-2-yloxy)carbonyl]-L-tryptophyl-β-alanyl-, 12-Oxa-2,5,9-triazatridecanoic acid, 3-(1H-indol-3-ylmethyl)-3-methyl-4,8,11-trioxo-10-(phenylmethyl)-, tricyclo[3.3.1.1³,⁷]dec-2-yl ester, [R,(R*,R*)]-, L-Phenylalanine, N-[N-[α-methyl-N-[(tricyclo[3.3.1.1³,⁷]dec-2-yloxy)carbonyl]-D-tryptophyl]-β-alanyl]-, phenylmethyl ester, Propanoic acid, 2-[[3-[[3-(1H-indol-3-yl)-2-methyl-1-oxo-2-[[(tricyclo[3.3.1.1³,⁷]dec-2-yloxy)carbonyl]amino]propyl]amino]-1-oxopropyl]amino]-3-phenyl-, phenylmethyl ester, [S-(R*,R*)]-, D-Phenylalanine, N-[N-[α-methyl-N-[(tricyclo[3.3.1.1³,⁷]dec-2-yloxy)carbonyl]-D-tryptophyl]-β-alanyl]-, L-Phenylalanine, N-[N-[α-methyl-N-[(tricyclo[3.3.1.1³,⁷]dec-2-yloxy)carbonyl]-D-tryptophyl]-β-alanyl]-, L-Phenylalanine, N-[N-[α-methyl-N-[(tricyclo[3.3.1.1³,⁷]dec-2-yloxy)carbonyl]-L-tryptophyl]-β-alanyl]-, Benzenepropanoic acid, α-[[3-[[3-[(1H-indol-3-yl)-2-methyl-1-oxo-2-[[(tricyclo[3.3.1.1³,⁷]dec-2-yloxy)carbonyl]amino]propyl]amino]-1-oxopropyl]-amino]-, [S-(R*,S*)]-, Glycine, N-[2-methyl-N-[(tricyclo[3.3.1.1³,⁷]dec-2-yloxy)carbonyl]-D-tryptophyl]-, phenylmethyl ester, Carbamic acid, [3-(1H-indol-3-ylmethyl)-2,5-dioxo-1-(2-phenylethyl)-3-pyrrolidinyl]-, tricyclo[3.3.1.1³,⁷]-dec-2-yl ester, (±)-, Carbamic acid, [1-(1H-imidazol-4-ylmethyl)-1-methyl-2-oxo-2-[(2-phenylethyl)amino]ethyl]-, 1,1-dimethylethyl ester, (±)-, Carbamic acid, [3-(1H-indol-3-yl)-1-methyl-1-[[(2-phenylethyl)amino]carbonyl]propyl]-, tricyclo[3.3.1.1³,⁷]dec-2-yl ester, (±)-, Carbamic acid, [1-[[[1-hydroxymethyl)-2-phenylethyl]amino]carbonyl]-3-(1H-indol-3-yl) -1-methylpropyl]-, tricyclo[3.3.1.1³,⁷]dec-2-yl ester (hydroxymethyl center is S, other center is RS), 13-Oxa-2,5,β-triazatetradec-10-enoic acid, 3-[2-(1H-indol-3-yl)ethyl]-3-methyl -4,5,12-trioxo-7-phenyl-, tricyclo[3.3.1.1³,⁷]dec-2-yl ester [TRP center is R/S mixture, other center is R], L-Phenylalaninamide, N-[[(1,1-dimethylethoxy)carbonyl]-α-methyl]-L-tryptophyl]-L-methionyl-L-β-aspartyl-, Glycine, N-[2-methyl-N-[(tricyclo-[3.3.1.1³,⁷]dec-2-yloxy)carbonyl]-D-tryptophyl]-L-phenylalanyl-, Carbamic acid, [1-[[[1-(hydroxymethyl)-2-phenylethyl]amino]carbonyl]-2-(1H-indol-3-yl) propyl]-, tricyclo[3.3.1.1³,⁷]dec-2-yl ester (hydroxymethyl center S, other centers RS), 2,4-Heptadienoic acid, 6-[[3-(1H-indol-3-yl)-2-methyl-1-oxo-2-[[(tricyclo[3.3.1.1³,⁷]dec-2-yloxy)carbonyl]amino]propyl]amino]-7-phenyl-, [R,R*,S*-(E,E)]]-, Glycine, N-[2-methyl-N-[(tricyclo-[3.3.1.1³,⁷]dec-2-yloxy)carbonyl]-D-tryptophyl]-, phenylmethyl ester, and Tricyclo[3.3.1.1³,⁷]dec-2-yl-R-(R*,S*)]-[1-[4,5-dihydro-4-(phenylmethyl)-2-thiazolyl]-2-(1H-indol-3-yl)-1-methylethyl]carbamate.

Other compounds useful in the method of treating depression of the instant invention are those of formula

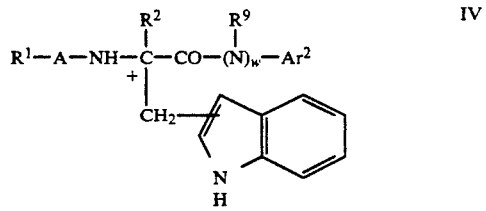

or a pharmaceutically acceptable salt thereof wherein:

$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or $-(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is $-(CH_2)_nCO-$, $-SO_2-$, $-SO-$, $-NHCO-$,

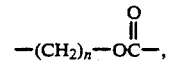

—SCO—, —O—(CH$_2$)$_n$CO— or —HC=CHCO—
wherein n is an integer from zero to six;

R$^2$ is a straight or branched alkyl of from one to six carbon atoms, —HC=CH$_2$, —C≡CH, —(CH$_2$)$_n$—CH=CH$_2$, —(CH$_2$)$_n$C≡CH, —(CH$_2$)$_n$Ar, —(CH$_2$)$_n$OR*, —(CH$_2$)$_n$OAr, —(CH$_2$)$_n$CO$_2$R*, —(CH$_2$)$_n$NR$^5$R$^6$ wherein n, R, R$^5$, and R$^6$ are as defined above and Ar is a mono or polycyclic unsubstituted or substituted carbo- or heterocyclic aromatic or hydroaromatic moiety;

R$^9$ is H, or a straight or branched alkyl of from one to six carbon atoms, —(CH$_2$)$_n$CO$_2$R*, (CH$_2$)$_n$OAr', (CH$_2$)$_n$Ar', (CH$_2$)$_n$NR$^5$R$^6$, wherein n, R*, R$^5$, and R$^6$ are as defined above or taken from R$^3$ and Ar' is taken independently from Ar and w is zero or 1;

Ar$^2$ is

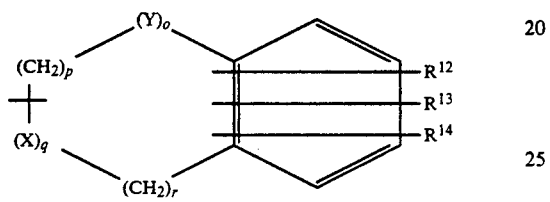

wherein x and y are each independently O, S, N, CH$_2$, —CHR$^{12}$, —NR$^{12}$—, —NR$^{12}$CO—, —C=N—, —C=C—, or —(C=O)— or a bond; o, p, q, and r are each independently an integer of from 0 to 3, provided that when o, p, q, and r are all simultaneously zero, Ar$^2$ becomes

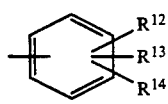

R$^{12}$, R$^{13}$, and R$^{14}$ are each independently halogen, R$^2$ as is defined above, —(CH$_2$)$_g$—B—D wherein g is an integer of from 0 to 6 wherein
B is a bond,
—OCO(CH$_2$)$_n$—,
—O(CH$_2$)$_n$—,
—NHCO(CH$_2$)$_n$—,
—CONH(CH$_2$)$_n$—,
—NHCOCH=CH—,
—COO(CH$_2$)$_n$—,
—CO(CH$_2$)$_n$—,
—S(CH$_2$)$_n$—,
—SO(CH$_2$)$_n$—,
—SO$_2$(CH$_2$)$_n$—,

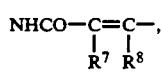

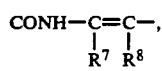

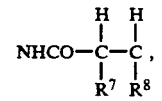

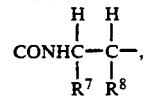

—NHSO$_2$—(CH$_2$)$_n$—, or

—SO$_2$NH—(CH$_2$)$_n$—, wherein R$^7$ and R$^8$ are independently selected from hydrogen and R$^2$, or together form a ring (CH$_2$)$_m$ wherein m is an integer of from 1 to 5 and n is as defined above;

D is
—COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H, and acid replacements such as tetrazole,

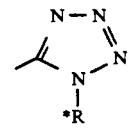

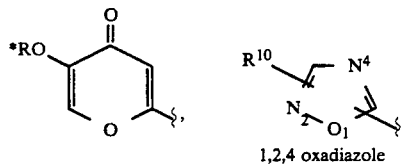

1,2,4 oxadiazole

R$^{10}$ is OR*, NR$^5$R*, CH$_3$, or Cl
HO$_3$S—$\{$
$\}$—PO$_3$H$_2$

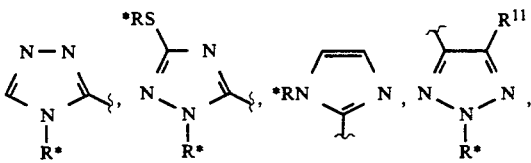

R$^{11}$ is CN, CO$_2$H, or CF$_3$,

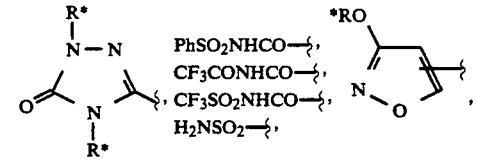

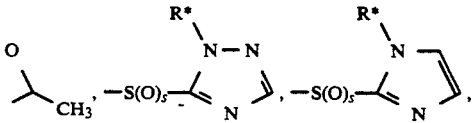

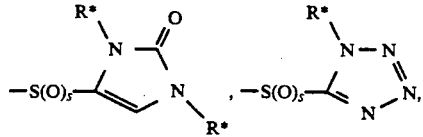

-continued

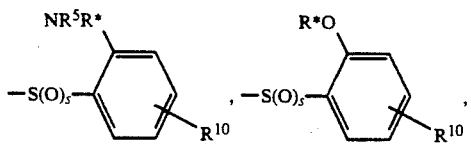

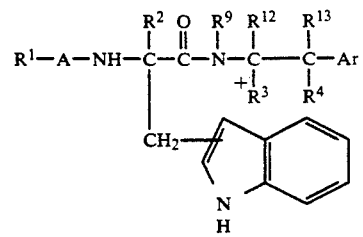

wherein s is an integer of from 0 to 2 wherein R*, R², R⁵, and R⁶ are as defined above.

Especially useful are compounds selected from:

carbamic acid, [2-[(2,3-dihydro-2-hydroxy-1H-inden-1-yl)amino)-1-(1H-indol-3-ylmethyl) -1-methyl-2-oxoethyl]-, 1,7,7-trimethylbicyclo-[2.2.1]hept-2-yl ester (bicyclo ring is 1S-endo (+ −isomer), trp center is D, indene ring centers are unknown), carbamic acid, [2-[(2,3-dihydro-1-hydroxy-1H-inden-2-yl)amino]-1-1H-indol-3-ylmethyl) -2-methyl-2-oxoethyl]-, 1,7,7-trimethylbicyclo-[2.2.1]hept-2-yl ester, [1S*[1α,2β[S-(trans)],4β]]- (Bicyclo system is 1S-endo), carbamic acid, [2-[(2,3-dihydro-1-hydroxy-1H-inden-2-yl)amino]-1-(1H-indol-3-ylmethyl)-1-methyl-2-oxoethyl]-, 1,7,7-trimethylbicyclo-[2.2.1]hept-2-yl ester, [1S-[1α,2β[S*(1S*,2S*)],4α]]- [Bicyclo system is 1S-endo, all other centers are R], carbamic acid, [1-(1H-indol-3-ylmethyl)-1-methyl-2-oxo-2-[(1,2,3,4-tetrahydro-1-oxo-2-naphthalenyl)amino]ethyl]-, 1,7,7-trimethylbicyclo[2.2.1]hept-2-yl ester (Bicyclo system 1S-endo; TRP center R; naphthyl center (−) or (+)), (Isomer II), carbamic acid, [1-(1H-indol-3-ylmethyl)-1-methyl-2-oxo-2-[(1-2,3,4-tetrahydro-1-oxo -2-naphthalenyl)amino]ethyl]-, 1,7,7-trimethylbicyclo[2.2.1.1]hept-2-yl ester (Bicyclo system IS-endo; TRP center R: naphthyl center (+) or (−)), (Isomer 1), carbamic acid, [1-(1H-indol-3-ylmethyl)-1-methyl-2-oxo-2-[(1,2,3,4-tetrahydro-1-naphthalenyl)amino]ethyl]-, tricyclo[3.3.1.1³,⁷]-dec-2-yl ester, (±)-, carbamic acid, [1-1H-indol-3-ylmethyl)-1-methyl-2-oxo-2-[(1,2,3,4-tetrahydro-2-naphthalenyl)amino]ethyl]-, tricyclo[3.3.1.1³,⁷]-dec-2-yl ester, (±)-, carbamic acid, [1-(1H-indol-3-ylmethyl)-1-methyl-2-oxo-2-(1,2,3,4-tetrahydro-2-isoquinolinyl)ethyl]-, tricyclo[3.3.1.1³,⁷]-dec-2-yl ester, (R)-, 4-[[1,2,3,4-tetrahydro-2-[[3-(1H-indol-3-yl)-2-methyl-1-oxo-2-[[(tricyclo[3.3.1.1³,⁷]dec-2-yloxy)carbonyl]amino]propyl]amino]-1-naphthalenyl]amino]-4-oxobutanoate tricyclo[3.3.1.1³,⁷]dec-2-yl-[2-[(1-azido-1,2,3,4-tetrahydro-2-naphthalenyl)amino]-1-(1H-indol-3-ylmethyl)-1-methyl-2-oxoethyl]carbamate, methyl 3-[[2-[[3-(1H-indol-3-yl)-2-methyl-1-oxo2-[[(tricyclo[3.3.1.1 ³,⁷]dec-2-yloxy)carbonyl]amino]propyl]amino]-1,2,3,4-tetrahydro-1-naphthalenyl]amino]-3-oxopropanoate, methyl 3-[[2-[[3-(1H-indol-3-yl)-2-methyl-1-oxo-2-[[(tricyclo[3.3.1.1 ³,⁷]dec-2-yloxy)carbonyl]amino]propyl]amino]-1,2,3,4-tetrahydro-1-naphthalenyl]amino]-3-oxopropanoate, and methyl 1-[[1,2,3,4-tetrahydro-2-[[3-(1H-indol-3-yl)-2-methyl-1-oxo-2-[[(tricyclo[3.3.1.1³,⁷]dec-2-yloxy)carbonyl]amino]propyl]amino]-1-naphthalenyl]-amino]-4-oxo-2-butanoate.

Other compounds useful in the method of treating depression of the instant invention are those of formula or a pharmaceutically acceptable salt thereof wherein:

R¹ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, CO₂R*, CF₃, NR⁵R⁶, and —(CH₂)ₙOR⁵ wherein R* is hydrogen, straight or branched alkyl of from one to six carbon atoms, —(CH₂)ₙAr, —COAr, —(CH₂)ₙOCOAr, or —(CH₂)ₙNR⁵COAr and R* may also independently be R as defined below, and R must be present at least once in formula I, and R** is attached to formula I through a metabolically labile bond and can include

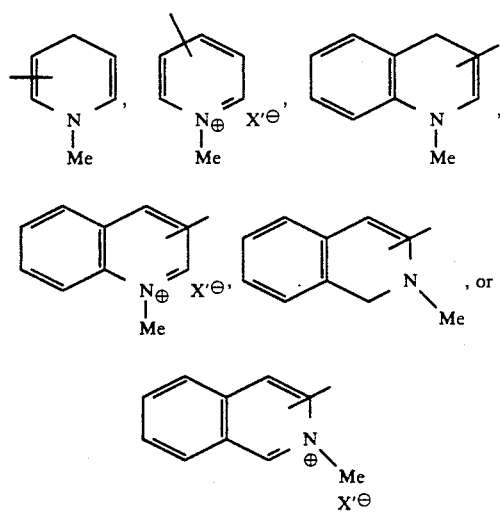

R⁵ and R⁶ are each independently hydrogen or alkyl of from one to about six carbon atoms and n is an integer from zero to six; and R** is —(CH₂)ₙNR⁵R⁶, —(CH₂)ₙ—B—D* wherein D* is O—COR*, CO₂Ar², (CH₂)ₙAr², OCOAr², NR⁵COAr², COAr², CO₂CH(-R)—CO₂R*, CO₂—(CH₂)ₙOCOR* where Ar² is independently taken from Ar, where m is as defined below, CONHCH(R)CO₂R* where R is a side chain of a biologically significant amino acid, R is hydrogen only when B is not a bond, —CO₂CH₂CH₂N+(R*)₃X¹⁻ when X¹⁻ is a pharmaceutically acceptable counter anion, A is —(CH₂)ₙCO—, —SO₂—, —S(=O)—, —NH-CO—, —(CH)ₙ—C(=O)—,

—O—(CH₂)ₙCO— or —HC=CHCO— wherein n is an integer from zero to six;

$R^2$ is a straight or branched alkyl of from one to about six carbon atoms, $-HC=CH_2$, $-C\equiv CH$, $-(CH_2)_n-CH=CH_2$, $-(CH_2)_nC\equiv CH$, $-(CH_2)_nAr$, $-(CH_2)_nOR^*$, $-(CH_2)_nOAr$, $-(CH_2)_nCO_2R^*$, or $-(CH_2)_nNR^5R^6$ wherein n, $R^*$, $R^5$ and $R^6$ are as defined above and Ar is as defined below;

$R^3$ and $R^4$ are each independently selected from hydrogen, $R^2$ and $-(CH_2)_{n'}-B-D$ wherein:

n' is an integer of from zero to three;

B is a bond,
- $-OCO(CH_2)_n-$,
- $-O(CH_2)_n-$,
- $-NHCO(CH_2)_n-$,
- $-CONH(CH_2)_n-$,
- $-NHCOCH=CH-$,
- $-COO(CH_2)_n-$,
- $-CO(CH_2)_n-$,
- $-S-(CH_2)_n-$,
- $-S(=O)-(CH_2)_n-$,
- $-SO_2-(CH_2)_n-$,
- $-NHSO_2-(CH_2)_n-$,
- $-SO_2NH-(CH_2)_n-$, $$NHCO-\underset{R^7\ R^8}{C=C}-,$$

$$CONH-\underset{R^7\ R^8}{C=C}-,$$

$$NHCO-\underset{R^7\ R^8}{\overset{H\ H}{C-C}}-, \text{ or}$$

$$CONH-\underset{R^7\ R^8}{\overset{H\ H}{C-C}}-$$

wherein $R^7$ and $R^8$ are each independently selected from hydrogen and $R^2$ or together form a ring $(CH_2)_m$ wherein m is an integer of from 1 to 5 and n is as defined above;

D is hydrogen,
- $-COOR^*$,
- $-CH_2NR^5R^*$,
- $-CHR^2NR^5R^*$,
- $-CH_2OR^*$,
- $-CHR^2OR^*$,
- $-CH_2SR^*$,
- $-CHR^2SR^*$,
- $-CONR^5R^6$,
- $-CONR^5R^*$, an acid replacement selected from

[tetrazole structure with N-N, N, N, R*]

[*RO-pyranone structure]

[R10, N4, N2, O1 — 1,2,4 oxadiazole]

-continued $R^{10}$ is $OR^*$, $NR^5R^*$, $CH_3$, or Cl;
$HO_3S-$
$-PO_3H_2-$

[structures: *RS-triazole with N-N, N, R*; pyrazole R*N, N, R*; triazole with R^{11}, N, N, N, R*]

$R^{11}$ is CN, $CO_2H$, or $CF_3$,

[structures: N-N oxo ring with R*; PhSO_2NHCO-, CF_3CONHCO-, CF_3SO_2NHCO-, H_2NSO_2-; R*O-isoxazole N-O]

[dioxolane-CH_3 O O; $-S(O)_m-$ triazole with R*, N-N, N; $-S(O)_m-$ imidazole with R*, N]

[$-S(O)_m-$ oxo-dihydropyridine R*, N, O, R*; $-S(O)_m-$ tetrazole R*, N-N, N, N]

[$-S(O)_m-$phenyl-$NR^5R^*$, $R^{10}$; $-S(O)_m-$phenyl-$R^*O$, $R^{10}$]

wherein m is an integer of from 0 to 2 wherein $R^*$, $R^2$, $R^5$, and $R^6$ are as defined above;

$R^9$ is hydrogen or a straight or branched alkyl of from one to about six carbon atoms, $-(CH_2)_nCO_2R^*$, $-(CH_2)_nNR^5R^*$, wherein n, $R^*$, and $R^5$ are as defined above or taken from $R^3$;

$R^{12}$ and $R^{13}$ are each independently hydrogen or are each independently taken with $R^3$ and $R^4$, respectively, to form a moiety doubly bonded to the carbon atom; and Ar is a mono- or polycyclic unsubstituted or substituted carbo- or heteroaromatic or carbo- or heterohydroaromatic moiety.

Especially useful are compounds selected from:

L-Aspartic acid, N-[N-[α-methyl-N-[(tricyclo[3.3.1.1³,⁷]-dec-2-yloxy)carbonyl]-D-tryptophyl]-L-phenylalanyl]-, L-Glutamic acid, N-[N-[α-methyl-N-[(tricyclo[3.3.1.1³,⁷]-dec-2-yloxy)carbonyl]-D-tryptophyl]-L-phenylalanyl]-, L-Glutamic acid, N-[N-[α-methyl-N-[(tricyclo[3.3.1.1³,⁷]-dec-2-yloxy)carbonyl]-D-tryptophyl]-L-phenylalanyl]-, dimethyl ester, 2-[[3-(1H-Indol-3-yl)-2-methyl-1-oxo-2[[tricyclo[3.3.1.1³,⁷]dec-2-yloxy)carbonyl]amino]propyl]-amino]-3-phenylpropyl]R-(R*S*)]-1,4-dihydro-1-methyl-3-pyridinecarboxylate, 2-[[3-(1H-indol-3-yl)-2-methyl-1-oxo-2[[(tricyclo-[3.3.1.1³,⁷]dec-2-yloxy)carbonyl]-amino]propyl]- amino]-3-phenylpropyl[R-(R*,S*)]-trigonelline iodide

2-[3-[3-(1H-indol-3-yl)-2-methyl-1-oxo-2-[[tricyclo-[3.3.1.1³,⁷]dec-2-yloxy)carbonyl]-amino]propyl-]amino]-3-phenylpropyl[R-(R*,S*)]-3-pyridinecarboxylate, butanoic acid, 4-[[2-[[3-(1H-indol-3-yl)-2-methyl-1-oxo-2-[[(tricyclo[3.3.1.1³,⁷]dec-2-yloxy)carbonyl]amino]-propyl]amino]-1-phenylethyl]amino]-4-oxo-, (2,2-dimethyl-1-oxopropoxy)methyl ester, [R-(R*,R*)]-, butanoic acid, 4-[[2-[[3-(1H-indol-3-yl)-2-methyl-1-oxo-2-[[(tricyclo[3.3.1.1³,⁷]dec-2-yloxy)-carbonyl]amino]-propyl]amino]ethyl]amino]-4-oxo-, chloromethyl ester, [R-(R*,R*)]-, Pentanedioic acid, [4-[[2-[[3-(1H-indol-3-yl)-2-methyl-1-oxo-2-[[(tricyclo [3.3.1.1³,⁷]dec-2-yloxy)-carbonyl]amino]propyl]amino]-1-phenylethyl]amino]-1,4-dioxobutoxy]methyl ester, [R-(R*,R*)]-, butanoic acid, 4-[[2-[[3-(1H-indol-3-yl)-2-methyl-1-oxo-2-[[(tricyclo[3.3.1.1³,⁷]dec-2-yloxy)carbonyl]amino]-propyl]amino]-1-phenylethyl]amino]-4-oxo-2,3-dihydro -1H-inden-5-yl ester, [R-(R*,R*)]-, and butanoic acid, 4-[[2-[[3-(1H-indol-3-yl)-2-methyl-1-oxo-2-[[(tricyclo[3.3.1.1³,⁷]dec-2-yloxy)-carbonyl]amino]-propyl]amino]-1-phenylethyl]amino]-4-oxo-, [R-(R*,R*)]-.

Other compounds useful in the method of treating depression of the instant invention are those of formula

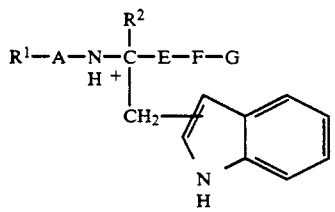

VI or a pharmaceutically acceptable salt thereof wherein:

$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or $-(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is $-(CH_2)_nCO-$, $-SO_2-$, $-SO-$, $-NHCO-$

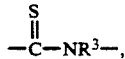

$-(CH_2)_n-OC-$,

—SCO—, —O—$(CH_2)_nCO$— or —HC=CHCO— wherein n is an integer from zero to six;

$R^2$ is a straight or branched alkyl of from one to six carbon atoms, —HC=$CH_2$, —C≡CH, —$CH_2$—CH=$CH_2$, —$(CH_2)_nC$≡CH, —$(CH_2)_n$Ar, —$(CH_2)_n$OR*, —$(CH_2)_n$OAr, —$(CH_2)_nCO_2R^*$, —$(CH_2)_nNR^5R^6$ wherein n, R, $R^5$ and $R^6$ are as defined above and Ar is a mono- or polycyclic unsubstituted or substituted carbo- or heterocyclic aromatic or hydroaromatic moiety;

E is —CONH—, —NHCO—, —OCO—, —COO—, —$(CH_2)_mNR^3$—, —$(CH_2)_mO$—, —$(CH_2)_mS$—, —C=C—,

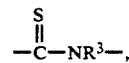

—$SO_2NR^3$—, —$NR^3SO_2$—, —NHCONH—, —$CH_2CO$—, —$COCH_2$—, —$(CH_2)_mNHCO$—, —$(CH_2)_mCONH$— wherein m is an integer of from 1-5,

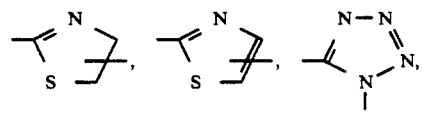

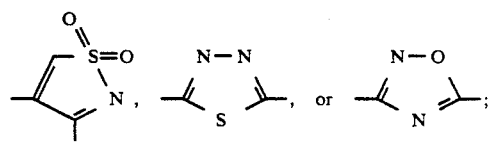

F is a bond, —CH(R)CO— wherein R is —$(CHR^3)_p$—$(CHR^4)_q$—D, wherein D is as defined below, wherein p and q are each independently 0, 1, or 2 and wherein F is a desamino biologically significant amino acid, excluding Tyr, Phe, Trp, His;

$R^3$ and $R^4$ are each independently selected from $R^2$ and —$(CH_2)_{n'}$—B—D wherein:

n' is an integer of from zero to three;

B is a bond,
—$OCO(CH_2)_n$—,
—$O(CH_2)_n$—,
—$NHCO(CH_2)_n$—,
—$CONH(CH_2)_n$—,
—NHCOCH=CH—,
—$COO(CH_2)_n$—,
—$CO(CH_2)_n$—,
—S—$(CH_2)_n$—,
—S(=O)—$(CH_2)_n$—,
—$SO_2$—$(CH_2)_n$—,
—$NHSO_2$—$(CH_2)_n$—,
—$SO_2NH$—$(CH_2)_n$—,

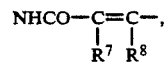

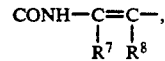

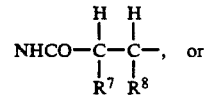

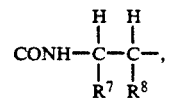

wherein $R^7$ and $R^8$ are independently selected from hydrogen and $R^2$ or together form a ring $(CH_2)_m$ wherein m is an integer of from 1 to 5 and n is as defined above;

D is
—COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H or an acid replacement such as tetrazole, or

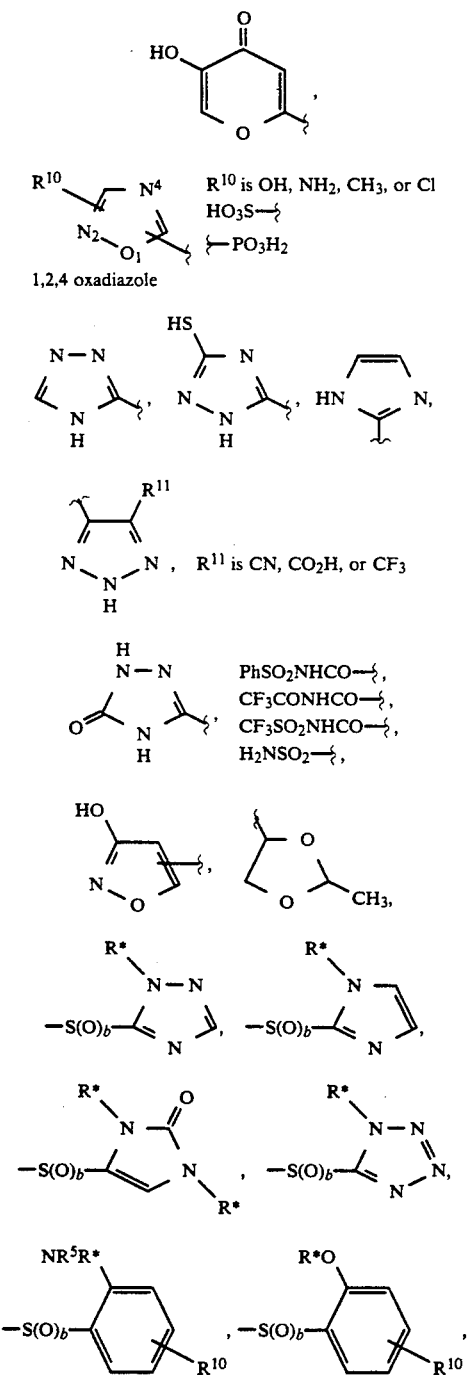

wherein s is an integer of from 0 to 2, wherein R*, R$^2$, R$^5$, and R$^6$ are as defined above and G is R$^3$ as defined above, and G cannot be hydrogen when F is a bond.

Especially useful are compounds selected from:
(R)-N-[3-(1H-indol-3-yl)-2-methyl-1-oxo-2-[[(tricyclo[3.3.1.1$^{3,7}$]dec-2-yloxy) carbonyl]amino]propyl]glycine, (R)-4-[[3-(1H-indol-3-yl)-2-methyl-1-oxo-2-[[(tricyclo[3.3.1.1$^{3,7}$]dec-2-yloxy)carbonyl]amino]propyl-]amino]butanoic acid, Methyl (R)-4-[[3-(1H-indol-3-yl)-2-methyl-1-oxo-2-[[(tricyclo[3.3.1.1$^{3,7}$]dec-2-yloxy)carbonyl]amino]-propyl]amino]butanoate, Phenylmethyl (R)-3-[[3-(1H-indol-3-yl)-2-methyl-1-oxo-2-[[(tricyclo[3.3.1.1$^{3,7}$]dec-2-yloxy)carbonyl]amino]propyl]amino]propanoate, Methyl N-[α-methyl-N-[(tricyclo[3.3.1.1$^{3,7}$]-dec-2-yloxy)carbonyl]-D-tryptophyl]-β-alanine, Phenylmethyl N-[2-methyl-N-[(tricyclo-[3.3.1.1$^{3,7}$]-dec-2-yloxy)carbonyl]-D-tryptophyl]glycine, N-[α-methyl-N-[(tricyclo[3.3.1.1$^{3,7}$]dec-2-yloxy)-carbonyl]-D-tryptophyl]-β-alanine, Tricyclo[3.3.1.1$^{3,7}$]dec-2-yl [1S-[1R*(S*),2R*]]-2-[[1-(hydroxy-methyl) -2-methyl-butyl]amino]-1-(1H-indol-3-ylmethyl)-1-methyl-2-oxoethyl]carbamate, Tricyclo[3.3.1.1$^{3,7}$]dec-2-yl [R-(R*,S*)]-[2-[[1-(hydroxymethyl)-3-methylbutyl]amino ]-1-(1H-indol3-ylmethyl)-1-methyl-2-oxoethyl]carbamate, Methyl N-[α-methyl-N-[(tricyclo-[3.3.1.1$^{3,7}$]dec-2-yloxy)carbonyl]-D-tryptophyl]-L-methionine, N-[α-methyl-N-[(tricyclo[3.3.1.1$^{3,7}$]dec-2-yloxy)carbonyl]-D-tryptophyl]-L-methionine, Methyl N-[N-[α-methyl-N-[(tricyclo-[3.3.1.1$^{3,7}$]dec-2-yloxy)carbonyl]-D-tryptophyl]-L-methionyl]-β-alanine, N-[S-methyl-N-[α-methyl-N-[(tricyclo[3.3.1.1$^{3,7}$]-dec-2-yloxy)carbonyl]-D-tryptophyl ]-D-cysteinyl-β-alanine, S-methyl-N-[β-methyl-N-[(tricyclo[3.3.1.1$^{3,7}$]dec-2-yloxy)carbonyl]-D-tryptophyl-D-cysteine, N-[α-Methyl-[N-[(tricyclo[3.3.1.1$^{3,7}$]dec-2-yloxy)carbonyl]-D-tryptophyl]-γ-(methylsulfinyl)-L -α-aminobutanoic acid, and N-[α-methyl-N-[(tricyclo[3.3.1.1$^{3,7}$]dec-2-yloxy)-carbonyl]-D-tryptophyl]-γ-(methylsulfonyl)-L-α-aminobutanoic acid.

Other compounds useful in the method of treating depression of the instant invention are those of formula ![Formula VI structure]

or a pharmaceutically acceptable salt thereof wherein:
R$^1$ is tert.-butyl, a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, CO$_2$R*, CF$_3$, NR$^5$R$^6$, and —(CH$_2$)$_n$OR$^5$ wherein R* is hydrogen or a straight or branched alkyl of from one to six carbon atoms, R$^5$ and $R^6$ are each independently hydrogen or alkyl of from one to about six carbon atoms and n is an integer from zero to six;

A is —$(CH_2)_nCO$—, $SO_2$—, —$S(=O)$—, —NHCO—,

—$(CH_2)_n$—OC(=O)—, —SCO—, —O—$(CH_2)_nCO$—,

—HC=CHCO—, or —C(=O)—O—$(CH_2)_n$— wherein n is an integer from zero to six;

$R^2$ is hydrogen, a straight or branched alkyl of from one to about six carbon atoms, —HC=$CH_2$, —C≡CH, —$CH_2$—CH=$CH_2$, —$CH_2$C≡CH, —$(CH_2)_n$Ar, —$(CH_2)_nOR^*$, —$(CH_2)_nOAr$, —$(CH_2)_nCO_2R^*$, or —$(CH_2)_nNR^5R^6$ wherein n, $R^*$, $R^5$ and $R^6$ are as defined above and Ar is as defined below;

$R^3$, $R^4$ and $R^{14}$ are each independently selected from hydrogen, $R^2$ and —$(CH_2)_{n'}$—B—D wherein:

n' is an integer of from zero to three;

B is a bond,
  —$OCO(CH_2)_n$—,
  —$O(CH_2)_n$—,
  —$NHCO(CH_2)_n$—,
  —$CONH(CH_2)_n$—,
  —NHCOCH=CH—,
  —$COO(CH_2)_n$—,
  —$CO(CH_2)_n$—,
  —$S(CH_2)_n$—,
  —$SO(CH_2)_n$—,
  —$SO_2(CH_2)_n$—,
  —$NHSO_2(CH_2)_n$—,
  —$SO_2NH(CH_2)_n$—,

NHCO—C($R^7$)=C($R^8$)—,

CONH—C($R^7$)=C($R^8$)—,

NHCO—CH($R^7$)—CH($R^8$)—,

CONH—CH($R^7$)—CH($R^8$)—, wherein $R^7$ and $R^8$ are independently selected from hydrogen and $R^2$ or together form a ring $(CH_2)_m$ wherein m is an integer of from 1 to 5 and n is as defined above;

D is
  —$COOR^*$,
  —$CH_2OR^*$,
  —$CHR^2OR^*$,
  —$CH_2SR^*$,
  —$CHR^2SR^*$,
  —$CONR^5R^6$,
  —CN,
  —$NR^5R^6$,
  —OH,

—H, and acid replacements such as tetrazole,

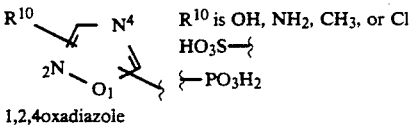

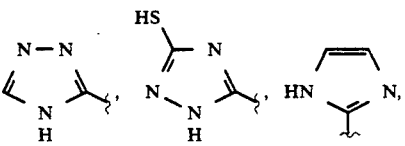

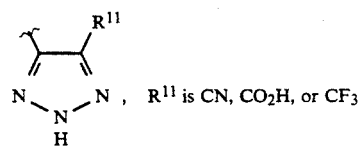

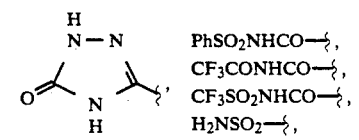

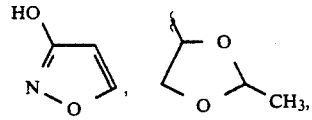

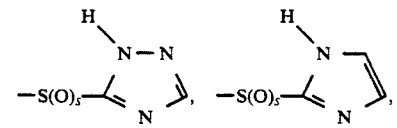

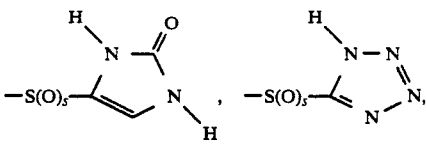

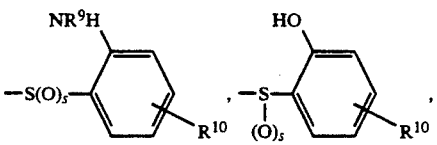

wherein $R^*$, $R^2$, $R^5$, and $R^6$ are as defined above;

$R^9$ is hydrogen or a straight or branched alkyl of from one to about six carbon atoms, —$(CH_2)_nCO_2R^*$, —$(CH_2)_nOAr$, —$(CH_2)_nAr'$ or $(CH_2)_nNR^5R^6$, wherein n, $R^*$, $R^5$, and $R^6$ are as defined above or taken from $R^3$ and Ar' is taken from Ar as defined below;

$R^{12}$ and $R^{13}$ are each independently hydrogen or are each independently taken with $R^3$ and $R^4$ respectively to form a moiety doubly bonded to the carbon atom; and Ar is a mono- or polycyclic unsubstituted or substituted carbo- or heterocyclic aromatic or hydroaromatic moiety.

Especially useful are compounds selected from:

(+/−)-1,3,4,9-tetrahydro-3-methyl-3-[[2-phenylethyl)amino]carbonyl]-2H-pyrido [3,4-b]indole-2-carboxylic acid, tricyclo[3.3.1.1$^{3,7}$]dec-2-yl ester, (R)-1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester, (S)-1,3,4,9-tetrahydro-3-methyl-3-[[2-phenyl-ethyl)amino]carbonyl]-2H-pyrido[3,4-b]indole-2-carboxylic acid, tricyclo[3.3.1.1$^{3,7}$]dec-2-yl ester, 1,3,4,9-tetrahydro-3-[[[1-(hydroxymethyl)-2-phenylethyl]amino]carbonyl]-3-methyl -2H-pyrido[3,4-b]indole-2-carboxylic acid, tricyclo[3.3.1.1$^{3,7}$]dec-2-yl ester (mixture of diastereomers), (R)-1,3,4,9-tetrahydro-3-[[[1-(hydroxymethyl)-2-phenylethyl]amino]carbonyl]-3-methyl -2H-pyrido[3,4-b]indole-2-carboxylic acid, tricyclo[3.3.1.1$^{3,7}$]dec-2-yl ester, (S)-1,3,4,9-tetrahydro-3-[[[1-(hydroxymethyl)-2-phenylethyl]amino]carbonyl]-3-methyl -2H-pyrido[3,4-b]indole-2-carboxylic acid, tricyclo[3.3.1.1$^{3,7}$]dec-2-yl ester, 1,3,4,9-tetrahydro-3-[[[1-(hydroxymethyl)-2-hydroxy-2-phenylethyl]amino]carbonyl]-3-methyl-2H-pyrido[3,4-b]indole-2-carboxylic acid, tricyclo[3.3.1.1$^{3,7}$]dec-2-yl ester, 3-[[(2-amino-2-phenylethyl)amino]carbonyl]-1,3,4,9-tetrahydro-3-methyl]-2H -pyrido[3,4-b]indole-2-carboxylic acid, tricyclo[3.3.1.1$^{3,7}$]dec-2-yl ester, (mixtures of diastereomers), 3-[[[2-(3-carboxy-1-oxopropyl)-amino]-2-phenylethyl]amino]carbonyl]-1,3,4,9-tetrahydro-3-methyl-2H-pyrido[3,4-b]indole-2-carboxylic acid, tricyclo[3.3.1.1$^{3,7}$]dec-2-yl ester, [R-(R*,R*)]and [R-(R*,S*)]-, 3-[[[2-(R)-(3-carboxy-1-oxopropyl)amino]-2-phenylethyl]amino]carbonyl]-1,3,4,9-tetrahydro-3-(S)-methyl-2H-pyrido[3,4-b]indole-2-carboxylic acid, tricyclo[3.3.1.1$^{3,7}$]dec-2-yl ester, 3-[3-[3-[2-[2-[1,4-dioxo-4-(phenylmethoxy)butyl]amino]-2-phenylethyl]amino carbonyl]-1,3,4,9-tetrahydro-3-methyl]-2H-pyrido[3,4-b]indole-2-carboxylic acid, tricyclo[3.3.1.1$^{3,7}$]dec-2-yl ester (mixture of diastereomers).

3-[[(2-hydroxy-2-phenylethyl)amino]carbonyl]-1,3,4,9-tetrahydro-3-methyl]-2H -pyrido[3,4-b]indole-2-carboxylic acid, tricyclo[3.3.1.1$^{3,7}$]dec-2-yl ester, butanedioic acid,mono[2-[[[2,3,4,9-tetrahydro-3-methyl-2-[(tricyclo[3.3.1.1$^{3,7}$]dec-2-ylox)carbonyl]-1H-pyrido[3,4-b]indole-3-yl]carbonyl]amino]-1-phenethyl]ester.

3-[[[2-[(3-carboxyacetyl)amino]-2-phenethyl]-amino]-carbonyl]-1,3,4,9-tetrahydro -3-methyl-2H-pyrido[3,4-b]indole-2-carboxylic acid, [tricyclo[3.3.1.1$^{3,7}$]dec-2-yl ester (mixture of diastereomers), 3-[[[2-[(3-carboxy-1-oxo-2-propenyl)amino]-2-phenethyl]amino]carbonyl]1,3,4,9-tetrahydro-3-methyl2H-pyrido[3,4-b]indole-2-carboxylic acid, [tricyclo[3.3.1.1$^{3,7}$]dec-2-yl ester (mixture of diastereomers), 3-[[[1-[[(3-carboxy-1-oxopropyl)amino]methyl]-1-phenethyl]amino]carbonyl]-1,3,4,9-tetrahydro-3-methyl2H-pyrido[3,4-b]indole-2-carboxylic acid, [tricyclo[3.3.1.1$^{3,7}$]dec-2-yl ester (mixture of diastereomers), (+/−)-1,3,4,9-tetrahydro-3-[[(2-phenethyl)amino]carbonyl]-2H-pyrido[3,4-b]indole-2-carboxylic acid, [tricyclo[3.3.1.1$^{3,7}$]]dec-2-yl ester, 3-[[(1-carboxy-2-phenethyl)amino]carbonyl]1,3,4,9-tetrahydro-2H-pyrido[3,4-b]indole-2-carboxylic acid, 1,1-dimethylethyl ester, (+/−)-1,3,4,9-tetrahydro-3-methyl-N-(2-phenylethyl)-2-[(tricyclo[3.3.1.1$^{3,7}$]dec-2-ylamino)sulfonyl]1H-pyrido[3,4-b]indole-3-carboxamide, 3-[[[3-carboxy-1-(phenylmethyl)propyl]amino]-carbonyl]-1,3,4,9-tetrahydro-3-methyl-2H-pyrido[3,4-b]indole-2-carboxylic acid, tricyclo[3.3.1.1$^{3,7}$]dec-2-yl ester, 1,3,4,9-tetrahydro-3-methyl-3-[[[2-[[1-oxo-3-(1H-tetrazol-5-yl)propyl]amino ]-2-phenethyl]amino]carbonyl]-2H-pyrido[3,4-b]indole-2-carboxylic acid, tricyclo[3.3.1.1$^{3,7}$]dec-2-yl ester, and 3-[[[2-[[(2-carboxy-1-cyclopropyl)carbonyl]-amino]-2-phenethyl]amino]carbonyl]-1,3,4,9-tetrahydro-3-methyl-2H-pyrido[3,4-b]indole-2-carboxylic acid ethyl ester, tricyclo[3.3.1.1$^{3,7}$]dec-2-yl ester.

Certain CCK$_B$ antagonists were tested in the Porsolt test, an animal model of depression, and in the "open field test" in the olfactory bulbectomised rat model of depression.

Methods

1. Porsolt Test (Behavioral Despair)

This test is based on the original method of Porsolt, et al (1977), Porsolt, R. D., La Pichon, M., and Jalpe, M. Depression: a new animal model sensitive to antidepressant treatment, *Nature* 266:730–732. On the first day of the experiment, the rats were plunged individually into a container 40 cm high, 18 cm diameter containing 15 cm of water at a temperature of 25° C. The animals were left to swim in the water for 15 minutes before being removed, allowed to dry, and returned to their home cage. Twenty-four hours later the procedure was repeated but on this occasion the duration that the rats remained immobile in a 5-minute observation period was recorded.

Animals received their first dose 15 minutes after removal from the water on the first day. They received the second dose 1 hour prior to the second placement in the water. Experiments were carried out in olfactory bulbectomised and in nonoperated animals.

Standard antidepressants such as desipramine caused a significant reduction in immobility in this test.

Results

1. Porsolt Test (Behavioral Despair)

The results obtained are shown in Tables 1 and 2 below.

TABLE I

| Group | | Time Immobile(s) |
|---|---|---|
| Vehicle | Median | 159 |
| (n = 8) | ST DEV | 54 |
|  | Q1–Q3 | 151–239 |
| CI-988 | Median | 97* |
| (n = 8) | ST DEV | 55 |
| 0.1 mg/kg) | Q1–Q3 | 85–160 |
| CI-988 | Median | 138 |
| (n = 8) | ST DEV | 35 |
| 1.0 mg/kg | Q1–Q3 | 100–178 |
| CI-988 | Median | 50* |
| (n = 8) | ST DEV | 25 |

TABLE I-continued

| Group | | Time Immobile(s) |
|---|---|---|
| 3.0 mg/kg | Q1–Q3 | 26–72 |
| CI-988 | Median | 150 |
| (n = 8) | ST DEV | 19 |
| 10 mg/kg | Q1–Q3 | 141–174 |

ST DEV = Standard Deviation
Q1–Q3 = Interquartile range
*P <0.005}
***P <0.001} Mann Whitney U Test Table I shows the effect of CI-988 in the Porsolt test in nonoperated animals. CI-988 (0.1 and 3.0 mg/kg) caused a significant decrease in immobility, indicating antidepressant activity.

TABLE II

| Group | | Time Immobile(s) |
|---|---|---|
| Sham Operated | Median | 186 |
| (n = 8) | ST DEV | 54 |
| control | Q1–Q3 | 142–227 |
| Desipramine* | Median | 46*** |
| (n = 10) | ST DEV | 36 |
| 7.5 mg/kg | Q1–Q3 | 22–86 |
| CI-988 | Median | 71** |
| (n = 8) | ST DEV | 43 |
| 3.0 mg/kg | Q1–Q3 | 35–87 |
| Olfactory | Median | 160 |
| Bulbectomised | ST DEV | 53 |
| control | Q1–Q3 | 91–183 |
| (n = 8) | | |
| Desipramine | Median | 48++ |
| 7.5 mg/kg | ST DEV | 46 |
| (n = 8) | Q1–Q3 | 28–98 |
| CI-988 | Median | 86+ |
| (n = 10) | ST DEV | 51 |
| 3.0 mg/kg | Q1–Q3 | 59–119 |

*10,11-dihydro-N-methyl-5H-di-benz[b,f]azepine-5-propanamine
**P <0.01
***P <0.001
+ = P <0.05
++ = P <0.01
ST DEV = Standard Deviation
Q1–Q3 = Interquartile range Table II shows the effect of desipramine and CI-988 in the Behavioral Despair (Porsolt test) in sham operated and olfactory bulbectomised rats. CI-988 and desipramine both reduced the period of immobility indicating antidepressant activity.

2. Open Field Test in Olfactory Bulbectomised Animals

This apparatus is essentially as described by Gray & Lalljee, Gray, J. A. and Lalljee, B. (1974): Sex differences in emotional behavior in the rat: correlation between the 'open field' defecation and active avoidance. *Anim. Behav.* 22: 856–861. The open field consisted of a circular base, 90 cm in diameter which was divided into 10 cm squares by faint yellow lines. The wall surrounding the base consisted of a 75 cm high aluminum sheet. Illumination was provided by a 60 watt bulb, positioned 90 cm above the floor of the apparatus. All measurements were carried out in a darkened room in the morning. Each animal was placed in the center of the open field apparatus and the following parameters were measured over a 3 minute period:
a) Ambulation: the number of squares crossed;
b) Rearing: the number of times the rat simultaneously raised both forepaws off the floor of the apparatus;
c) Grooming: the number of times the rat stopped and groomed itself; and
d) Defecation: the number of fecal boli deposited.

Experiments were carried out in sham operated rats and in rats with olfactory bulbectomy performed as described by Cairncross, K. D., Wren, A. F., Cox, B., and Schrieden, H. (1977): Effects of olfactory bulbectomy and domicile on stress induced corticosteroid release in the rat, *Physiol. Behav.* 19: 4845–487.

Results

2. Open Field Test in Olfactory Bulbectomised Rats

The results obtained are shown in Table 3 below.

TABLE III

| Group | | Ambulation | Rearing | Grooming | Defecation |
|---|---|---|---|---|---|
| Sham | Median | 53 | 7 | 0 | 4 |
| Operated | ST DEV | 35 | 12 | 1 | 3 |
| Control | Q1–Q3 | 17–89 | 2–21 | 0–1 | 1–7 |
| (n = 8) | | | | | |
| Desi- | Median | 45 | 13 | 0 | 4 |
| pramine | ST DEV | 24 | 7 | 0 | 3 |
| 7.5 mg/kg | Q1–Q3 | 35–68 | 9–19 | 0–0 | 3–7 |
| (n = 10) | | | | | |
| CI-988 | Median | 48 | 12 | 0 | 5 |
| 3.0 mg/kg | ST DEV | 11 | 5 | 0 | 3 |
| (n = 8) | Q1–Q3 | 42–61 | 8–16 | 0–0 | 2–6 |
| Olfactory | Median | 117** | 29* | 1 | 5 |
| Bulb- | ST DEV | 36 | 8 | 3 | 2 |
| ectomised | Q1–Q3 | 108–157 | 22–34 | 0–3 | 5–9 |
| Control | | | | | |
| (n = 9) | | | | | |
| Desi- | Median | 77++ | 27· | 0 | 6 |
| pramine | ST DEV | 13 | 6 | 1 | 2 |
| 7.5 mg/kg | Q1–Q3 | 63–83 | 21–32 | 0–1 | 5–9 |
| (n = 10) | | | | | |
| CI-988 | Median | 84* | 29 | 0 | 8 |
| 3.0 mg/kg | ST DEV | 24 | 7 | 1 | 1 |
| (n = 10) | Q1–Q3 | 69–107 | 18–31 | 0–1 | 7–9 |

*P <0.05
**P <0.01
+ = P <0.05
++ = P <0.01 Mann Whitney 'U' test
ST DEV = Standard Deviation
Q1–Q3 = Interquartile Range Table III shows the effects of CI-988 and desipramine in the open field test in sham operated and olfactory bulbectomised rats. CI-988 and desipramine both significantly reduced the hyperactivity associated with olfactory bulbectomy, indicating antidepressant activity.

Since the $CCK_B$ antagonist CI-988 exhibited activity in two art recognized models of depression, namely the behavioral despair (Porsolt) test and the olfactory bulbectomised rat test CCKs receptor antagonists will be effective in the treatment of depression in man.

Examples of formulations of the subject compounds and of salts thereof are illustrated by the following examples.

EXAMPLE 1

Injectables 1 mg to 100 mg/mL

CI-988

Water for Injection USP q.s.

The compound or a suitable salt thereof is dissolved in water and passed through a 0.2-micron filter. Aliquots of the filtered solution are added to ampoules or vials, sealed and sterilized.

EXAMPLE 2

Capsules 5 mg, 100 mg, 200 mg, 300 mg or 400 mg

CI-988, 250 g

Lactose USP, Anhydrous q.s. or 250 g

Sterotex Powder HM, 5 g

Combine the compound and the lactose in a tumble blend for 2 minutes, blend for 1 minute with the intensifier bar, and then tumble blend again for 1 minute. A portion of the blend is then mixed with the Sterotex Powder, passed through a #30 screen, and added back to the remainder of the blend. The mixed ingredients are then blended for 1 minute, blended with the intensifier bar for 30 seconds, and tumble blended for an additional minute. The appropriately sized capsules are filled with 141 mg, 352.5 mg, or 705 mg of the blend, respectively, for the 50 mg, 125 mg, and 250 mg containing capsules.

EXAMPLE 3

Tablets 50 mg, 100 mg, 200 mg, 300 mg, 400 mg, 500 mg or 600 mg

CI-988
Corn Starch NF, 200 g
Cellulose, Microcrystalline, 46 g
Sterotex Powder HM, 4 g
Purified Water q.s. or 300 mL Combine the corn starch, the cellulose, and the compound together in a planetary mixer and mix for 2 minutes. Add the water to this combination and mix for 1 minute. The resulting mix is spread on trays and dried in a hot air oven at 50° C. until a moisture level of 1 to 2 percent is obtained. The dried mix is then milled with a Fitzmill through a #RH2B screen, and added back to the milling mixture and the total blended for 5 minutes by drum rolling. Compressed tablets of 150 mg, 375 mg, and 750 mg, respectively, of the total mix are formed with appropriate sized punches the 50 mg, 125 mg, or 500 mg containing tablets.

I claim:

1. A method for the treatment of idiopathic depression which comprises administering to a mammal in need of such treatment a therapeutically effective amount of a compound in unit dosage form of formula

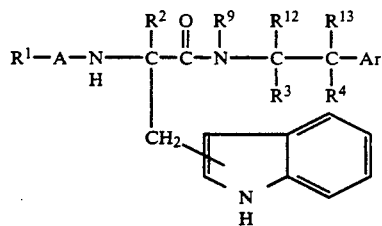

or a pharmaceutically acceptable salt thereof wherein:

$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and -$(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is —$(CH_2)_nCO$—, —$SO_2$—, —$S(=O)$—, —NHCO—,

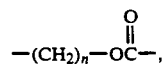

—SCO—, —O—$(CH_2)_nCO$— or —HC=CHCO— wherein n is an integer from zero to six;

$R^2$ is a straight or branched alkyl of from one to about six carbon atoms, —HC=$CH_2$, —C≡CH, —$CH_2$—CH=$CH_2$, —$CH_2C$≡CH, —$(CH_2)_nAr$, —$(CH_2)_nOR^*$, —$(CH_2)_nOAr$, —$(CH_2)_nCO_2R$, or —$(CH_2)_nNR^5R^6$ wherein n, R , $R^5$ and $R^6$ are as defined above and Ar is as defined below;

$R^3$ and $R^4$ are each independently selected from hydrogen, $R^2$ and —$(CH_2)_{n'}$—B—D wherein:

n' is an integer of from zero to three;

B is a bond,
—OCO$(CH_2)_n$—,
—O$(CH_2)_n$—,
—$SO_2NH(CH_2)_n$—,
—$NHSO_2(CH_2)_n$—,
—NHCO$(CH_2)_n$—,
—CONH$(CH_2)_n$—,
—NHCOCH=CH—,
—COO$(CH_2)_n$—,
—CO$(CH_2)_n$—,
—S—$(CH_2)_n$—,
—S(=O)—$(CH_2)_n$—,
—$SO_2$—$(CH_2)_n$—,
—CONH—C=C—,

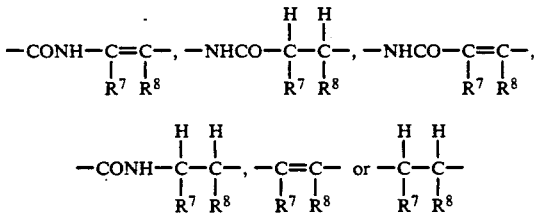

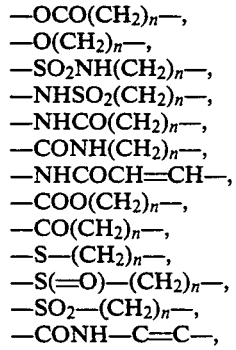

wherein $R^7$ and $R^8$ are independently selected from hydrogen and $R^2$ or together form a ring $(CH_2)_m$ wherein m is an integer of from 1 to 5 and n is as defined above;

D is
—COOR*,
—$CH_2OR^*$,
—$CHR^2OR^*$,
—$CH_2SR^*$,
—$CHR^2SR^*$,
—$CONR^5R^6$,
—CN,
—$NR^5R^6$,
—OH,
—H and acid replacements tetrazole, and

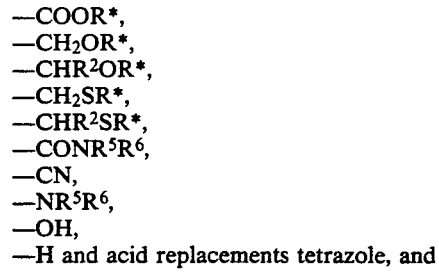

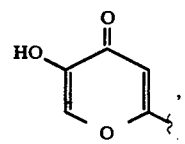
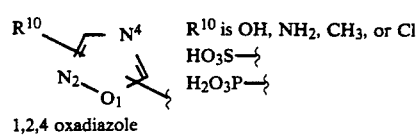

1,2,4 oxadiazole

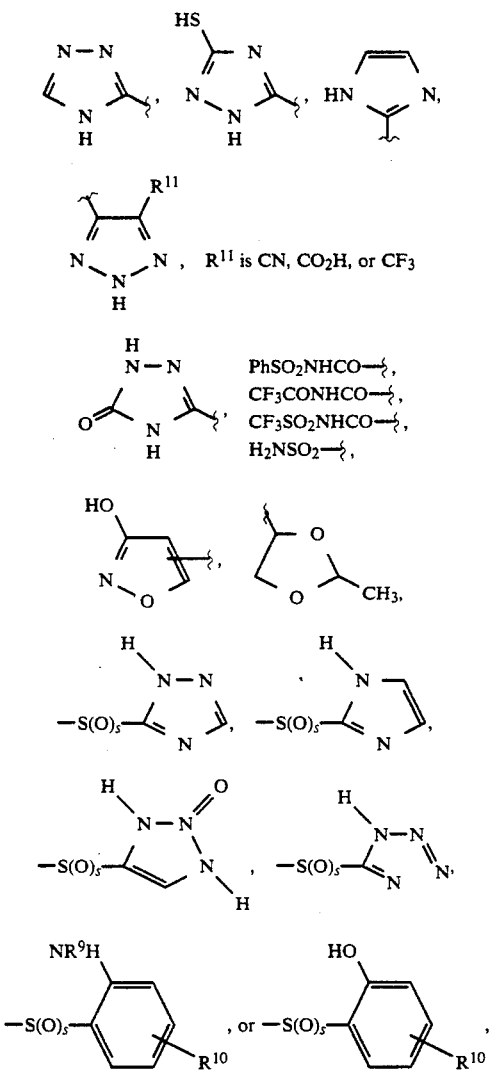

wherein R*, R², R⁵, and R⁶ are as defined above; R⁹ is hydrogen or a straight or branched alkyl of from one to about six carbon atoms, $-(CH_2)_nCO_2R^*$, $-(CH_2)_nOAr'$, $-(CH_2)_nAr'$ or $(CH_2)_nNR^5R^6$, wherein n, R*, R⁵, and R⁶ are as defined above or taken from R³ and Ar' is taken from Ar as defined below;

R¹² and R¹³ are each independently hydrogen or are each independently taken with R³ and R⁴ respectively to form a moiety doubly bonded to the carbon atom; and Ar is a mono- or polycyclic unsubstituted or substituted carbo- or heterocyclic aromatic or hydroaromatic moiety.

2. A method for the treatment of idiopathic depression which comprises administering to a mammal in need of such treatment a therapeutically effective amount of a compound in unit dosage form selected from:

1. [1S-[1α,2β[S*[S*(E)]],4α]]-4-[[2-[[3-(1H-indol -3-yl)-2-methyl-1-oxo-2-[[[(1,7,7-trimethyl-bicyclo[2.2.1-]hept-2-yl)oxy ]carbonyl]amino]propyl]amino]-1-phenylethyl]amino]-4-oxo-2-butenoic acid, 1.[1S-[1α,2β[S*(S*)],4α]]-4-[[2-[[3-(1H-indol-3-yl)-2-methyl-1-oxo-2-[[[(1,7,7-trimethyl-bicyclo[2.2.1]hept-2-yl)oxy]carbonyl]amino]propyl]methylamino]-1-phenylethyl]amino]-4-oxobutanoic acid, 3. [1S-[1α,2β[S*(S*)],4α]]-4-[[2-[[3-(1H-indol-3-yl-2-methyl-1-oxo-2-[[[(1,7,7-trimethyl-bicyclo[2.2.1]hept-2-yl)amino]carbonyl]amino ]propyl]amino]-1-phenylethyl]amino]-4-oxobutanoic acid, 4. [R-(R*,R*)]-4-[[2-[[3-(1H-indol-3-yl)-2-methyl-1-oxo-2-[(tricyclo [3.3.1.1³,⁷]dec-2-ylsulfonyl)amino]-propyl]amino]-1-phenyl-ethyl]amino]-4-oxobutanoic acid, 5. [R-(R*,S*)]-4-[[2-[[3-(1H-indol-3-yl)-2-methyl-1-oxo -2-[(tricyclo[3.3.1.1³,⁷]dec-2-ylsulfonyl)amino]-propyl]amino]-3-phenylpropyl]-amino]-4-oxobutanoic acid, 6. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl) -2-methyl-1-oxopropyl]amino]-3-phenylpropyl]amino]-4-oxobutanoic acid, 7. [1R-[1α[R*(S*)],2β]] and [1S-[1α[S*(R*)],2β]]-4-[[2-[[2-[[[(2-fluorocyclohexyl)oxy]carbonyl]amino]-3-(1H-indol-3-yl)-2-methyl-1-oxopropyl]methylamino]-3-phenylpropyl]amino]-4-oxobutanoic acid, 8. [1R-[1α[R*(S*)],2β]] and [1S[1α[S*(R*)],2β]]-4-[[2-[[3-(1H-indol-3-yl)-2-methyl-1-oxo-2-[[[[2-(trifluoromethyl) cyclohexyl]oxy]carbonyl]amino]-propyl]amino]-3-phenylpropyl]amino]-4-oxobutanoic acid, 9. [1R-[1α[R*(S*)],2β]] and 1S-[1α[S*(R*)],2β]]-4-[[2-[[3-(1H-indol-3-yl)-2-methyl-1-oxo-2-[[[[2-(trifluoromethyl)cyclohexyl]oxy]carbonyl]amino]-propyl]methylamino]-3-phenylpropyl ]amino]-4-oxobutanoic acid, 10. [R-(R*,S*)]-4-[[2-[[3-(1H-indol-3-yl)-2-methyl-1-oxo-2-[[(tricyclo[3.3.1.1³,⁷]dec-2-yloxy)carbonyl-]amino]propyl]methylamino]-3-phenylpropyl-]amino]-4-oxobutanoic acid, 11. [1S-[1α,2β[S*(R*)],4α]]-[1-(1H-indol-3-ylmethyl)-1-methyl -2-oxo-2-[[2-[[1-oxo-3-(1H-tetrazol-5-yl)propyl]amino]-1-(phenylmethyl) ethyl]amino]ethyl]carbamic acid, 1,7,7-trimethylbicyclo[2.2.1]hept-2-yl ester, 12. [1S-[1α,2β[S*,R*)]]-[1-(1H-indol-3-ylmethyl)1-methyl-2-oxo-2-[[2-[[1-oxo-3-(1H-tetrazol-5-yl)propyl]amino]-2-phenylethyl]amino]ethyl]carbamic acid, 1,7,7-trimethylbicyclo[2.2.1]hept-2-yl ester, 13. N-[2-methyl-N-[(tricyclo[3.3.1.1³,⁷]dec-2-yloxy)carbonyl]-D-tryptophyl]-L-phenylalanylglycine, 14. N-[2-methyl-N-[(tricyclo[3.3.1.1³,⁷ dec-2-yloxy)carbonyl]-D-tryptophyl]-L-phenylalanyl-β-alanine, 15. (R)-tricyclo[3.3.1.1³,⁷]dec-2-yl [1-(1H-indol-3-ylmethyl)-1-methyl-2-[methyl(2-phenylethyl)amino]-2-oxo-ethylcarbamate.

16. (±)-trans-2-chlorocyclohexyl [1-(1H-indol-3-ylmethyl)-1-methyl-2-oxo-2-[(2-phenylethyl)amino]ethyl]-carbamate, 17. 2-chorocyclohexyl [2-[[1-(hydroxymethyl)-2-phenylethyl]amino]-1-(1H-indol-3-ylmethyl)-1-methyl-2-oxoethyl]carbamate, 18. 2-[[2-[[[(2-chlorocyclohexyl)oxy]carbonyl]amino]-3-(1H-indol-3-yl)-2-methyl-1-oxopropyl]amino]-3-phenylpropyl butanedioate, 19. 2-[[2-[[[(2-methylcyclohexyl)oxy]carbonyl]-amino]-3-(1H-indol-3-yl)-2-methyl-1-oxopropyl]amino]-3-phenylpropyl butanedioate, 20. (±)-tricyclo[3.3.1.1³,⁷- dec-2-yl[1-(1H-indol-3-ylmethyl)-1-methyl-2-oxo-2-[(2-phenylethyl)amino]ethylcarbamate,
21. tricyclo[3.3.1.1³,⁷]dec-2-yl[2-[[1-(hydroxymethyl)-2-phenylethyl]amino]-1-(1H-indol-3-ylmethyl)-1-methyl-2-oxoethyl]carbamate,
22. 2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl butanedioate,
23. 2-[[3-(1H-indol-3-yl)-2-methyl-1-oxo-2-[[(tricyclo[3.3.1.1 ³,⁷]dec-2-yloxy)carbonyl]amino]propyl]amino]-1-phenylethyl butanedioate,
24. [1S-[1α,2β[S*(S*)],4α]]-4-[[2-[[3-(1H-indol-3-yl)-2-methyl-1-oxo-2-[[[(1,7,7-trimethylbicyclo-2.2.1]hept-2-yl)oxy]carbonyl]amino]propyl]amino]-1-phenylethyl]amino]-4-oxobutanoic acid,
25. [R-[R*,S*-(E)]]-4-[[2-[[3-(1H-indol-3-yl)-2-methyl-1-oxo-2-[[tricyclo[3.3.1.1³,⁷]dec-2-yloxy)carbonyl]amino]propyl]amino]-3-phenylpropyl]amino]-4-oxo-2-butenoic acid,
26. [R-(R*,S*)]-4-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-4-oxobutanoic acid,
27. (R)-tricyclo[3.3.1.1³,⁷]dec-2-yl [1-(1H-indol-3-ylmethyl)-1-methyl-2-[methyl(2-phenylethyl)amino]-2-oxoethylcarbamate,
28. [R-(R*,S*)]-[[2-[[3-(1H-indol-3-yl)-2-methyl-1-oxo-2-[[(tricyclo[3.3.1.1³,⁷]dec-2-yloxy)]carbonyl]amino]propyl]amino]-3-phenylpropyl]sulfinyl]acetic acid, ethyl ester,
29. [R-(R*,S*)]-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]sulfonyl]acetic acid, ethyl ester,
30. [R-(R*,S*)]-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]sulfinyl]acetic acid,
31. [R-[R*,R*-(E)]]-4-[[2-[[3-(1H-indol-3-yl)-2-methyl-1-oxo-2-[[(tricyclo[3.3.1.1³,⁷]dec-2-yloxy)]carbonyl]amino]propyl]amino]-1-phenylethyl]amino]-4-oxo-2-butenoic acid,
32. [R-(R*,S*)]-[[2-[[2-[3-(1H-indol-3-yl)-2-methyl-1-oxo-2-[[(tricyclo[3.3.1.1³,⁷]dec-2-yloxy)carbonyl]amino]propyl]amino]-3-phenylpropyl]thio]acetic acid,
33. [1S-[1α,2β[S*[S*(E)]],4β]]-4-[[2-[[3-(1H-indol-3-yl)-2-methyl-1-oxo-2-[[[(1,7,7-trimethylbicyclo[2.2.1]hept-2-yl)oxy]carbonyl]amino]propyl]amino]-1-phenylethyl]amino]-4-oxo-2-butenoic acid, methyl ester, (Bicyclo system is 1S-endo),
34. [1S-[1α,2β[S*[S*(E)]],4α]]-4-[[2-[[3-(1H-indol-3-yl)-2-methyl-1-oxo-2-[[[(1,7,7-trimethyl-bicyclo[2.2.1-]hept-2-yl)oxy]carbonyl]amino]propyl]amino]-1-phenylethyl]amino]-4-oxo-2-butenoic acid, (Bicyclo system is 1S-endo),
35. [R-(R*,R*)]-3-[[2-[[3-(1H-indol-3-yl)-2-methyl-1-oxo-3-[[(tricyclo[3.3.1.1³,⁷]dec-2-yloxy)]carbonyl]amino]propyl]amino]-1-phenylethyl ]amino]-3-oxopropanoic acid,
36. [R-(R*,S*)]-3-(1H-indol-3-ylmethyl)-3-methyl-4,10-dioxo-6-(phenylmethyl)-11-oxo-8-thia-2,5-diazatridecanoic acid, tricyclo[3.3.1.1³,⁷]-dec-2-yl or ester,
37. [R-(R*,S*)]-β-[[3-(1H-indol-3-yl)-2-methyl-1-oxo-2-[[(tricyclo[3.3.1.1³,⁷]dec-2-yloxy)]carbonyl]amino]propyl]amino]benzenebutanoic acid,
38. [R-(R*,S*)]-N-[3-[[3-(1H-indol-3-yl)-2-methyl-1-oxo-2-[[(tricyclo[3.3.1.1³,⁷]dec-2-yloxy)]carbonyl]amino]propyl]amino]-4-phenylbutyl]glycine,
39. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-4-oxo-2-butenoic acid,
40. mono [R-(R*,R*)]-2-[[3-(1H-indol-3-yl)2-methyl-1-oxo-2-[[(tricyclo[3.3.1.1³,⁷]dec-2-yloxy)carbonyl]amino]-1-phenylethyl butanedioate,
41. 3-[[3-[[3-(1H-indol-3-yl)-2-methyl-1-oxo-2-[[(tricyclo[3.31.1³,⁷]dec-2-yloxy)]carbonyl]amino]propyl]amino]-1-oxo-2-phenylpropyl]amino]propanoic acid (TRP is R, other center is RS),
42. [1R-[1α[R*(S*)],2β]]-4-[[2-[[3-(1H-indol-3-yl) -2-methyl-2-[[[(2-methyl-1-cyclohexyl)oxy]carbonyl]amino]-1-oxopropyl]amino]-3-phenylpropyl]amino]-4-oxo-2-butenoic acid, (−)-Isomer,
43. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]-4-oxobutanoic acid, (−)-Isomer,
44. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-2-butenoic acid, (−)-Isomer,
45. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl ]amino]-4-oxobutanoic acid, (−)-Isomer,
46. 2-methylcyclohexyl-[1R-[1α[R*(S*)]),2β)-[2-[[1-(hydroxymethyl) -2-phenylethyl]amino]-1-(1H-indol-3-ylmethyl)-1-methyl-2-oxoethyl]carbamate,
47. [R-[R*,S*-(E,E)]]-6-[[3-(1H-indol-3-yl)-2-methyl-1-oxo-2-[[(tricyclo[3.3.1.1³,⁷]dec-2-yloxy)carbonyl]amino]propyl]amino]-7-phenyl-2,4-heptadienoic acid,
48. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid,
49. tricyclo[3.3.1.1³,⁷]dec-2-yl-[S-[R*,S*-(E)]]12-(1H-indol-3-ylmethyl) -12-methyl-3,11-dioxo-9-(phenylmethyl)-2-oxa-7,10,13-triazatetradec-4-en-14-oate,
50. [R-(R*,S*)]-3-[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-3-oxopropanoic acid,
51. ethyl [R-(R*,S*)]-[[2-[[2-[3-(1H-indol-3-yl)-2-methyl-1-oxo-2-[[(tricyclo[3.3.1.1³,⁷]dec-2-yloxy)carbonyl]amino]propyl]amino]-3-phenylpropyl]thio]acetate,
52. [R-(R*,S*)]-β-[[3-(1H-indol-3-yl)-2-methyl-1-oxo-2-[[tricyclo[3.3.1.13,7]dec-2-yloxy)-carbonyl]amino]propyl]amino]-4-iodo-benzenebutanoic acid,
53. [R-(R*,R*)]-2-[[3-(1H-indol-3-yl)-2-methyl-1-oxo-2-[[(1(tricyclo[[(3.3.1.13,7]dec-2-yloxy)carbonyl]amino]propyl]amino]-1-phenylethoxy]acetic acid,
54. [[3-[[3-(1H-indol-3-yl)-2-methyl-1-oxo-3-[[tricyclo(3.3.1.1³,⁷]dec-2-yloxy)carbonyl]amino]propyl]amino]-1-oxo-2-phenylpropyl]amino]acetic acid (TRP center is R, other center is RS),
55. (R)-[[[2-[[3-(1H-indol-3-yl)-1-oxo-2-methyl-2-[[[(tricyclo[3.3.1.1 ³,⁷]dec-2-yloxy)carbonyl]amino]propyl]amino]-1-phenylethylidene]amino]oxy]acetic acid,
56. [R-(R*,S*)]-β-[[3-(1H-indol-3-yl)-2-methyl-1-oxo-2-[[(tricyclo[3.3.1.1 ³,⁷]dec-2-yloxy)carbonyl]amino]propyl]amino]benzenebutanoic acid, 57. [R-(R*,S*)]-N-[3-[[3-(1H-indol-3-yl)-2-methyl-1-oxo-2-[[(tricyclo[3.3.1.1³,⁷]dec-2-yloxy)carbonyl]propyl]amino]-4-phenylbutyl]glycine,
58. 2-[[[2-[[3-(1H-indol-3-yl)-2-methyl-1-oxo-2-[[(tricyclo[3.3.1.1 ³,⁷]dec-2-yloxy)carbonyl]amino]propyl]amino]-1-phenylethyl]amino]carbonyl]cyclopropanecarboxylic acid (cyclopropane ring is trans-(±), other centers are R),
59. carbamic acid, [1-(1H-indol-3-ylmethyl)-1-methyl-2-oxo-2-[[2-[[1-oxo-3-(1H-tetrazol-5-yl)propyl]amino]-2-phenylethyl]amino]ethyl-, tricyclo[3.3.1.1³,⁷]dec-2-yl ester, [R,(R*,S*)]-,
60. benzeneheptanoic acid, α-[[3-(1H-indol-3-yl)-2-methyl-1-oxo-2-[[(tricyclo[3.3.1.1³,⁷]dec-2-yloxy)carbonyl]amino]propyl]amino]-,[R-(R*,S*)]-,
61. methyl-(±)-β-[[(2-phenylethyl)amino]-carbonyl]-1β-[[(tricyclo[3.3.1.1 ³,⁷]dec-2-yloxy)carbonyl]amino]-1H-indole-3-butanoate,
62. [R-(R*,S*)]-4-[[2-(1H-indol-3-yl)-2-methyl-1-oxo-2-[[tricyclo[3.3.1.1³,⁷]dec-2-yloxycarbonyl]amino]propyl]amino]-3-phenylpropyl]amino]-4-oxo-2-butenoic acid,
63. bicyclo[2.2.1]heptane-2-acetic acid, 3-[[[[2-[[1-(hydroxymethyl)-2-phenylethyl]amino]1-(1H-indol-3-ylmethyl)-1-methyl-2-oxoethyl]amino]carbonyl]oxy]-4,7,7-trimethyl-, [1R-[1α,2β,3α[R*(S*)],4α]]-,
64. butanoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-[1R-1α[R*(R*)]2β]]-((−)-isomer),
65. 2-butenoic acid, 4-[[2-[[3-(1H-indol-3-yl)-2-methyl-2-[[[(2-methyl-1-cyclohexyl)oxy]carbonyl]amino]-1-oxopropyl]amino]-1-phenylethyl]amino]-4-oxo-, [1R-[1α[R*(R*)],2β]]-((−)-isomer),
66. butanoic acid, 4-[[2-[[3-(1H-indol-3-yl)-2-methyl-2-[[[(2-methyl-1-cyclohexyl)oxy]carbonyl]amino]-1-oxopropyl]amino]-3-phenylpropyl]amino]4-oxo-[1R-[1α[R*(S*)],2β]]-((−)-isomer), and
67. 2-butenoic acid, 4-[[2-[[3-(1H-indol-3-yl)2-methyl-2-[[[(2-methyl-1-cyclohexyl)oxy]carbonyl]amino]-1-oxopropyl]amino]-3-phenylpropyl]amino]-4-oxo-[1R[1α[R*(S*)],2β]]((−)-isomer).
68. [[3-[[3-(1H-indol-3-yl)-2-methyl-1-oxo-2-[[tricyclo[3.3.1.1 ³,⁷]dec-2-yloxy)carbonyl]amino]propyl]amino]-1-oxo-2-phenylpropyl]amino]acetic acid,
69. [R-(R*,R*)]-2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]acetic acid,
70. [1R-[1α,2β[R*(R*)]]]-2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropane carboxylic acid,
71. [1S-[1α,2β[S*(S*)]]]-2-[[[2-[[3-(1H-indol-3-yl)-2-methyl -1-oxo-2-[[(tricyclo[3.3.1.1³,⁷]dec-2-yloxy)carbonyl]amino]propyl]amino]-1-phenylethyl]amino]carbonyl]cyclopropane carboxylic acid,
72. [R-R*,R*)]-3-[2-[[3-(1H-indol-3-yl)-2-methyl-1-oxo-2-[[(tricyclo[3.3.1.1³,⁷]dec-2-yloxy)carbonyl]amino]propyl]amino]-1-phenylethoxy]propanoic acid,
73. [R-(R*,R*)]-mono 2-[[3-(1H-indol-3-yl)-2-methyl-1-oxo-2-[[(tricyclo[3.3.1.1³,⁷]dec-2-yloxy)carbonyl]amino]-1-phenylethyl butanedioic acid,
74. 3-[[3-[[3-(1H-indol-3-yl)-2-methyl-1-oxo-2-[[(tricyclo[3.3.1.1³,⁷ ]dec-2-yloxy)carbonyl]amino]propyl]amino]-1-oxo-2-phenylpropyl]amino]propanoic acid,
75. [R-(R*,S*)]-β-[[3-(1H-indol-3-yl)-2-methyl-1-oxo-2-[[(tricyclo[3.3.1.1³,⁷]dec-2-yloxy)carbonyl]amino]propyl]amino]-4-iodobenzenebutanoic acid,
76. [1R-[1α[R*(S*)],2β]]-4-[[2-[[3-(1H-indol-3-yl)-2-methyl -2-[[[(2-methyl-1-cyclohexyl)oxy]carbonyl amino]-1-oxopropyl]amino]-3-phenylpropyl ]amino]-4-oxo-2-butenoic acid,
77. [1R-[1α[R*(S*)],2β]]-4-[[2-[[3-(1H-indol-3-yl)-2-methyl-2-[[[(2-methyl-1-cyclohexyl)oxy]carbonyl]amino]-1-oxopropyl]amino]-3-phenylpropyl ]amino]-4-oxobutanoic acid, ((−)-isomer),
78. [1R-[1α[R*(R*)],2β]]-4-[[2-[[3-(1H-indol-3-yl)-2-methyl-2-[[[(2-methyl-1-cyclohexyl)oxy]carbonyl]amino]-1-oxopropyl]amino]-1-phenylethyl ]amino]-4-oxo-2-butenoic acid,
79. 1R-[1α[R*(R*)],2β]]-4-[[2-[[3-(1H-indol-3-yl) -2-methyl-2-[[[(2-methyl-1-cyclohexyl)oxy]carbonyl]amino]-1-oxopropyl]amino]-1-phenylethyl]amino]-4-oxobutanoic acid, ((−)-isomer),
80. [R-(R*,S*)]-lg/-[[3-(1H-indol-3-yl)-2-methyl-1-oxo-2-[[(tricyclo[3.3.1.1³,⁷]dec-2-yloxy)carbonyl]amino]propyl]amino]benzeneheptanoic acid,
81. 2-[[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]carbonyl]cyclopropanecarboxylic acid (cyclopropyl ring is trans-(±), other centers are R),
82. 2-methylcyclohexyl [1R-[1α[R*(S*)]],2β]-[[1-(hydroxymethyl) -2-phenylethyl]amino]-1-(1H-indol-3-ylmethyl)-1-methyl-2-oxoethyl]carbamate,
83. [R-[R*,S*-(E<E)[[-6-[[3-(1H-indol-3-yl)-2-methyl-1-oxo-2-[[(tricyclo[3.3.1.1³,⁷]dec-2-yloxy)carbonyl]amino]propyl]amino]-7-phenyl-2,4-heptadienoic acid,
84. tricyclo[3.3.1.1³,⁷]dec-2-yl [2-[[1-(hydroxymethyl)-2-hydroxy-2-phenylethyl]amino]-1-(1H-indol-3-ylmethyl)-1-methylethyl]carbamate,
85. tricyclo[3.3.1.1³,⁷]dec-2-yl [R-(R*,R*)]-[1-(1H-indol-3-ylmethyl) -1-methyl-2-oxo-2-[[2-[[1-oxo-3-(1H-tetrazol-5-yl)propyl]amino]-2-phenylethyl]amino]ethyl]carbamate,
86. [R-(R*,S*)]-2-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]sulfinyl]acetic acid,
87. [R-(R*,S*)]-[[2-[[3-(1H-indol-3-yl)-2-methyl-1-oxo-2-[[(tricyclo[3.3.1.1³,⁷]dec-2-yloxy)]carbonyl]amino]propyl]amino]-3-phenylpropyl]sulfonyl]acetic acid,
88. ethyl [R-(R*,S*)]-[[2-[[3-(1H-indol-3-yl)-2-methyl-1-oxo-2-[[(tricyclo[3.3.1.1³,⁷]dec-2-yloxy)]carbonyl]amino]propyl]amino]-3-phenylpropyl]sulfonyl]acetate,
89. 2-chlorocyclohexyl [2-[[1-(hydroxymethyl)-2-phenylethyl]amino]-1-(1H-indol-3-ylmethyl)-1-methyl-2-oxoethyl]carbamate.
90. [R-[R*,R*(E)]]-4-[[2-[[3-(1H-indol-3-yl)-2-methyl-1-oxo-2 -[[(tricyclo[3.3.1.1³,⁷]dec-2-ylamino)carbonyl]amino]propyl]amino]-1-phenylethyl]amino]-4-oxo-2-butenoic acid,
91. [R-(R*,R*)]-4-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]-4-oxobutanoic acid,
92. [R-(R*,S*)]-mono[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]butanedioate,
93. tricyclo[3.3.1.1³,⁷]dec-2-yl [R-(R*,S*)-[2-[[1-(hydroxymethyl)-2-phenylethyl]amino]-1-(1H-indol-3-ylmethyl)-1-methyl-2-oxoethyl]carbamate,
94. [1S-[1α,2β[S*[S(E)]],4α]]-4-[[2-[[3-(1H-indol-3-yl)-2-methyl-1-oxo-2-[[[(1,7,7-trimethylbicyclo[2.2.1-

]hept-2-yl)oxy]-carbonyl]amino]propyl]amino]-1-phenylethyl]amino]-4-oxo-2-butenoic acid, 95. [1S-[1α,2β[S*(S*)],4α]]-4-[[2-[[3-(1H-indol-3-yl)-2-methyl-1-oxo-[[[(1,7,7-trimethylbicyclo[2.2.1-]hept-2-yl)oxy]carbonyl]amino]propyl]amino]-1-phenylethyl]amino]-4-oxo-2-butenoic acid, (bicyclo system is 1S-endo), 96. [R-[R*,S*-(E)]]-4-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-4-oxo-2-butenoic acid, 97. N-[2-methyl-N-[(tricyclo[3.3.1.1³,⁷]dec-2-yloxy)carbonyl]-D-tryptophyl]-L-phenylalanylglycine, 98. [R-(R*,S*)[-4-[[2-[[3-(1H-indol-3-yl)-2-methyl-1-oxo-2-[[(tricyclo[3.3.1.1³,⁷]dec-2-yloxy)carbonyl]amino]propyl]amino]-3-phenyl-propyl]amino]-4-oxobutanoic acid, 99. [R-(R*,R*)]-2-[[2-[[1,4-dioxo-4-(1H-tetrazol-5-ylamino)butyl]amino]-2-phenylethyl]amino]-1-(1H-indol-3-ylmethyl)-1-methyl-2-oxoethyl]carbamic acid, 100. [R-(R*,R*)]-3-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]-3-oxopropanoic acid, 101. [R-(R*,S*)]-3-[[2-[[3-(1H-indol-3-yl)-2-methyl-1-oxo-2-[[(tricyclo[3.3.1.13,7]dec-2-yloxy)carbonyl]amino]propyl]amino]-3-phenylpropyl]amino ]-3-oxopropanoic acid, 102. [R-[R*,S*-(E)]]-4-[[2-[[3-(1H-indol-3-yl)-2-methyl-2-[[(bicyclo[3.3.1]non-9-yloxy)carbonyl]amino]-1-oxopropyl]amino]-3-phenylpropyl]amino]-4-oxo-2-butenoic acid, 103. [R-(R*,S*)]-5-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]amino]-5-oxopentanoic acid, 104. ethyl [R-(R*,S*)]-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]sulfinyl]acetate, 105. [R-[R*,R*-(E)]]-4-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino ]-4-oxo-2-butenoic acid, 106. [R-(R*,S*)]-N-[3-[[3-(1H-indol-3-yl)-2-methyl-1-oxo-2-[[(tricyclo[3.3.1.1³,⁷]dec-2-yloxy)carbonyl]amino]propyl]amino]-1-oxo-4-phenylbutyl]-β-alanine, 107. N-[N-[α-methyl-N-[(tricyclo[3.3.1.1³,⁷]dec-2-yloxy)carbonyl]-D-tryotophyl]-L-phenylalanyl]-L-alanine, 108. [R-R*,S*)]-3-[[2-[[3-(1H-indol-3-yl)-2-methyl-1-oxo-2-[[(tricyclo[3.3.1.1³,⁷]dec-2-yloxy)carbonyl]amino]propyl]amino]-3-phenylpropyl]thio]-propanoic acid, 109. [R-(R*,S*)]-[[2-[[2-[3-(1H-indol-3-yl)-2-methyl-1-oxo-2-[[(tricyclo[3.3.1.1³,⁷]dec-2-yloxy)carbonyl]amino]propyl]amion]-3-phenylpropyl]thio]acetic acid, 110. [R-(R*,S*)]-β-[[3-(1H-indol-3-yl)-2-methyl-1-oxo-2-[[(tricyclo[3.3.1.1³,⁷]dec-2-yloxy)carbonyl]amino]-propyl]amino]benzenebutanoic acid, 111. tricyclo[3.3.1.1³,⁷]dec-2-yl [R-(R*,S*)]-3-(1H-indol-3-ylmethyl)-3-methyl-4,10-dioxo-6-(phenylmethyl)-11-oxa-8-thia-2,5-diazatridecanoic acid, 112. [2-[[2-hydroxy-1-(hydroxymethyl)-2-phenylethyl]amino]-1-(hydroxymethyl)-1-(1H-indol-3-yl-methyl)-2-oxoethyl]-, tricyclo[3.3.1.1³,⁷]dec-2-yl ester, 113. N-[α-methyl-N-[(tricyclo[3.3.1.1³,⁷]dec-2-yloxy)-carbonyl]-L-tryptophyl]-D-3-(phenylmethyl)-β-alanine, 114. (1R-trans)-N-[α-methyl-N-[[(2-methylcyclohexyl)oxy]carbonyl]-L-tryptophyl]-D-3-(phenylmethyl) ((1R,2R)-N-[[(2-methylcyclohexyl)oxy]carbonyl]-)(α/-Me)LTrp-(D-3-Bzl)bAla-β-alanine ((−)-isomer), and 115. (1S-trans)-N-[α-methyl-N-[[(2-methylcyclohexyl)oxy]carbonyl]-D-tryptophyl]-L-3-(phenylmethyl)-β-alanine.

3. A method according to claim 1 wherein the compound administered is [R-(R*,R*)]-4-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]-4-oxobutanoic acid or a pharmaceutically acceptable salt thereof.

4. A method according to claim 1 wherein an individual dose of 5 mg to 50 mg parenterally or of 5 mg to 600 mg enterally of the compound or a pharmaceutically acceptable salt thereof is administered.

5. A method for the treatment of idiopathic depression which comprises administering to a mammal in need of such treatment a therapeutically effective amount of a compound in unit dosage form of formula

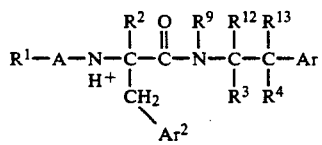

or a pharmaceutically acceptable salt thereof wherein:
$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and $-(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is $-(CH_2)_nCO-$, $-SO_2-$, $-S(=O)-$, $-NHCO-$,

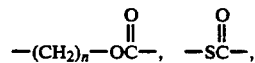

$-O-(CH_2)_nCO-$, or $-HC=CHCO-$ wherein n is an integer from zero to six;

$R^2$ is a straight or branched alkyl of from one to about six carbon atoms, $-HC=CH_2$, $-C\equiv CH$, $-(CH_2)_n-CH=CH_2$, $-(CH_2)_nC\equiv CH$, $-(CH_2)_nAr$, $-(CH_2)_nOR^*$, $-(CH_2)_nOAr$, $-(CH_2)_nCO_2R^*$, or $-(CH_2)_nNR^5R^6$ wherein n, R*, $R^5$, and $R^6$ are as defined above and Ar is as defined below;

$R^3$ and $R^4$ are each independently selected from hydrogen, $R^2$ and $-(CH_2)_n,-B-D$ wherein:
n' is an integer of from zero to three;
B is a bond,
  $-OCO(CH_2)_n-$,
  $-O(CH_2)_n-$, —NHCO(CH$_2$)$_n$—,
—CONH(CH$_2$)$_n$—,
—NHCOCH=CH—,
—COO(CH$_2$)$_n$—,
—CO(CH$_2$)$_n$—,
—S—(CH$_2$)$_n$—
—S(=O)—(CH$_2$)$_n$—,
—SO$_2$—(CH$_2$)$_n$—,
—NHSO$_2$—(CH$_2$)$_n$—,
—SO$_2$NH(CH$_2$)$_n$—, $$\text{NHCO}-\underset{R^7}{\underset{|}{C}}=\underset{R^8}{\underset{|}{C}}-,$$

$$\text{CONH}-\underset{R^7}{\underset{|}{C}}=\underset{R^8}{\underset{|}{C}}-,$$

$$\text{NHCO}-\underset{R^7}{\overset{H}{\underset{|}{C}}}-\underset{R^8}{\overset{H}{\underset{|}{C}}}-,$$

$$\text{CONH}-\underset{R^7}{\overset{H}{\underset{|}{C}}}-\underset{R^8}{\overset{H}{\underset{|}{C}}}-,$$

wherein R$^7$ or R$^8$ are independently selected from hydrogen and R$_2$ or together form a ring (CH$_2$)$_m$ wherein m is an integer of from 1 to 5 and n is as defined above;

D is
—COOR*,
—CH$_2$OR*,
—CHR$^2$OR*,
—CH$_2$SR*,
—CHR$^2$SR*,
—CONR$^5$R$^6$,
—CN,
—NR$^5$R$^6$,
—OH,
—H and acid replacements such as tetrazole

[tetrazole structure]

[HO-pyranone structure]

[1,2,4 oxadiazole structure], R$^{10}$ is OH, NH$_2$, CH$_3$ or Cl
HO$_3$S—,
—PO$_3$H$_2$

[triazole, thiol-triazine, imidazole structures]

[pyrazole structure with R$^{11}$], R$^{11}$ is CN, CO$_2$H, or CF$_3$,

[cyclic urea structure]
PhSO$_2$NHCO—,
CF$_3$CONHCO—,
CF$_3$SO$_2$NHCO—,
H$_2$NSO$_2$—,

[hydroxyisoxazole structure], [dioxolane structure],

—S(O)$_m$—[triazole], —S(O)$_m$—[imidazole],

—S(O)$_m$—[imidazolone], —S(O)$_m$—[tetrazole],

—S(O)$_m$—[aniline with NR$^5$H and R$^{10}$], —S(O)$_m$—[phenol with R$^{10}$], wherein m is an integer of from 0 to 2, wherein R*, R$^2$, R$^5$, and R$^6$ are as defined above;

R$^9$ is hydrogen or a straight or branched alkyl of from one to about six carbon atoms, —(CH$_2$)$_n$CO$_2$R*, —(CH$_2$)$_n$OAr′, —(CH$_2$)$_n$NR$^5$R$^6$, wherein n, R*, R$^5$, and R$^6$ are as defined above or taken from R$^3$ and Ar′ is taken from Ar as defined below;

R$^{12}$ and R$^{13}$ are each independently hydrogen or are each independently taken with R$^3$ and R$^4$, respectively, to form a moiety doubly bonded to the carbon atom;

Ar is a mono- or polycyclic unsubstituted or substituted carbo- or heteroaromatic or carbo- or heterohydroaromatic moiety; and Ar$^2$ can be selected from Ar as defined above or the CH$_2$Ar$^2$ moiety of formula I is the sidechain of a biologically significant amino acid, with the proviso that Ar$^2$ cannot be

[indole structure];

Ar$^2$ is also —(CH$_2$)$_2$NHC(=NH)NHNO$_2$, —(CH$_2$)$_2$NMe$_2$, or —CH$_2$CO$_2$CH$_3$.

6. A method for the treatment of idiopathic depression which comprises administering to a mammal in need of such treatment a therapeutically effective amount of a compound selected from:

Tricyclo[3.3.1.1³,⁷]dec-2-yl[2-[[1-(hydroxymethyl)-2-phenylethyl]amino]-1-methyl-2-oxo-1-(9H-pyrido[3,4-b]indol-3-ylmethyl)ethyl]-carbamate (alanine center is RS, other center is S), Tricyclo[3.3.1.1³,⁷]dec-2-yl[1-methyl-1-[[9-(methylsulfonyl)-9H-pyrido[3,4-b]indol-3-yl]methyl]-2-oxo-2-[(2-phenylethyl)amino]ethyl]-carbamate, Tricyclo[3.3.1.1³,⁷]dec-2-yl[2-[[1-(hydroxymethyl)-2-phenylethyl]amino]-1-methyl-1-[[9-(methylsulfonyl)-9H-pyrido[3,4-b]indol-3-yl]methyl]-2-oxoethyl]carbamate (phenylmethyl center S, other center RS), Tricyclo[3.3.1.1³,⁷]dec-2-yl[2-[[1-(hydroxymethyl)-2-phenylethyl]amino]-1-methyl-1-(1-naphthalenylmethyl)-2-oxoethyl]carbamate (naphthalenylmethyl center is RS, other center is S), Tricyclo[3.3.1.1³,⁷]dec-2-yl[2-[[1-hydroxymethyl)-2-phenylethyl]amino]-1-methyl-1-(2-naphthalenylmethyl)-2-oxoethyl]carbamate (naphthalene center is RS, hydroxymethyl center is S), Tricyclo[3.3.1.1³,⁷]dec-2-yl(±)-[1-methyl-1-(1-naphthalenylmethyl)-2-oxo-2-[(2-phenylethyl) -amino]ethyl]carbamate, Tricyclo[3.3.1.1³,⁷]dec-2-yl(±)-[1-methyl-1-(2-naphthalenylmethyl)-2-oxo-2-[(2-phenylethyl) -amino]ethyl]carbamate, Tricyclo[3.3.1.1³,⁷]dec-2-yl[2-[[1-(hydroxymethyl)-2-phenylethyl]amino]-1-methyl-1-(2-naphthalenylmethyl)-2-oxoethyl]carbamate (hydroxy center is S, other center is R or S) (Isomer I), Tricyclo[3.3.1.1³,⁷]dec-2-yl(±)[1-(3-benzofuranylmethyl)-1-methyl-2-oxo-2-[(2-phenylethyl)amino]ethyl]-carbamate, Tricyclo[3.3.1.1³,⁷]dec-2-yl[1-(3-benzofuranylmethyl)-2-[[1-(hydroxymethyl)-2-phenylethyl]amino]-1-methyl-2-oxoethyl[carbamate (benzofuranylmethyl center is RS, other center is S), Tricyclo[3.3.1.1³,⁷]dec-2-yl[1-[(2-bromo-3-benzofuranyl)methyl]-2-[[1-(hydroxymethyl)-2-phenylethyl]amino]-1-methyl-2-oxoethyl]carbamate (benzofuran center is RS, hydroxymethyl center is S), Tricyclo[3.3.1.1³,⁷]dec-2-yl(±)-[1-[(2-bromo -3-benzofuranyl)methyl]-1-methyl-2-oxo-2-[(2-phenylethyl)amino]ethyl]carbamate, 2-Methylpropyl 2-[[2-methyl-1-oxo-3-(3-pyridinyl)-2-[[(tricyclo[3.3.1.1³,⁷]dec-2-yloxy)carbonyl]amino]propyl]amino]-3-phenylpropyl carbonate (pyridine center is RS, other center is S), Tricyclo[3.3.1.1³,⁷]dec-2-yl[2-[[1-hydroxymethyl)-2-phenylethyl]amino]-1-methyl-2-oxo-1-(3-pyridinylmethyl)ethyl]carbamate (hydroxymethyl center is S, other is (±)) (Diastereomer I), Tricyclo[3.3.1.1³,⁷]dec-2-yl(±)-[1-methyl-2-oxo-2-[(2-phenylethyl)amino]-1-(4-pyridinyl -methyl)ethyl]carbamate, Tricyclo[3.3.1.1³,⁷]dec-2-yl [2-[[1-(hydroxymethyl)-2-phenylethyl]amino]-1-methyl-2-oxo-1-(2-pyridinylmethyl)ethyl]carbamate (hydroxymethyl center is S, other center is R or S) (Diastereomer I), Tricyclo[3.3.1.1³,⁷]dec-2-yl(±)-[1-methyl-2-oxo-2-[(2-phenylethyl)amino]-1-(2-pyridinyl) -methyl)ethyl]carbamate, Tricyclo[3.3.1.1³,⁷]dec-2-yl(±)-[1-[(2-aminophenyl)methyl]-1-methyl-2-oxo-2-[(2-phenylethyl)amino]ethyl]carbamate, Tricyclo[3.3.1.1³,⁷]dec-2-yl(±)-[1-[(2-hydroxyphenyl)methyl]-1-methyl-2-oxo-2-[(2-phenylethyl)amino]ethyl]carbamate, Tricyclo[3.3.1.1³,⁷]dec-2-yl(±)-[1-methyl-2-oxo-2-[(2-phenylethyl)amino]-1-[(2-quinolinyl)methyl]ethyl]-carbamate, Tricyclo[3.3.1.1³,⁷]dec-2-yl[2-[[1-(hydroxymethyl)-2-phenylethyl]amino]-1-methyl-2-oxo-1-(4-quinolinylmethyl)ethyl]carbamate (hydroxymethyl center is S, other center is RS), Tricyclo[3 3.1.1³,⁷]dec-2-yl)(±)-[1-methyl-2-oxo-2-[(2-phenylethyl)-amino]-1-(4-quinolinylmethyl)ethyl]-carbamic acid, Tricyclo[3.3.1.1³,⁷]dec-2-yl(±)-[1-methyl-2-oxo-2-[(2-phenylmethyl)amino]-1-(3-quinolinylmethyl)ethyl]-carbamate, Tricyclo[3.3.1.1³,⁷]dec-2-yl[2-[[1-(hydroxymethyl)-2-phenylethyl]amino]-1-methyl-2-oxo-1-(2-quinolinylmethyl)ethyl[carbamate (alanine center is RS, other center is S), Tricyclo[3.3.1.1³,⁷]dec-2-yl [2-[(2-amino-2-phenylethyl)amino]-1-(1H-indazol-3-ylmethyl)-1-methyl-2-oxoethyl]carbamate, 4-[[2-[[2-methyl-1-oxo-3-(1,2,3,4-tetrahydro-2-quinolinyl)-2-[[(tricyclo-2-[3.3.1.1³,⁷]dec-2-yloxy)carbonyl]amino]propyl]amino]-1-phenylethyl]amino]-4-oxobutanoic acid compd. with 1-deoxy-1-(methylamino)-D-glucitol, 4-[[2-[[3-(1,2-dihydro-2-quinolinyl)-2-methyl-1-oxo-2-[[(tricyclo[3.3.1.1³,⁷]dec-2-yloxy)carbonyl]amino]propyl]amino]-1-phenylethyl]amino]-4-oxobutanoic acid compd. with 1-deoxy-1-(methylamino)-D-glucitol, 4-[[2-[[2-methyl-1-oxo-3-(4-quinolinyl)-2-[[(tricyclo[3.3.1.1³,⁷]dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1³,⁷]dec-2-yl(±)-[1-(1H-indazol-3-ylmethyl)-1-methyl-2-oxo-2-[(2-phenylethyl)amino]ethyl]-carbamate, Tricyclo[3.3.1.1³,⁷]dec-2-yl[2-[[1-(hydroxymethyl)-2-phenylethyl]amino]-1-(1H-indazol-3-ylmethyl)-1-methyl-2-oxoethyl]carbamate (hydroxymethyl center is S, other center is RS), 4-[[2-[3-(1H-indazol-3-yl)-2-methyl-1-oxo-2-[[(tricyclo[3.3.1.1³,⁷]dec-2-yloxy)carbonyl]amino]-propyl]amino]-1-phenylethyl]amino]-4-oxobutanoic acid (mixture of isomers), Tricyclo[3.3.1.1³,⁷]dec-2-yl(±)-1-[1-(1H-benzimidazol-2-ylmethyl)-1-methyl-2-oxo-2-[(2-phenylethyl)amino]ethyl]carbamate, Tricyclo[3.3.1.1³,⁷]dec-2-yl[1-(1H-benzimidazol-2-ylmethyl)-2-[[1-(hydroxymethyl)-2-phenylethyl]amino]-1-methyl-2-oxoethyl]carbamate (hydroxy center is S, other center is RS), Tricyclo[3.3.1.1³,⁷]dec-2-yl[1-(benzo[b]thien-3-ylmethyl)-2-[[1-(hydroxymethyl)-2-phenylethyl]amino]-1-methyl-2-oxoethyl]carbamate (benzothiophene center is RS, hydroxymethyl center is S), Tricyclo[3.3.1.1³,⁷]dec-2-yl(±)-[1-(benzo[b]thien-3-ylmethyl)-1-methyl-2-oxo-2-[(2-phenylethyl)amino]ethyl]carbamate, Tricyclo[3.3.1.1³,⁷]dec-2-yl-(R or S,R)-[2-[[2-(2,5-dioxo-1-pyrrolidinyl)-2-phenylethyl]amino]-1-(1H-indazol-3-ylmethyl)-1-methyl-2-oxoethyl]carbamate, Tricyclo[3.3.1.1³,⁷]dec-2-yl-(S or R,R)-[2-[[2-(2,5-dioxo-1-pyrrolidinyl)-2-phenylethyl]amino]-1-(1H-indazol-3-ylmethyl)-1-methyl-2-oxoethyl]carbamate, Tricyclo[3.3.1.1³,⁷]dec-2-yl [2-[[2-hydroxy-1-(hydroxymethyl)-2-phenylethyl]amino]-1-methyl-2-oxo-1-[[4-(phenylmethoxy)phenyl]methyl]ethyl]carbamate, Tricyclo[3.3.1.1³,⁷]dec-2-yl [2-[[2-hydroxy-(hydroxymethyl)-2-phenylethyl]amino]-1-[(4-hydroxyphenyl)methyl]-1-methyl-2-oxoethyl]carbamate (Mixture of [1S-[1R*(R*),2R*]] and [1S-[1R*(S*),2R*]] isomers), Tricyclo[3.3.1.1³,⁷]dec-2-yl [2-[[2-hydroxy-1-(hydroxymethyl)-2-phenylethyl]amino]-1-[(4-methoxyphenyl)methyl]-1-methyl-2-oxoethyl]carbamate (Mixture of [1S-[1R*(R*),2R*)]] and [1S-[1R*(S*),2R*]] isomers), Tricyclo[3.3.1.1³,⁷]dec-1-yl [2-[[2-hydroxy-1-(hydroxymethyl)-2-phenylethyl]amino]-1-methyl-2-oxo-1-[[4-(phenylmethoxy)phenyl]methyl]ethyl]carbamate (Mixture of [1S-[1R*(R*),2R*]] and [1S-[1R*(S*),2R*]] isomers), Tricyclo[3.3.1.1³,⁷]dec-2-yl (±)-[1-[(3,5-dimethyl-4-isoxazolyl)methyl]-1-methyl-2-oxo-2-[(2-phenylethyl)amino]ethyl]carbamate, Tricyclo[3.3.1.1³,⁷]dec-2-yl (±)-[1-[[2-(acetylamino)-4-thiazolyl]methyl]-1-methyl-2-oxo-2-[(2-phenylethyl)amino]ethyl]carbamate, Tricyclo[3.3.1.1³,⁷]dec-2-yl (±)-[1-(1H-benzotriazol-1-ylmethyl)-1-methyl-2-oxo-2-[(2-phenylethyl)amino]ethyl]carbamate, Tricyclo[3.3.1.1³,⁷]dec-2-yl (RS,S) [2-[[1-(hydroxymethyl)-2-phenylethyl]amino]-1-methyl-2-oxo-1-[[4-(1,2,3-thiadiazol-4-yl)phenyl]methyl]ethyl]carbamate, Tricyclo[3.3.1.1³,⁷]dec-2-yl (S or R, S)-[2-[[2-hydroxy-1-(hydroxymethyl)-2-phenylethyl]amino]-1-methyl-2-oxo-1-[[4-(1,2,3-thiadiazol-4-yl)phenyl]methyl]ethyl]carbamate, Tricyclo[3.3.1.1³,⁷]dec-2-yl-(S or R,R)-[2-[[2-(2,5-dioxo-1-pyrrolidinyl)-2-phenylethyl]amino]-1-(1H-indazol-3-ylmethyl)-1-methyl-2-oxoethyl]carbamate, 4-[[2-[[2-Methyl-1-oxo-3-(4-pyridinyl)-2-[[(tricyclo[3.3.1.1³,⁷]dec-2-yloxy)carbonyl]amino]propyl]amino]-1-phenylethyl]amino]-4-oxobutanoic acid, 4-[[2-[[3-(2,3-dihydro-1-methyl-5-phenyl-1H-benzodiazepin-2-yl)-2-methyl-1-oxo-2-[[(tricyclo[3.3.1.1³,⁷]-dec-2-yloxy)carbonyl]amino]propyl]amino]-1-phenylethyl]amino]-4-oxobutanoic acid compd. with 1-deoxy-1-(methylamino)-D-glucitol, Tricyclo[3.3.1.1³,⁷]dec-2-yl [2-[[1-(hydroxymethyl)-2-phenylethyl]amino]-1-methyl-2-oxo-1-(2-pyridinylmethyl)ethyl]carbamate, N-oxide, Tricyclo[3.3.1.1³,⁷]dec-2-yl [1-[(2,3-dihydro-1-methyl-5-phenyl-1H-1,4-benzodiazepin-2-yl)methyl]-1-methyl-2-[(2-phenylethyl)amino]-2-oxoethyl]carbamate, Tricyclo[3.3.1.1³,⁷]dec-2-yl [2-[[1-hydroxymethyl)-2-phenylethyl]amino]-1-methyl-2-oxo-1-(4-pyridinylmethyl)ethyl]carbamate, Tricyclo[3.3.1.1³,⁷]dec-2-yl (±)-[1-methyl-2-oxo-2-[(2-phenylethyl)amino]-1-[(5,6,7,8-tetrahydro-5,5,8,8-tetramethyl-2-naphthalenyl)methyl]ethyl]carbamate, Tricyclo[3.3.1.1³,⁷]dec-2-yl [1S-[1R*(R or S),2R*]]-[2-[[2-hydroxy-1-(hydroxymethyl)-2-phenylethyl]amino]-1-methyl-2-oxo-1-(1H-pyrrolo[2,3-b]pyridin-3-ylmethyl)ethyl]carbamate, Tricyclo[3.3.1.1³,⁷] [1S-[1R*(S or R),2R*]][2-[[2-hydroxy-1-(hydroxymethyl)-2-phenylethyl]amino]-1-methyl-2-oxo-1-(1H-pyrrolo[2,3-b]pyridin-3-ylmethyl)ethyl]carbamate, Tricyclo[3.3.1.1³,⁷]dec-2-yl [1S-[1R*(R or S),2R*]]-[2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate, Tricyclo[3.3.1.1³,⁷] [1S-[1R*(S or R),2R*]][2-[[2-hydroxy-1-(hydroxymethyl)-2-phenylethyl]amino]-1-methyl-2-oxo-1-(1H-pyrrolo[3,2-c]pyridin-3-ylmethyl)ethyl]carbamate, Carbamic acid, [-[(2,3-dimethyl)-1H-pyrrol-4-ylmethyl]-1-methyl-2-oxo-2-[(2-phenylethyl)amino]ethyl-, tricyclo[3.3.1.1³,⁷]dec-2-yl ester, Carbamic acid, [1-[(2,3-dimethyl)-1H-pyrrol-4-ylmethyl]-2-[[1-(hydroxymethyl)-2-hydroxy-2-phenylethyl]amino]-1-methylethyl]-, tricyclo[3.3.1.1³,⁷]dec-2-yl ester (mixture of isomers), Carbamic acid, [1-(imidazo[1,5-a]pyridin-3-ylmethyl)-2-oxo-2-[(2-phenylethyl)amino]ethyl]-, tricyclo[3.3.1.1³,⁷]dec-2-yl ester, and Carbamic acid, [2-[[1-(hydroxymethyl)-2-hydroxy-2-phenylethyl]amino]-1-(imidazo[1,5-a]pyridin-3-ylmethyl)-1-methylethyl]-, tricyclo[3.3.1.1³,⁷]dec-2-yl ester (mixture of isomers).

7. A method for the treatment of idiopathic depression which comprises administering to a mammal in need of such treatment a therapeutically effective amount of a compound in unit dosage form of formula

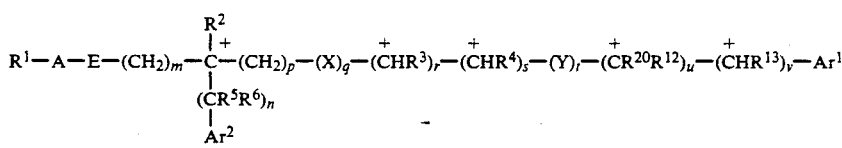

III or a pharmaceutically acceptable salt thereof wherein:

$R^1$ is a cyclo or polycycloalkyl hydrocarbon or mono- or polyheterocyclic moiety wherein the hetero atom(s) can be N, O, and/or S, of from 3 to 12 carbon atoms with from 0 to 4 substituents each independently selected from a straight or branched alkyl of from 1 to 6 carbon atoms, halogen, CN, OR*, SR*, $CO_2R^*$, $CF_3$, $NR^5R^6$, or $(CH_2)_nOR^5$ wherein R*, $R^5$, and $R^6$ are each independently hydrogen or a straight or branched alkyl of from 1 to about 6 carbon atoms;

m, n, p, q, r, s, t, u, and v are each independently an integer of from 0 to 6 with the proviso that q, r, and s are not all 1 when m, p, t, u, and v are all 0 except when X is not $CONR^9$ or A—E is not $(CH_2)_nCONH$—, —$SO_2NH$—, —$S(O)NH$—, —NHCONH, —$(CH_2)_n$—OCO—NH—, —SCONH—, —$O(CH_2)_nCO$— or —HC=CHCONH— wherein n is as above, A is
a bond,
O,
S,
NR*,
—$(CH_2)_nCO$—Z,
—$SO_2$—Z,
—SO—Z,
—S—Z,

—NHCO—Z,

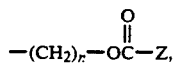

—SCO—Z,
—O—(CH$_2$)$_n$CO—Z,
—HC=CHCO—Z,
 wherein Z is a bond, oxygen, sulphur, or —NR*—
 wherein R* is as defined above;

E is
 a bond,
 an amino acid residue,
 —(CHR$^3$)$_r$—,
 —(CHR$^3$)$_r$—(CHR$^4$)$_s$—,
 —CONH—,
 —NHCO—,
 —OCO—,
 —COO—,
 —CH$_2$N(R$^3$)—,
 —CH$_2$O—,
 —CH$_2$S—,
 —C≡C—,

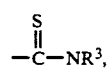

—SO$_2$NR$^3$—,
 —NR$^3$SO$_2$—,

—NHCONH—

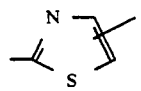

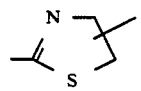

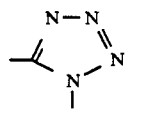

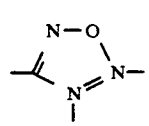

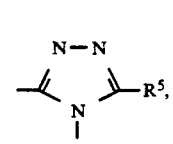

wherein r and s are independently as defined above and R$^3$ and R$^4$ are as defined above;
R$^2$ and R$^{20}$ are each independently hydrogen, a straight or branched alkyl of from 1 to 6 carbon atoms, —HC=CH$_2$, —C≡CH, —(CH$_2$)$_n$CH=CH$_2$, —(CH$_2$)$_n$C≡CH, —(CH$_2$)$_n$Ar$^1$, —(CH$_2$)$_n$Ar$^2$, —(CH$_2$)$_n$OR*, —(CH$_2$)$_n$OAr, —(CH$_2$)$_n$CO$_2$R*, —(CH$_2$)$_n$NR$^5$R$^6$ wherein n, R*, R$^5$, and R$^6$ are as defined above, and Ar$^1$ and Ar$^2$ are as defined below;

X and Y are each independently:
 —CONH—,
 —CONR$^9$,
 —NHCO—,
 —OCO—,
 —COO—,
 —CH$_2$N(R$^3$)—,
 —CH$_2$O—,
 —CH$_2$S—,
 —OCH$_2$—,
 —SCH$_2$—,
 —C≡C—,

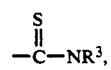

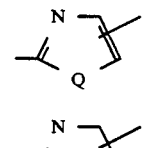

—SO$_2$NR$^3$—,
 —NR$^3$SO$_2$—,
 —NHCONH—,
 —CH(OR*)CH$_2$—,
 —COCH$_2$—,
 —CH$_2$CO—,
 —NR$^3$CH$_2$—,

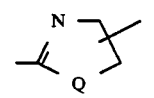

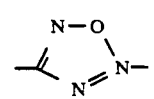

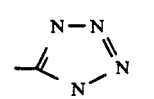

or

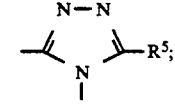

wherein Q is O, S, or NR$^9$;
R$^4$ are each independently the same as R$^2$ or —(CH$_2$)$_n$—B—D wherein n, is an integer of from 0 to
B is a bond,
 —OCO(CH$_2$)$_n$—,
 —O(CH$_2$)$_n$—,
 —NHCO(CH$_2$)$_n$—,
 —CONH(CH$_2$)$_n$—,
 —NHCOCH=CH—,
 —COO(CH$_2$)$_n$—, —CO(CH$_2$)$_n$—,
—SO(CH$_2$)$_n$—,
—S(CH$_2$)$_n$—,
—SO$_2$(CH$_2$)$_n$—,

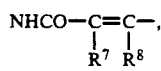

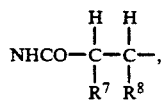

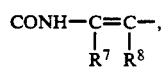

or

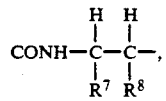

wherein R$_7$ and R$_8$ are each independently selected from hydrogen and R$_2$ or together form a ring (CH$_2$)$_m$ wherein m is an integer of from 1 to 5, D is
—COOR*,
—CH$_2$OR*,
—CHR$^2$OR*,
—CH$_2$SR*,
—CHR$^2$SR*,
—CONR$^5$R$^6$,
—CH,
—NR$^5$R$^6$,
—OH,
—H, and acid replacements such as tetrazole;

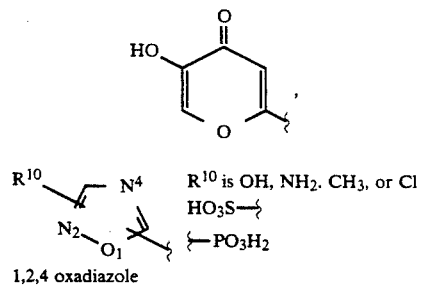

R$^{10}$ is OH, NH$_2$, CH$_3$, or Cl
HO$_3$S—
—PO$_3$H$_2$ 1,2,4 oxadiazole

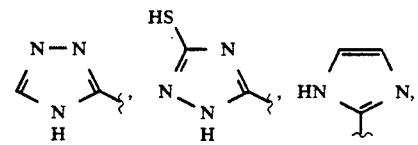

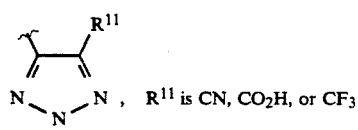  R$^{11}$ is CN, CO$_2$H, or CF$_3$

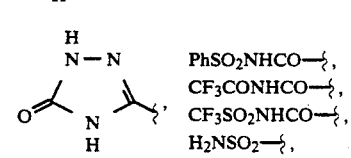
PhSO$_2$NHCO—,
CF$_3$CONHCO—,
CF$_3$SO$_2$NHCO—,
H$_2$NSO$_2$—,

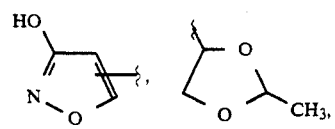

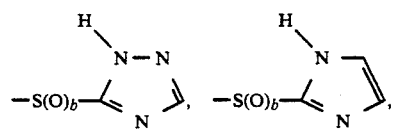

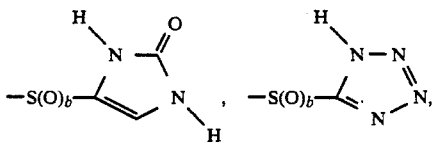

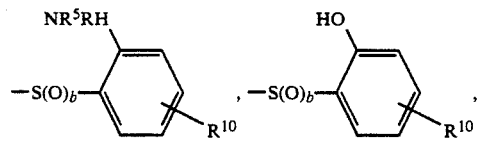

wherein b is an integer of from 0 to 2, wherein R*, R$^2$, R$^5$, and R$^6$ are as defined above; R$^9$ is H, or a straight or branched alkyl of from one to six carbon atoms, —(CH$_2$)$_n$CO$_2$R*, (CH$_2$)$_n$OAr', (CH$_2$)$_n$Ar', (CH$_2$)$_n$NR$^5$R$^6$, wherein n, R*, R$^5$, and R$^6$ are as defined above or taken from R$^3$ and Ar is taken from Ar$^1$ as defined below;

R$^{12}$ and R$^{13}$ are each independently hydrogen or taken together form a double bond, or are —(CH$_2$)$_n$—B—D as defined above; and Ar$^1$ and Ar$^2$ are each independently a mono-or polycyclic unsubstituted or substituted carbo-or heterocyclic aromatic or carbo- or heteroaromatic moiety.

8. A method for the treatment of idiopathic depression which comprises administering to a mammal in need of such treatment a therapeutically effective amount of a compound Carbamic acid, [2-[[1-(hydroxymethyl)-2-phenylethyl-]amino]-1-(1H-indol-3-ylmethyl)ethyl]-, tricyclo[3.3.1.1$^{3,7}$]dec-2-yl ester, [S-(R*,S*)]-, Carbamic acid, [2-[[1-(hydroxymethyl)-2-phenylethyl-]amino]-1-(1H-indol-3-ylmethyl)ethyl-, tricyclo[3.3.1.1$^{3,7}$]dec-2-yl ester, [S-(R*,R*)]-, Tricyclo[3.3.1.1$^{3,7}$]dec-2-yl[1-[[[1-hydroxymethyl)-2-phenylethyl]carbonyl]amino]-2-(1H-indol-3-yl)ethyl]carbamate, Carbamic acid, [2-[(2-hydroxy-2-phenylethyl)-amino]-1-(1H-indol-3-ylmethyl)-1-methylethyl]-, tricyclo[3.3.1.1$^{3,7}$]dec-2-yl ester (hydroxy center is RS, other center is R), Carbamic acid, [2-[[1-(hydroxymethyl)-2-phenyl-ethyl]amino]-1-(1H-indol-3-ylmethyl)-1-methylethyl]-, tricyclo[3.3.1.1$^{3,7}$]dec-2-yl ester, [R-(R*,S*)]-, 4-methylbenzenesulfonate (1:1) (salt), Benzenepropanol,β-[[2-(1H-indol-3-yl)-2-[[(tricyclo[3.3.1.1$^{3,7}$]dec-2-yloxy)carbonyl]amino]propyl-]amino]-, acetate (ester), [R-(R*,S*)]-, 4-methylbenzenesulfonate (1:1) (salt), Carbamic acid, [[2-[acetyl[1-(hydroxymethyl)-2-phenylethyl]amino]-1-(1H-indol-3-ylmethyl)-1-methyl]ethyl]-, tricyclo[3.3.1.1$^{3,7}$]dec-2-yl ester, [R-(R*,S*)]-, 5,13-Dioxa-2,8-diazatetradec-10-enoic acid, 3-(1H-indol-3-ylmethyl)-3-methyl-4,9,12-trioxo-7-phenyl-, tricyclo[3.3.1.1³,⁷]dec-2-yl ester, [S-(R*,S*)]-, 5,13-Dioxa-2,8-diazatetradecanoic acid, 3-(1H-indol-3-ylmethyl)-3-methyl-4,9,12-trioxo-7-phenyl-, tricyclo[3.3.1.1³,⁷]dec-2-yl ester, [R-(R*,R*)]-, Carbamic acid, [1-(1H-indol-3-ylmethyl)-1-methyl-2-[(1-oxo-4-phenylbutyl)amino]ethyl]-, tricyclo[3.3.1.1³,⁷]dec-2-yl ester (R)-, Carbamic acid, [2-(benzoylamino)-1-(1H-indol-3-ylmethyl)-1-methylethyl]-, tricyclo[3.3.1.1³,⁷]-dec-2-yl ester, (R)-, Carbamic acid, [1-(1H-indol-3-ylmethyl)-1-methyl-2-[(1-oxo-3-phenylpropyl)amino]ethyl]-, tricyclo[3.3.1.1³,⁷]dec-2-yl ester, (R)-, Carbamic acid, [1-(1H-indol-3-ylmethyl)-1-methyl-2-[(2-phenylacetyl)amino]ethyl]-, tricyclo[3.3.1.1³,⁷]dec-2-yl ester, (R)-, Carbamic acid, [2-[[3-[[1-(hydroxymethyl)-2-phenylethyl]amino]-3-oxopropyl]amino]-1-(1H-indol-3-ylmethyl)-1-methyl-2-oxoethyl]-, [R,(R*,S*)]-, Carbamic acid, [1-(1H-indol-3-ylmethyl)-2-[[1-(hydroxymethyl)-2-phenylethyl]amino]-3-oxopropyl]amino]-1-methyl-2-oxoethyl]-, tricyclo[3.3.1.1³,⁷]dec-2-yl ester, [S-(R*,R*)]-, D-Phenyl alaninamide, α-methyl-N-[(tricyclo[3.3.1.1³,⁷]dec-2-yloxy)carbonyl]-D-tryptophyl-β-alanyl-, L-Phenylalaninamide, α-methyl-N-[(tricyclo[3.3.1.1³,⁷]dec-2-yloxy)carbonyl]-D-tryptophyl-β-alanyl-, L-Phenylalaninamide, α-methyl-N-[(tricyclo[3.3.1.1³,⁷]dec-2-yloxy)carbonyl]-L-tryptophyl-β-alanyl-, D-Phenylalaninamide, α-methyl-N-[tricyclo[3.3.1.1³,⁷]dec-2-yloxy)carbonyl]-L-tryptophyl-β-alanyl-, 12-Oxa-2,5,9-triazatridecanoic acid, 3-(1H-indol-3-ylmethyl)-3-methyl-4,8,11-trioxo-10-(phenylmethyl)-, tricyclo[3.3.1.1³,⁷]dec-2-yl ester, [R,(R*,R*)]-, L-Phenylalanine, N-[N-[α-methyl-N-[(tricyclo[3.3.1.1³,⁷]dec-2-yloxy)carbonyl]-D-tryptophyl]-β-alanyl]-, phenylmethyl ester, Propanoic acid, 2-[[3-[[3-(1H-indol-3-yl)-2-methyl-1-oxo-2-[[(tricyclo[3.3.1.1³,⁷]dec-2-yloxy)carbonyl]amino]propyl]amino]-1-oxopropyl]amino]-3-phenyl-, phenylmethyl ester, S-(R*,R*)]-, D-Phenylalanine, N-[N-[α-methyl-N-[(tricyclo[3.3.1.1³,⁷]dec-2-yloxy)carbonyl]-D-tryptophyl]-β-alanyl]-, L-Phenylalanine, N-[N-[α-methyl-N-[(tricyclo[3.3.1.1³,⁷]dec-2-yloxy)carbonyl]-D-tryptophyl]-β-alanyl]-, L-Phenylalanine, N-[N-[α-methyl-N-[(tricyclo[3.3.1.1³,⁷]dec-2-yloxy)carbonyl]-L-tryptophyl]-β-alanyl]-, Benzenepropanoic acid, α-[[3-[[3-[(1H-indol-3-yl)-2-methyl-1-oxo-2-[[(tricyclo[3.3.1.1³,⁷]dec-2-yloxy)carbonyl]amino]propyl]amino]-1-oxopropyl]-amino]-, [S-(R*,S*)]-, Glycine, N-[2-methyl-N-[(tricyclo[3.3.1.1³,⁷]dec-2-yloxy)carbonyl]-D-tryptophyl]-, phenylmethyl ester, Carbamic acid, [3-(1H-indol-3-ylmethyl)-2,5-dioxo-1-(2-phenylethyl)-3-pyrrolidinyl]-, tricyclo[3.3.1.1³,⁷]-dec-2-yl ester, (±)-, Carbamic acid, [1-(1H-imidazol-4-ylmethyl)-1-methyl-2-oxo-2-[(2-phenylethyl)amino]ethyl]-, 1,1-dimethylethyl ester, (±)-, Carbamic acid, [3-(1H-indol-3-yl)-1-methyl-1-[[(2-phenylethyl)amino]carbonyl]propyl]-, tricyclo[3.3.1.1³,⁷]dec-2-yl ester, (±)-, Carbamic acid, [1-[[[1-hydroxymethyl)-2-phenylethyl]amino]carbonyl]-3-(1H-indol-3-yl)-1methylpropyl]-, tricyclo[3.3.1.1³,⁷]dec-2-yl ester (hydroxymethyl center is S, other center is RS), 13-Oxa-2,5,α-triazatetradec-10-enoic acid, 3-[2-(1H-indol-3-yl)ethyl]-3-methyl-4,5,12-trioxo-7-phenyl-, tricyclo[3.3.1.1³,⁷]dec-2-yl ester [TRP center is R/S mixture, other center is R], L-Phenylalaninamide, N-[[(1,1-dimethylethoxy)-carbonyl]-α-methyl]-L-tryptophyl]-L-methionyl-L-α-aspartyl-, Glycine, N-[2-methyl-N-[(tricyclo[3.3.1.1³,⁷]dec-2-yloxy)carbonyl]-D-tryptophyl]-L-phenylalanyl-, Carbamic acid, [1-[[[1-(hydroxymethyl)-2-phenylethyl]amino]carbonyl]-2-(1H-indol-3-yl)propyl]-, tricyclo[3.3.1.1³,⁷]dec-2-yl ester (hydroxymethyl center S, other centers RS), 2,4-Heptadienoic acid, 6-[[3-(1H-indol-3-yl)-2-methyl-1-oxo-2-[[(tricyclo[3.3.1.1³,⁷]dec-2-yloxy)carbonyl]amino]propyl]amino]-7-phenyl-, [R,R*,S*-(E,E)]]-, Glycine, N-[2-methyl-N-[(tricyclo-[3.3.1.1³,⁷]dec-2-yloxy)carbonyl]-D-tryptophyl]-, phenylmethyl ester, and Tricyclo[3.3.1.1³,⁷]dec-2-yl-R-(R*,S*)]-[1-[4,5-dihydro-4-(phenylmethyl)-2-thiazolyl]-2-(1H-indol-3-yl)-1-methylethyl]carbamate.

9. A method for the treatment of idiopathic depression which comprises administering to a mammal in need of such treatment a therapeutically effective amount of a compound in unit dosage form of formula

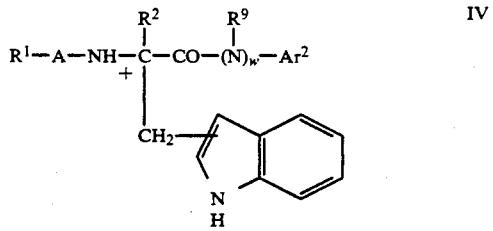

or a pharmaceutically acceptable salt thereof wherein:
$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or $-(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is $-(CH_2)_nCO-$, $-SO_2-$, $-SO-$, $-NHCO-$,

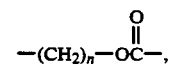

$-SCO-$, $-O-(CH_2)_nCO-$ or $-HC=CHCO-$ wherein n is an integer from zero to six;

$R^2$ is a straight or branched alkyl of from one to six carbon atoms, $-HC=CH_2$, $-C\equiv CH$, $-(CH_2)_n-CH=CH_2$, $-(CH_2)_nC\equiv CH$, $-(CH_2)_nAr$, $-(CH_2)_nOR^*$, $-(CH_2)_nOAr$, $-(CH_2)_nCO_2R^*$, $-(CH_2)_nNR^5R^6$ wherein n, R, $R^5$, and $R^6$ are as defined above and Ar is a mono or polycyclic unsubstituted or substituted carbo- or heterocyclic aromatic or hydroaromatic moiety;

$R^9$ is H, or a straight or branched alkyl of from one to six carbon atoms, $-(CH_2)_nCO_2R^*$, $(CH_2)_nOAr'$, $(CH_2)_nAR'$, $(CH_2)_nNR^5R^6$, wherein n, $R^*$, $R^5$, and $R^6$ are as defined above or taken from $R^3$ and $Ar'$ is taken independently from Ar and w is zero or 1;

$Ar^2$ is

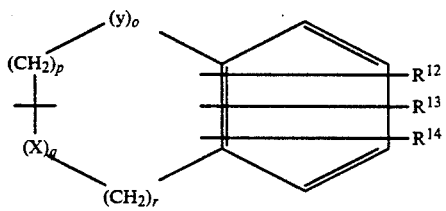

wherein x and y are each independently O, S, N, $CH_2$, $-CHR^{12}$, $-NR^{12}-$, $-NR^{12}CO-$, $-C=N-$, $-C=C-$, or $-(C=O)-$ or a bond; o, p, q, and r are each independently an integer of from 0 to 3, provided that when o, p, q, and r are all simultaneously zero, $Ar^2$ becomes

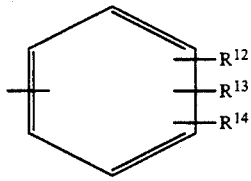

$R^{12}$, $R^{13}$, and $R^{14}$ are each independently halogen, $R^2$ as is defined above, $-(CH_2)_g-B-D$ wherein g is an integer of from 0 to 6 wherein B
is a bond,
$-OCO(CH_2)_n-$,
$-O(CH_2)_n-$,
$-NHCO(CH_2)_n-$,
$-CONH(CH_2)_n-$,
$-NHCOCH=CH-$,
$-COO(CH_2)_n-$,
$-CO(CH_2)_n-$,
$-S(CH_2)_n-$,
$-SO(CH_2)_n-$,
$-SO_2(CH_2)_n-$,

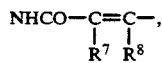

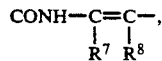

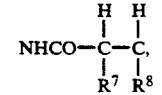

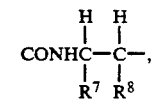

$-NHSO_2-(CH_2)_n-$, or $-SO_2NH-(CH_2)_n-$, wherein $R^7$ and $R^8$ are independently selected from hydrogen and $R^2$, or together form a ring $(CH_2)_m$ wherein m is an integer of from 1 to 5 and n is as defined above;

D is
$-COOR^*$,
$-CH_2OR^*$,
$-CHR^2OR^*$,
$-CH_2SR^*$,
$-CHR^2SR^*$,
$-CONR^5R^6$,
$-CN$,
$-NR^5R^6$,
$-H$, and acid replacements such as tetrazole,

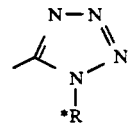

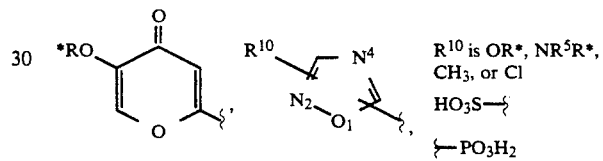

1,2,4 oxadiazole

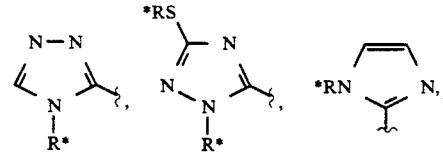

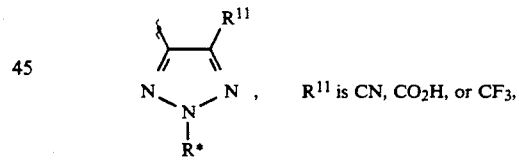

$R^{11}$ is CN, $CO_2H$, or $CF_3$,

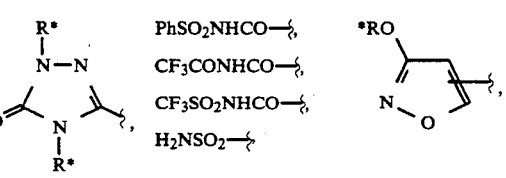

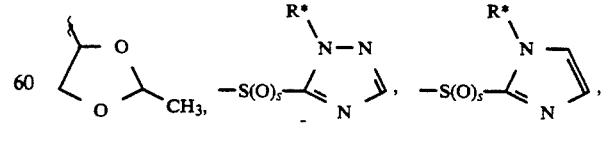

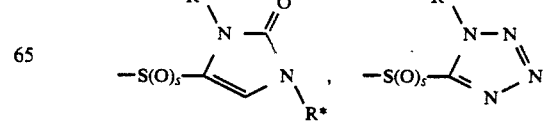

5,217,957

71

-continued

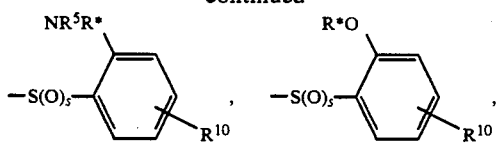

wherein s is an integer of from 0 to 2 wherein R*, $R^2$, $R^5$, and $R^6$ are as defined above.

10. A method for the treatment of idiopathic depression which comprises administering to a mammal in need of such treatment a therapeutically effective amount of a compound in unit dosage form selected from:
carbamic acid, [2-[(2,3-dihydro-2-hydroxy-1H-inden-1-yl)amino]-1-(1H-indol-3-ylmethyl)-1-methyl-2-oxoethyl]-, 1,7,7-trimethylbicyclo[2.2.1]hept-2-yl ester (bicyclo ring is 1S-endo (+-isomer), trp center is D, indene ring centers are unknown),
carbamic acid, [2—[(2,3-dihydro-1-hydroxy -1H-inden-2-yl)amino]-1-1H-indol-3-ylmethyl)-2-methyl-2-oxoethyl]-, 1,7,7-trimethylbicyclo[2.2.1]hept-2-yl ester, [1S*[1α,2β[S(trans)],4β]]- (Bicyclo system is 1S-endo),
carbamic acid, [2-[(2,3-dihydro-1-hydroxy -1H-inden-2-yl)amino]-1-(1H-indol-3-ylmethyl)-1-methyl-2-oxoethyl]-, 1,7,7-trimethylbicyclo[2.2.1]hept-2-yl ester, [1S[1α, 2β[S*(1S*,2S*)],4α]]- [Bicyclo system is 1S-endo, all other centers are R],
carbamic acid, [1-(1H-indol-3-ylmethyl)-1-methyl-2-oxo-2-[(1,2,3,4-tetrahydro-1-oxo-2-naphthalenyl)amino]ethyl]-, 1,7,7-trimethylbicyclo[2.2.1]hept-2-yl ester (Bicyclo system 1S-endo; TRP center R; naphthyl center (−) or (+)), (Isomer II),
carbamic acid, [1-(1H-indol-3-ylmethyl)-1-methyl-2-oxo-2-[(1-2,3,4-tetrahydro-1-oxo-2-naphthalenyl)amino]ethyl]-, 1,7,7-trimethylbicyclo[2.2.1.1]hept-2-yl ester (Bicyclo system 1S-endo; TRP center R; naphthyl center (+) or (−)), (Isomer I),
carbamic acid, [1-(1H-indol-3-ylmethyl)-1-methyl-2-oxo-2-[(1,2,3,4-tetrahydro-1-naphthalenyl)amino]ethyl]-, tricyclo[3.3.1.1^{3,7}]dec-2-yl ester, (±)-,
carbamic acid, [1-1H-indol-3-ylmethyl)-1-methyl-2-oxo-2-[(1,2,3,4-tetrahydro-2-naphthalenyl)amino]ethyl]-, tricyclo[3.3.1.1^{3,7}]dec-2-yl ester, (±)-,
carbamic acid, [1-(1H-indol-3-ylmethyl)-1-methyl-2-oxo-2-(1,2,3,4-tetrahydro-2-isoquinolinyl)ethyl]-, tricyclo[3.3.1.1^{3,7}]-dec-2-yl ester, (R)-,
4-[[1,2,3,4-tetrahydro-2-[[3-(1H-indol-3-yl)-2-methyl-1-oxo-2-[[(tricyclo[3.3.1.1^{3,7}]dec-2-yloxy)carbonyl]amino]propyl]amino]-1-naphthalenyl]amino]-4-oxobutanoate
tricyclo[3.3.1.1^{3,7}]dec-2-yl-[2-[(1-azido-1,2,3,4-tetrahydro-2-naphthalenyl)amino]-1(1H-indol-3-ylmethyl)-1-methyl-2-oxoethyl]carbamate,
methyl 3-[[2-[[3-(1H-indol-3-yl)-2-methyl-1-oxo-2-[[(tricyclo[3.3.1.1^{3,7}]dec-2-yloxy)carbonyl]amino]propyl]amino]-1,2,3,4-tetrahydro-1-naphthalenyl]amino]-3-oxopropanoate,
methyl 3-[[2-[[3-(1H-indol-3-yl)-2-methyl-1-oxo-2-[[(tricyclo[3.3.1.1^{3,7}]dec-2-yloxy)carbonyl]amino]propyl]amino]-1,2,3,4-tetrahydro-1-naphthalenyl]amino]-3-oxopropanoate, and
methyl 1-[[1,2,3,4-tetrahydro-2-[[3-(1H-indol-3-yl)-2-methyl-1-oxo-2-[[(tricyclo-[3.3 1.1^{3,7}]dec-2-yloxy)carbonyl]amino]propyl]amino]-1-naphthalenyl]amino]-4-oxo-2-butanoate.

72

11. A method for the treatment of idiopathic depression which comprises administering to a mammal in need of such treatment a therapeutically effective amount of a compound in unit dosage form of formula

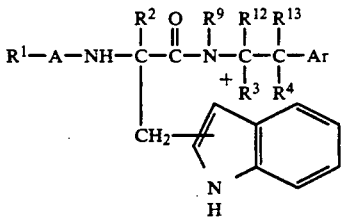

or a pharmaceutically acceptable salt thereof wherein:
$R^1$ is a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and —$(CH_2)_nOR^5$ wherein R* is hydrogen, straight or branched alkyl of from one to six carbon atoms, —$(CH_2)_nAr$, —COAr, —$(CH_2)_nOCOAr$, or —$(CH_2)_nNR^5COAr$ and R* may also independently be R** as defined below,
and R must be present at least once in formula I, and R is attached to formula I through a metabolically labile bond and can include

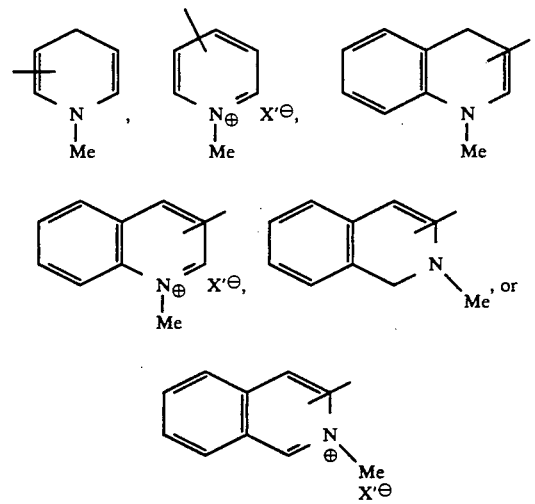

$R^5$ and $R^6$ are each independently hydrogen or alkyl of from one to about six carbon atoms and n is an integer from zero to six;
and R** is —$(CH_2)_nNR^5R^6$, —$(CH_2)_n$—B—D* wherein D* is O—COR*, $CO_2Ar^2$, $(CH_2)_nAr^2$, $OCOAr^2$, $NR^5COAr^2$, $COAr^2$, $CO_2CH(-R)$—$CO_2R^*$, $CO_2$—$(CH_2)_nOCOR^*$ where $Ar^2$ is independently taken from Ar, where m is as defined below, $CONHCH(R)CO_2R^*$ where R is a side chain of a biologically significant amino acid, R is hydrogen only when B is not a bond, —$CO_2CH_2CH_2N^+(R^*)_3X^{1-}$ when $X^{1-}$ is a pharmaceutically acceptable counter anion,
A is —$(CH_2)_nCO$—, —$SO_2$—, —$S(=O)$—, —NHCO—, —$(CH)_n$—$C(=O)$—, $$-\overset{\overset{O}{\|}}{S}C-,$$

—O—(CH$_2$)$_n$CO— or —HC=CHCO— wherein n is an in from zero to six;

R$^2$ is a straight or branched alkyl of from one to about six carbon atoms, —HC=CH$_2$, —C≡CH, —(CH$_2$)$_n$—CH=CH$_2$, —(CH$_2$)$_n$C≡CH, —(CH$_2$)$_n$Ar, —(CH$_2$)$_n$OR*, —(CH$_2$)$_n$OAr, —(CH$_2$)$_n$CO$_2$R*, or —(CH$_2$)$_n$NR$^5$R$^6$ wherein n, R*, R$^5$ and R$^6$ are as defined above and Ar is as defined below;

R$^3$ and R$^4$ are each independently selected from hydrogen, R$^2$ and —(CH$_2$)$_{n'}$—B—D wherein:

n' is an integer of from zero to three;

B is
a bond,
—OCO(CH$_2$)$_n$—,
—O(CH$_2$)$_n$—,
—NHCO(CH$_2$)$_n$—,
—CONH(CH$_2$)$_n$—,
—NHCOCH=CH—,
—COO(CH$_2$)$_n$—,
—CO(CH$_2$)$_n$—,
—S—(CH$_2$)$_n$—,
—S(=O)—(CH$_2$)$_n$—,
—SO$_2$—(CH$_2$)$_n$—,
—NHSO$_2$—(CH$_2$)$_n$—,
—SO$_2$NH—(CH$_2$)$_n$—, $$\text{NHCO}-\underset{R^7}{C}=\underset{R^8}{C}-, \quad \text{CONH}-\underset{R^7}{C}=\underset{R^8}{C}-,$$

$$\text{NHCO}-\underset{R^7}{\overset{H}{C}}-\underset{R^8}{\overset{H}{C}}-, \text{ or } \text{CONH}-\underset{R^7}{\overset{H}{C}}-\underset{R^8}{\overset{H}{C}}-$$

wherein R$^7$ and R$^8$ are each independently selected from hydrogen and R$^2$ or together form a ring (CH$_2$)$_m$ wherein m is an integer of from 1 to 5 and n is as defined above;

D is
hydrogen,
—COOR*,
—CH$_2$NR$^5$R*,
—CHR$^2$NR$^5$R*,
—CH$_2$OR*,
—CHR$^2$OR*,
—CH$_2$SR*,
—CHR$^2$SR*,
—CONR$^5$R$^6$,
—CONR$^5$R*, an acid replacement selected from 1,2,4 oxadiazole R$^{10}$ is OR*, NR$^5$R*, CH$_3$, or Cl
HO$_3$S—⁀
⁀—PO$_3$H$_2$—;

R$^{11}$ is CN, CO$_2$H, or CF$_3$,

PhSO$_2$NHCO—⁀,
CF$_3$CONHCO—⁀,
CF$_3$SO$_2$NHCO—⁀,
H$_2$NSO$_2$—⁀, wherein m is an integer of from 0 to 2 wherein R*, R$_2$, R$^5$, and R$^6$ are as defined above;

R$^9$ is hydrogen or a straight or branched alkyl of from one to about six carbon atoms, —(CH$_2$)$_n$CO$_2$R*, —(CH$_2$)$_n$NR$^5$R*, wherein n, R*, and R$^5$ are as defined above or taken from R$^3$;

R$^{12}$ and R$^{13}$ are each independently hydrogen or are each independently taken with R$^3$ and R$^4$, respectively, to form a moiety doubly bonded to the carbon atom; and Ar is a mono- or polycyclic unsubstituted or substituted carbo- or heteroaromatic or carbo- or heterohydroaromatic moiety.

12. A method for the treatment of idiopathic depression which comprises administering to a mammal in need of such treatment a therapeutically effective amount of a compound selected from L-Aspartic acid, N-[N-[α-methyl-N-[(tricyclo[3.3.1.1$^{3,7}$]-dec-2-yloxy)carbonyl]-D-tryptophyl]-L-phenylalanyl]-, L-Glutamic acid, N-[N-[α-methyl-N-[(tricyclo[3.3.1.1$^{3,7}$]-dec-2-yloxy)carbonyl]-D-tryptophyl]-L-phenylalanyl]-, L-Glutamic acid, N-[N-[α-methyl-N-[(tricyclo[3.3.1.1³,⁷]-dec-2-yloxy)carbonyl]-D-tryptophyl]-L-phenylalanyl]-, dimethyl ester, 2-[[3-(1H-Indol-3-yl)-2-methyl-1-oxo-2[[tricyclo-[3.3.1.1³,⁷]dec-2-yloxy)carbonyl]amino]propyl]-amino]-3-phenylpropyl[R-(R*,S*)]-1,4-dihydro-1-methyl-3-pyridinecarboxylate, 2-[[3-(1H-indol-3-yl)-2-methyl-1-oxo-2[[(tricyclo-[3.3.1.1³,⁷]dec-2-yloxy)carbonyl]amino]propyl]-amino]-3-phenylpropyl[R-(R*,S*)]-trigonelline iodide 2-[3-[3-(1H-indol-3-yl)-2-methyl-1-oxo-2-[[tricyclo-[3.3.1.1³,⁷]dec-2-yloxy)carbonyl]amino]propyl]amino]-3-phenylpropyl[R-(R*,S*)]-3-pyridinecarboxylate, butanoic acid, 4-[[2-[[3-(1H-indol-3-yl)-2-methyl-1-oxo-2-[[(tricyclo[3.3.1.1³,⁷]dec-2-yloxy)carbonyl]amino]-propyl]amino]-1phenylethyl]amino]-4-oxo-, (2,2-dimethyl-1-oxopropoxy)methyl ester, [R-(R*,R*)]-, butanoic acid, 4-[[2-[[3-(1H-indol-3-yl)-2-yloxy)carbonyl]amino]propyl]amino]ethyl]amino]-4-oxo-, chloromethyl ester, [R-(R*,R*)]-, Pentanedioic acid, [4-[[2-[[3-(1H-indol-3-yl)-2-methyl-1-oxo-2-[[(tricyclo[3.3.1.1³,⁷]dec-2-yloxy)carbonyl]amino]propyl]amino]-1-phenylethyl]amino]-1,4-dioxobutoxy]methyl ester, [R-(R*,R*)]-, butanoic acid, 4-[[2-[[3-(1H-indol-3-yl)-2-methyl-1-oxo-2-[[(tricyclo[3.3.1.1³,⁷]dec-2-yloxy)carbonyl]amino]-propyl]amino]-1-phenylethyl]amino]-4-oxo-2,3-dihydro-1H-inden-5-yl ester, [R-(R*,R*)]-, and butanoic acid, 4-[[2-[[3-(1H-indol-3-yl)-2-methyl-1-oxo-2-[[(tricyclo[3.3.1.1³,⁷]dec-2-yloxy)carbonyl]amino]-propyl]amino]-1-phenylethyl]amino]-4-oxo-, [R-(R*,R*)]-.

13. A method for the treatment of depression which comprises administering to a mammal in need of such treatment a therapeutically effective amount of a compound in unit dosage form of formula

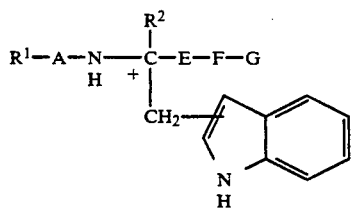

or a pharmaceutically acceptable salt thereof wherein:

$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, OR*, SR*, $CO_2R^*$, $CF_3$, $NR^5R^6$, or $-(CH_2)_nOR^5$, wherein R* is hydrogen, straight or branched alkyl of from one to six carbon atoms, $R^5$ and $R^6$ are each independently hydrogen or alkyl of from one to six carbon atoms; and n is an integer from zero to six;

A is $-(CH_2)_nCO-$, $-SO_2-$, $-SO-$, $-NHCO-$,

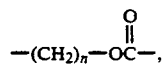

$-SCO-$, $-O-(CH_2)_nCO-$ or $-HC=CHCO-$ wherein n is an integer from zero to six;

$R^2$ is a straight or branched alkyl of from one to six carbon atoms, $-HC=CH_2$, $-C\equiv CH$, $-CH_2-CH=CH_2$, $-(CH_2)_nC\equiv CH$, $-(CH_2)_nAr$, $-(CH_2)_nOR^*$, $-(CH_2)_nOAr$, $-(CH_2)_nCO_2R^*$, $-(CH_2)_nNR^5R^6$ wherein n, R' $R^5$ and $R^6$ are as defined above and Ar is a mono-or polycyclic unsubstituted or substituted carbo-or heterocyclic aromatic or hydroaromatic moiety;

E is $-CONH-$, $-NHCO-$, $-OCO-$, $-COO-$, $-(CH_2)_mNR^3-$, $-(CH_2)_mO-$, $-(CH_2)_mS-$, $-C\equiv C-$,

$-SO_2NR^3-$, $-NR^3SO_2-$, $-NHCONH-$, $-CH_2CO-$, $-COCH_2-$, $-(CH_2)_mNHCO-$, $-(CH_2)_mCONH-$ wherein m is an integer of from 1-5,

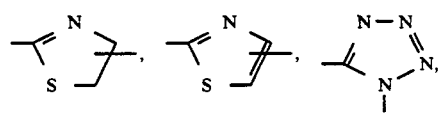

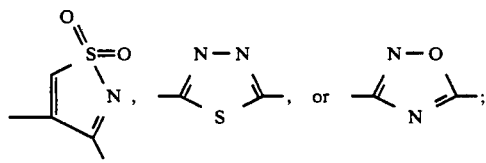

F is a bond, $-CH(R)CO-$ wherein R is $-(CHR^3)_p-(CHR^4)_q-D$, wherein D is as defined below, wherein p and q are each independently 0, 1, or 2 and wherein F is a desamino biologically significant amino acid, excluding Tyr, Phe, Trp, His;

$R^3$ and $R^4$ are each independently selected from $R^2$ and $-(CH_2)_{n'}-B-D$ wherein:

n' is an integer of from zero to three;

B is a bond,
$-OCO(CH_2)_n-$,
$-O(CH_2)_n-$,
$-NHCO(CH_2)_n-$,
$-CONH(CH_2)_n-$,
$-NHCOCH=CH-$,
$-COO(CH_2)_n-$,
$-CO(CH_2)_n-$,
$-S-(CH_2)_n-$,
$-S(=O)-(CH_2)_n-$,
$-SO_2-(CH_2)_n-$,
$-NHSO_2-(CH_2)_n-$,
$-SO_2NH-(CH_2)_n-$,

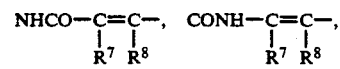

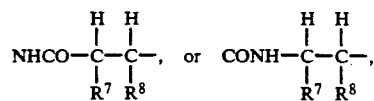

wherein $R^7$ and $R^8$ are independently selected from hydrogen and $R^2$ or together form a ring $(CH_2)_m$ wherein m is an integer of from 1 to 5 and n is as defined above;
D is
—COOR*,
—CH$_2$OR*,
—CHR$_2$OR*,
—CH$_2$SR*,
—CHR$^2$SR*,
—CONR$^5$R$^6$,
—CN,
—NR$^5$R$^6$,
—OH,
—H or an acid replacement such as tetrazole, or

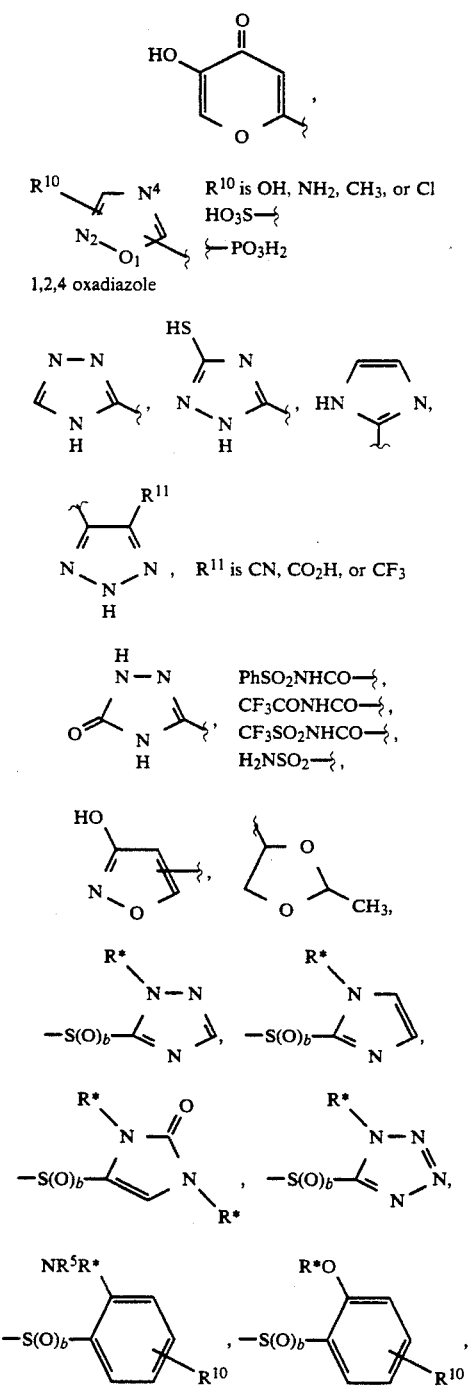

1,2,4 oxadiazole

R$^{11}$ is CN, CO$_2$H, or CF$_3$

PhSO$_2$NHCO—,
CF$_3$CONHCO—,
CF$_3$SO$_2$NHCO—,
H$_2$NSO$_2$—, wherein s is an integer of from 0 to 2,
wherein R*, R$^2$, R$^5$, and R$^6$ are as defined above and
G is R$^3$ as defined above, and
G cannot be hydrogen when F is a bond.

14. A method for the treatment of idiopathic depression which comprises administering to a mammal in need of such treatment a therapeutically effective amount of a compound selected from (R)—N—[3-(1H-indol-3-yl)-2-methyl-1-oxo-2-[[(tricyclo[3.3.1.1$^{3,7}$]dec-2-yloxy)carbonyl]amino]propyl]glycine, (R)-4-[[3-(1H-indol-3-yl)-2-methyl-1-oxo-2-[[(tricyclo[3.3.1.1$^{3,7}$]dec-2-yloxy)carbonyl]amino]propyl]amino]butanoic acid, Methyl (R)-4-[[3-(1H-indol-3-yl)-2-methyl-1-oxo-2-[[(tricyclo[3.3.1.1$^{3,7}$]dec-2-yloxy)carbonyl]amino]propyl]amino]butanoate, Phenylmethyl (R)-3-[[3-(1H-indol-3-yl)-2-methyl-1-oxo-2-[[(tricyclo[3.3.1.1$^{3,7}$]dec-2-yloxy)carbonyl]amino]propyl]amino]propanoate, Methyl N-[α-methyl-N-[(tricyclo[3.3.1.1$^{3,7}$]dec-2-yloxy)carbonyl]-D-tryptophyl]-β-alanine, Phenylmethyl N-[2-methyl-N-[(tricyclo[3.3.1.1$^{3,7}$]dec-2-yloxy)carbonyl]-D-tryptophyl]glycine, N-[α-methyl-N-[(tricyclo[3.3.1.1$^{3,7}$]dec-2-yloxy)carbonyl]-D-tryptophyl]-β-alanine, Tricyclo[3.3.1.1$^{3,7}$]dec-2-yl [1S-[1R*(S*),2R*]]-[2-[[1-(hydroxymethyl)-2-methyl-butyl]amino]-1-(1H-indol-3-ylmethyl)-1-methyl-2-oxoethyl]carbamate, Tricyclo[3.3.1.1$^{3,7}$]dec-2-yl [R-(R*,S*)]-[2-[[1-(hydroxymethyl)-3-methylbutyl]amino]-1-(1H-indol-3-ylmethyl)-1-methyl-2-oxoethyl]carbamate, Methyl N-[α-methyl-N-[(tricyclo[3.3.1.1$^{3,7}$]dec-2-yloxy)carbonyl]-D-tryptophyl]-L-methionine, N-[α-methyl-N-[(tricyclo[3.3.1.1$^{3,7}$]dec-2-yloxy)carbonyl]-D-tryptophyl]-L-methionine, Methyl N-[N-[α-methyl-N-[(tricyclo[3.3.1.1$^{3,7}$]dec-2-yloxy)carbonyl]-D-tryptophyl]L-methionyl]-β-alanine, N-[S-methyl-N-[α-methyl-N-[(tricyclo[3.3.1.1$^{3,7}$]dec-2-yloxy)carbonyl]-D-tryptophyl]-D-cysteinyl-β-alanine, S-methyl-N-[α-methyl-N-[(tricyclo[3.3.1.1$^{3,7}$]dec-2-yloxy)carbonyl]-D-tryptophyl-D-cysteine, N-[α-Methyl-[N-[(tricyclo[3.3.1.1$^{3,7}$]dec-2-yloxy)carbonyl]-D-tryptophyl]-γ-(methylsulfinyl)-L-α-aminobutanoic acid, and N-[α-methyl-N-[(tricyclo[3.3.1.1$^{3,7}$]dec-2-yloxy)carbonyl]-D-tryptophyl]-γ-(methylsulfonyl)-L-α-aminobutanoic acid.

15. A method for the treatment of depression which comprises administering to a mammal in need of such treatment a therapeutically effective amount of a compound in unit dosage form of formula

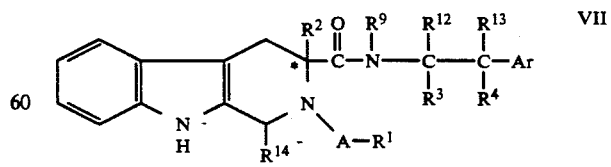

VII or a pharmaceutically acceptable salt thereof wherein:
R$^1$ is tert.-butyl, a cycloalkyl or polycycloalkyl hydrocarbon of from three to twelve carbon atoms with from zero to four substituents each independently selected from the group consisting of a straight or branched alkyl of from one to about six carbon atoms, halogen, CN, OR*, SR*, $CO_2R^*$, $CF_3$, $NR^5R^6$, and —$(CH_2)_nOR^5$ wherein R* is hydrogen or a straight or branched alkyl of from one to six carbon atoms, $R^5$ and $R^6$ are each independently hydrogen or alkyl of from one to about six carbon atoms and n is an integer from zero to six;

A is —$(CH_2)_nCO$—, —$SO_2$—, —$S(=O)$—, —NHCO—,

—$(CH_2)_n$—OC(=O)—, —SCO—, —O—$(CH_2)_nCO$—,

—HC=CHCO—, or —C(=O)—O—$(CH_2)_n$— wherein n is an integer from zero to six;
$R^2$ is hydrogen, a straight or branched alkyl of from one to about six carbon atoms, —HC=$CH_2$, —C≡CH, —$CH_2$—CH=$CH_2$, —$CH_2$C≡CH, —$(CH_2)_nAr$, —$(CH_2)_nOR^*$, —$(CH_2)_nOAr$, —$(CH_2)_nCO_2R^*$, or —$(CH_2)_nNR^5R^6$ wherein n, R*, $R^5$ and $R^6$ are as defined above and Ar is as defined below;
$R^3$, $R^4$ and $R^{14}$ are each independently selected from hydrogen, $R^2$ and —$(CH_2)_{n'}$—B—D wherein:
n' is an integer of from zero to three;
B is
  a bond,
  —$OCO(CH_2)_n$—,
  —$O(CH_2)_n$—,
  —$NHCO(CH_2)_n$—,
  —$CONH(CH_2)_n$—,
  —NHCOCH=CH—,
  —$COO(CH_2)_n$—,
  —$CO(CH_2)_n$—,
  —$S(CH_2)_n$—,
  —$SO(CH_2)_n$—,
  —$SO_2(CH_2)_n$—,
  —$NHSO_2(CH_2)_n$—,
  —$SO_2NH(CH_2)_n$—,

NHCO—C($R^7$)=C($R^8$)—, CONH—C($R^7$)=C($R^8$)—,

NHCO—CH($R^7$)—CH($R^8$)—, CONH—CH($R^7$)—CH($R^8$)—, wherein $R^7$ and $R^8$ are independently selected from hydrogen and $R^2$ or together form a ring $(CH_2)_m$ wherein m is an integer of from 1 to 5 and n is as defined above;
D is
  —COOR*,
  —$CH_2OR^*$,
  —$CHR^2OR^*$,
  —$CH_2SR^*$,
  —$CHR^2SR^*$,
  —$CONR^5R^6$,
  —CN,
  —$NR^5R^6$,
  —OH,
  —H, and acid replacements such as tetrazole,

[structure: HO-substituted pyranone]

$R^{10}$—\[1,2,4-oxadiazole\]—   $R^{10}$ is OH, $NH_2$, $CH_3$, or Cl
                                 $HO_3S$—
                                 —$PO_3H_2$

[structures: tetrazole-NH, thiol-triazine, imidazole]

[structure: triazole with $R^{11}$]   $R^{11}$ is CN, $CO_2H$, or $CF_3$

[structure: triazolone]   $PhSO_2NHCO$—,
                          $CF_3CONHCO$—,
                          $CF_3SO_2NHCO$—,
                          $H_2NSO_2$—,

[structures: HO-isoxazole, dioxolane-$CH_3$]

—$S(O)_s$—[pyrazole], —$S(O)_s$—[imidazole],

—$S(O)_s$—[oxazolinone], —$S(O)_s$—[tetrazole],

—$S(O)_s$—[aryl-$NR^9H$, $R^{10}$], —S($O)_s$—[aryl-OH, $R^{10}$], wherein R*, $R^2$, $R^5$, and $R^6$ are as defined above;
$R^9$ is hydrogen or a straight or branched alkyl of from one to about six carbon atoms, —$(CH_2)_nCO_2R^*$, —$(CH_2)_nOAr'$, —$(CH_2)_nAr'$ or $(CH_2)_nNR^5R^6$, wherein n, R*, $R^5$, and $R^6$ are as defined above or taken from $R^3$ and Ar' is taken from Ar as defined below;
$R^{12}$ and $R^{13}$ are each independently hydrogen or are each independently taken with $R^3$ and $R^4$ respectively to form a moiety doubly bonded to the carbon atom; and Ar is a mono- or polycyclic unsubstituted or substituted carbo- or heterocyclic aromatic or hydroaromatic moiety.

16. A method for the treatment of idiopathic depression which comprises administering to a mammal in need of such treatment a therapeutically effective amount of a compound selected from (±)1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester, (R)-1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]dec-2-yl ester, (S)-1,3,4,9-tetrahydro-3-methyl-3-[[2-phenylethyl)amino]carbonyl]-2H-pyrido[3,4-b]indole-2-carboxylic acid, tricyclo[3.3.1.1$^{3,7}$]-dec-2-yl ester, 1,3,4,9-tetrahydro-3-[[[1-(hydroxymethyl)-2-phenylethyl]amino]carbonyl]-3-methyl-2H-pyrido-3,4-b]indole-2-carboxylic acid, tricyclo-[3.3.1.1$^{3,7}$]dec-2-yl ester (mixture of diastereomers), (R)-1,3,4,9-tetrahydro-3-[[[1-(hydroxymethyl)-2-phenylethyl]amino]carbonyl]-3-methyl-2H-pyrido[3,4-b]indole-2-carboxylic acid, tricyclo[3.3.1.1$^{3,7}$]dec-2-yl ester, (S)-1,3,4,9-tetrahydro-3-[[[1-(hydroxymethyl)-2-phenylethyl]amino]carbonyl]-3-methyl-2H-pyrido[3,4-b]indole-2-carboxylic acid, tricyclo[3.3.1.1$^{3,7}$]dec-2-yl ester, 1,3,4,9-tetrahydro-3-[[[1-(hydroxymethyl)-2-hydroxy-2-phenylethyl]amino]carbonyl]-3-methyl-2H-pyrido[3,4-b]indole-2-carboxylic acid, tricyclo[3.3.1.1$^{3,7}$]dec-2-yl ester, 3-[[(2-amino-2-phenylethyl)amino]carbonyl]1,3,4,9-tetrahydro-3-methyl]-2H-pyrido[3,4-b]indole-2-carboxylic acid, tricyclo[3.3.1.1$^{3,7}$]dec-2-yl ester, (mixtures of diastereomers), 3-[[[2-(3-carboxy-1-oxopropyl)-amino]-2-phenylethyl]amino]carbonyl]-1,3,4,9-tetrahydro-3-methyl-2H-pyrido[3,4-b]indole-2-carboxylic acid, tricyclo[3.3.1.1$^{3,7}$]dec-2-yl ester, [R-(R*,R*)]and [R-(R*,S*)]-, 3-[[[2-(R)-(3-carboxy-1-oxopropyl)amino]-2-phenylethyl]amino]carbonyl]-1,3,4,9-tetrahydro-3-(S)-methyl-2H-pyrido[3,4-b]indole-2-carboxylic acid, tricyclo[3.3.1.1$^{3,7}$]dec-2-yl ester, 3-[3-[3-[2-[2-[1,4-dioxo-4-(phenylmethoxy)butyl]amino]-2-phenylethyl]amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester (mixture of diastereomers).

3-[[(2-hydroxy-2-phenylethyl)amino]carbonyl]-1,3,4,9-tetrahydro-3-methyl]-2H-pyrido[3,4-b]indole-2-carboxylic acid, tricyclo[3.3.1.1$^{3,7}$]dec-2-yl ester, butanedioic acid, mono[2-[[[2,3,4,9-tetrahydro-3-methyl-2-[(tricyclo[3.3.1.1$^{3,7}$]dec-2-ylox)carbonyl]-1H-pyrido[3,4-b]indole-3-yl]carbonyl]amino]-1-phenethyl]ester.

3-[[[2-[(3-carboxyacetyl)amino]-2-phenethyl]amino]carbonyl]-1,3,4,9-tetrahydro-3-methyl-2H-pyrido[3,4-b]indole-2-carboxylic acid, [tricyclo[3.3.1.1$^{3,7}$]dec-2-yl ester (mixture of diastereomers), 3-[[[2-[(3-carboxy-1-oxo-2-propenyl)amino]2-phenethyl]amino]carbonyl]1,3,4,9-tetrahydro-3-methyl-2H-pyrido[3,4-b]indole-2-carboxylic acid, [tricyclo[3.3.1.1$^{3,7}$]dec-2-yl ester (mixture of diastereomers), 3-[[[1-[[(3-carboxy-1-oxopropyl)amino]methyl]-1-phenethyl]amino]carbonyl]-1,3,4,9-tetrahydro-3-methyl-2H-pyrido[3,4-b]indole-2-carboxylic acid, [tricyclo[3.3.1.1$^{3,7}$]dec-2-yl ester (mixture of diastereomers), (±)-1,3,4,9-tetrahydro-3-[[(2-phenethyl)amino]-carbonyl]-2H-pyrido[3,4-b]indole-2-ester, 3-[[(1-carboxy-2-phenethyl)amino]carbonyl]1,3,4,9-tetrahydro-2H-pyrido[3,4-b]indole-2-carboxylic acid, 1,1-dimethylethyl ester, (±)-1,3,4,9-tetrahydro-3-methyl-N-(2-phenylethyl)-2-[(tricyclo[3.3.1.1$^{3,7}$]dec-2-ylamino)sulfonyl]1H-pyrido[3,4-b]indole-3-carboxamide, 3-[[[3-carboxy-1-(phenylmethyl)propyl]amino]carbonyl]-1,3,4,9-tetrahydro-3-methyl-2H-pyrido[3,4-b]indole-2-carboxylic acid, tricyclo[3.3.1.1$^{3,7}$]dec-2-yl ester, 1,3,4,9-tetrahydro-3-methyl-3-[[[2-[[1-oxo-3-(1H-tetrazol-5-yl)propyl]amino]-2-phenethyl]amino]carbonyl]-2H-pyrido[3,4-b]indole-2-carboxylic acid, tricyclo[3.3.1.1$^{3,7}$]dec-2-yl ester, and 3-[[[2-[[(2-carboxy-1-cyclopropyl)carbonyl]amino]-2-phenethyl]amino]carbonyl]-1,3,4,9-tetrahydro-3-methyl-2H-pyrido[3,4-b]indole-2-carboxylic acid ethyl ester, tricyclo[3.3.1.1$^{3,7}$]dec-2-yl ester.

* * * * *

UNITED STATES PATENT AND TRADEMARK OFFICE
CERTIFICATE OF CORRECTION

PATENT NO. : 5,217,957

DATED : June 8, 1993

INVENTOR(S) : Geoffrey N. Woodruff

Page 1 of 5

It is certified that error appears in the above-indentified patent and that said Letters Patent is hereby corrected as shown below:

Column 47, line 47: Insert " † ", " ‡ ', and " ∓ " so that structure appears like this:

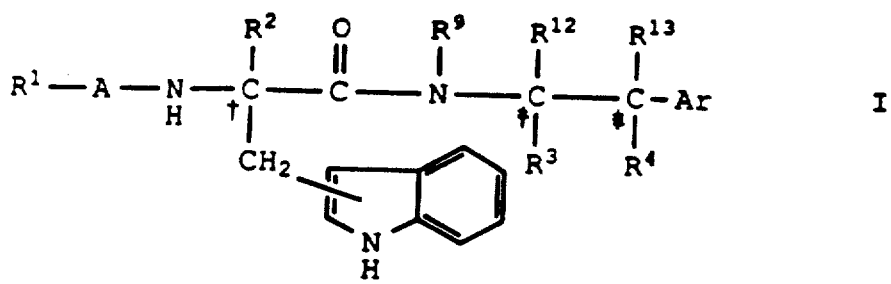

I

Column 48, line 9: delete "-C=CH," and insert "-C≡CH,"
Column 48, line 10: delete "-CH$_2$C=CH," and insert "-CH$_2$C≡CH,"
Column 48, line 11: insert "*" so as to read "-(CH$_2$)$_n$CO$_2$R*"
Column 48, line 12: insert "*" to read "R*, R$^5$ and R$^6$"

Column 51, line 33: delete "4β]]" and insert "4α]]"
Column 52, line 10: delete "H" and insert "H"
Column 52, line 11: insert "." to read "[3.3.1.1$^{3,7}$]"
Column 52, line 53: "3,7" should be superscript so as to read "[3.3.1.1$^{3,7}$]"
Column 52, line 56: "3,7" should be superscript so as to read "[3.3.1.1$^{3,7}$]"

UNITED STATES PATENT AND TRADEMARK OFFICE
CERTIFICATE OF CORRECTION

PATENT NO. : 5,217,957
DATED : June 8, 1993
INVENTOR(S) : Geoffrey N. Woodruff

It is certified that error appears in the above-indentified patent and that said Letters Patent is hereby corrected as shown below:

Column 55, line 27: "3,7" should be superscript so as to read "[3.3.1.1$^{3,7}$]"
Column 56, line 33: insert " ǂ " and " ǂ " so structure appears as:

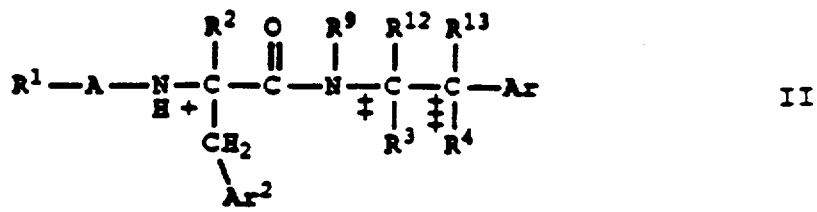

II

Column 60, line 11: insert "." to read "[3.3.1.1$^{3,7}$]"
Column 61, line 4: insert "1-" before "(hydrox-"
Column 64, line 44: delete "N" insert "N" so structure appears as:

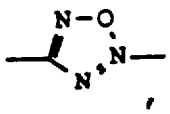

,

Column 64, line 60: insert "R$^3$ and" before "R$^4$"
Column 67, line 4: "3" is not a superscript, should read "5,13-Dioxa-"

UNITED STATES PATENT AND TRADEMARK OFFICE
CERTIFICATE OF CORRECTION

PATENT NO. : 5,217,957

DATED : June 8, 1993

INVENTOR(S) : Geoffrey N. Woodruff

It is certified that error appears in the above-indentified patent and that said Letters Patent is hereby corrected as shown below:

Column 67, line 22: after "-2-" insert "[[3-"
Column 68, line 5: delete "α" insert "ß"
Column 69, line 5: "AR'" should be "Ar'"
Column 70, line 20: after line 19 insert new line to read "-OH,"
Column 71, line 66: insert "." to read "[3.3.1.1$^{3,7}$]"
Column 72, line 10: insert " ≠ " and " ≠ " so structure appears as:

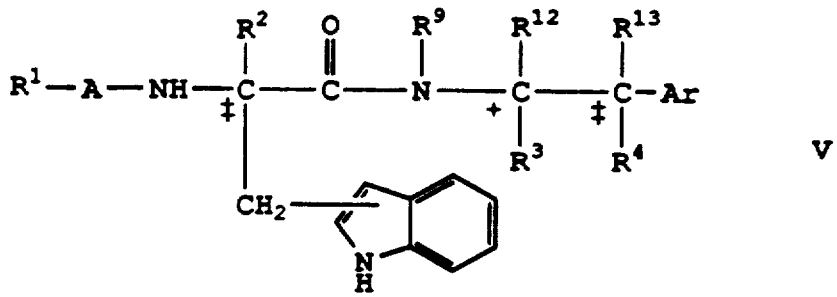

Column 73, line 7: delete "in" insert "integer"
Column 75, line 11: delete "dide" insert "iodide"
Column 75, line 20: before "yloxy)car-" insert "methyl-1-oxo-2-[[(tricyclo[3.3.1.1$^{3,7}$]dec-2-"
Column 75, line 36: before "depression" insert "idiopathic"
Column 77, line 6: subscript "2" should be superscript "2"

UNITED STATES PATENT AND TRADEMARK OFFICE
CERTIFICATE OF CORRECTION

PATENT NO. : 5,217,957

DATED : June 8, 1993

INVENTOR(S) : Geoffrey N. Woodruff

Page 4 of 5

It is certified that error appears in the above-indentified patent and that said Letters Patent is hereby corrected as shown below:

Column 77, line 54: twice in the line, delete subscript "b" and insert subscript "s"
Column 77, line 60: twice in the line, delete subscript "b" and insert subscript "s"
Column 77, line 66: twice in the line, delete subscript "b" and insert subscript "s"
Column 78, line 51: before "depression" insert "idiopathic"
Column 78, line 59: insert " + " and " ≠ " so structure appears:

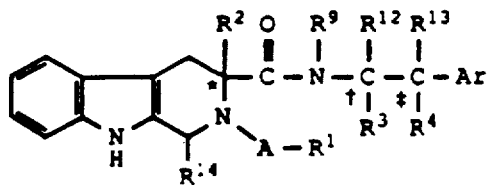

VII

UNITED STATES PATENT AND TRADEMARK OFFICE
CERTIFICATE OF CORRECTION

PATENT NO. : 5,217,957

DATED : June 8, 1993

INVENTOR(S) : Geoffrey N. Woodruff

It is certified that error appears in the above-indentified patent and that said Letters Patent is hereby corrected as shown below:

Column 82, line 28: before "ester," insert "carboxylic acid, [tricyclo[3.3.1.1$^{3,7}$]]-dec-2-yl Signed and Sealed this Fifth Day of April, 1994

Attest:

BRUCE LEHMAN

*Attesting Officer*  *Commissioner of Patents and Trademarks*